US009745556B2

(12) United States Patent
Wang et al.

(10) Patent No.: US 9,745,556 B2
(45) Date of Patent: Aug. 29, 2017

(54) VARIANTS OF GLYCEROL DEHYDROGENASE HAVING D-LACTATE DEHYDROGENASE ACTIVITY AND USES THEREOF

(71) Applicant: UNIVERSITY OF FLORIDA RESEARCH FOUNDATION, INC., Gainesville, FL (US)

(72) Inventors: Qingzhao Wang, Scarsdale, NY (US); Keelnatham T. Shanmugam, Gainesville, FL (US); Lonnie O'Neal Ingram, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 125 days.

(21) Appl. No.: 14/347,688

(22) PCT Filed: Oct. 4, 2012

(86) PCT No.: PCT/US2012/058657
§ 371 (c)(1),
(2) Date: Mar. 27, 2014

(87) PCT Pub. No.: WO2013/052604
PCT Pub. Date: Apr. 11, 2013

(65) Prior Publication Data
US 2014/0234924 A1 Aug. 21, 2014

Related U.S. Application Data

(60) Provisional application No. 61/543,003, filed on Oct. 4, 2011.

(51) Int. Cl.
| *C12N 9/04* | (2006.01) |
| *C12N 15/53* | (2006.01) |
| *C12P 7/56* | (2006.01) |
| *C12P 7/26* | (2006.01) |

(52) U.S. Cl.
CPC .............. *C12N 9/0006* (2013.01); *C12P 7/26* (2013.01); *C12P 7/56* (2013.01); *C12P 2203/00* (2013.01)

(58) Field of Classification Search
None
See application file for complete search history.

(56) References Cited

U.S. PATENT DOCUMENTS

| 7,098,009 | B2 | 8/2006 | Shanmugam et al. |
| 2008/0293101 | A1 | 11/2008 | Peters et al. |
| 2009/0197314 | A1 | 8/2009 | Atkinson et al. |
| 2012/0129231 | A1 | 5/2012 | Wang et al. |

FOREIGN PATENT DOCUMENTS

| WO | WO 2011012693 | 2/2011 |
| WO | WO 2012071392 | 5/2012 |

OTHER PUBLICATIONS

Database EBI, "Bacillus coagulans 36D1, complete genome," XP002738995, EBI Accession No. EM_STD:CP003056, Database Accession No. CP003056, Sep. 25, 2011, pp. 1-6.
Wang, Q. et al. "Metabolic Engineering of thermotolerant, acidophilic *Bacillus coagulans* for production of D(−)-lactic acid" In: *SIM Annual Meeting and Exhibition*, Jul. 26, 2011, Section S123, pp. 1.
Wang, Q. et al. "Evolution of D-lactate dehydrogenase activity from glycerol dehydrogenase and its utility for D-lactate production from lignocellulose" *PNAS*, Nov. 11, 2011, pp. 18920-18925, vol. 108 No. 47.
Datta, R. et al. "Lactic acid: recent advances in products, processes and technologies—a review" *Journal of Chemical Technology and Biotechnology*, 2006, pp. 1119-1129, vol. 81.
Grabar T.B. et al. "Methylglyoxal bypass identified as source of chiral contamination in L(+) and D(−)-lactate fermentations by recombinant *Escherichia coil*" *Biotechnology Letters*, 2006, pp. 1527-1535, vol. 28.
Hofvendahl, K. et al. "Factors affecting the fermentative lactic acid production from renewable resources" *Enzyme and Microbial Technology*, 2000, pp. 87-107, vol. 26.
Kim, Y. et al. "Construction of an *Escherichia coli* K-12 mutant for homoethanologenic fermentation of glucose or xylose without foreign genes" *Applied and Environmental Microbiology*, 2007, pp. 1766-1771, vol. 73.
Kim, Y. et al. "Dihydrolipoamide dehydrogenase mutation alters the NADH sensitivity of pyruvate dehydrogenase complex of *Escherichia coli* K-12" *Journal of Bacteriology*, 2008, pp. 3851-3858, vol. 190, No. 11.
Okano, K. et al. "Improved production of homo-D-lactic acid via xylose fermentation by introduction of xylose assimilation genes and redirection of the phosphoketolase pathway to the pentose phosphate pathway in L-Lactate dehydrogenase gene-deficient *Lactobacillus plantarum*" Applied *and Environmental Microbiology*, 2009, pp. 7858-7861, vol. 75, No. 24.
Ou, M. et al. "L: (+)-Lactic acid production from non-food carbohydrates by thermotolerant *Bacillus coagulans*" *The Journal of Industrial Microbiology and Biotechnology*, 2011, pp. 599-605, vol. 38.
Patel, M.A. et al. "Isolation and characterization of acid-tolerant, thermophilic bacteria for effective fermentation of biomass-derived sugars to lactic acid" Applied *and Environmental Microbiology*, 2006, pp. 3228-3235, vol. 72.

(Continued)

*Primary Examiner* — Rebecca Prouty
(74) *Attorney, Agent, or Firm* — Saliwanchik, Lloyd & Eisenschenk

(57) ABSTRACT

The present invention provides methods of designing and generating glycerol dehydrogenase (GlyDH) variants that have altered function as compared to a parent polypeptide. The present invention further provides nucleic acids encoding GlyDH polypeptide variants having altered function as compared to the parent polypeptide. Host cells comprising polynucleotides encoding GlyDH variants and methods of producing lactic acids are also provided in various aspects of the invention.

27 Claims, 24 Drawing Sheets
(1 of 24 Drawing Sheet(s) Filed in Color)

(56) References Cited

OTHER PUBLICATIONS

Payot, T. et al. "Lactic acid production by Bacillus coagulans—Kinetic studies and optimization of culture medium for batch and continuous fermentations" *Enzyme and Microbial Technology*, 1999, pp. 191-199, vol. 24.

Tanaka, K. et al. "Two different pathways for D-xylose metabolism and the effect of xylose concentration on the yield coefficient of L-lactate in mixed-acid fermentation by the lactic acid bacterium Lactococcus lactis IO-1" *Applied Microbiology and Biotechnology*, 2002, pp. 160-167, vol. 60.

Underwood, S.A. et al. "Genetic changes to optimize carbon partitioning between ethanol and biosynthesis in ethanologenic *Escherichia coli*" Applied *and Environmental Microbiology*, 2002, pp. 6263-6272, vol. 68.

Yanez, R. et al. "Production of D(−)-lactic acid from cellulose by simultaneous saccharification and fermentation using *Lactobacillus coryniformis* subsp. *torquens*" *Biotechnology Letters*, 2003, pp. 1161-1164, vol. 25.

Zhou S. et al. "Functional replacement of the *Escherichia coli* D-(−)-lactate dehydrogenase gene (IdhA) with the L-(+)-lactate dehydrogenase gene (IdhL) from Pediococcus acidilactici" *Applied and Environmental Microbiology*, 2003, pp. 2237-2244, vol. 69.

Written Opinion in International Application No. PCT/US2011/061807, Jul. 23, 2012, pp. 1-4.

Zhang, H. et al. "Engineering of glycerol dehydrogenase for improved activity towards 1,3-butanediol" *Appl. Microbiol Biotechnol*, 2010, pp. 117-124, vol. 88.

Mazumdar, S. et al. "*Escherichia coli* Strains Engineered for Homofermentative Production of D-Lactic Acid from Glycerol" *Applied and Environmental Microbiology*, Jul. 2010, pp. 4327-4336, vol. 76, No. 13.

Sato, S. et al. "Dehydrogenation of 1,3-butanediol over Cu-based catalyst" *Journal of Molecular Catalysis A: Chemical*, 2007, pp. 164-168, vol. 272.

Written Opinion in International Application No. PCT/US2012/058657, Feb. 28, 2013, pp. 1-5.

Chica, R. et al. "Semi-rational approaches toe engineering enzyme activity: combining the benefits of directed evolution and ration design" *Current Opinion in Biotechnology*, 2005, pp. 378-384, vol. 16.

Sen, S. et al. "Developments in Directed Evolution for Improving Enzyme Functions" *Appl Biochem Biotechnol*, 2007, pp. 212-223, vol. 143.

Wang, Q. et al. "Metabolic Flux Control at the Pyruvate Node in an Anaerobic *Escherichia coli* Strain with an Active Pyruvate Dehydrogenase" Applied *and Environmental Microbiology*, 2010, pp. 2107-2114, vol. 76, No. 7.

Romero, S. et al. "Metabolic Engineering of *Bacillus subtilis* for Ethanol Production: Lactate Dehydrogenase Plays a Key Role in Fermentative Metabolism" *Applied and Environmental Microbiology*, Aug. 2007, pp. 5190-5198, vol. 73, No. 16.

Su, Y. et al. "Physiological and fermentation properties of Bacillus coagulans and a mutant lacking fermentative lactate dehydrogenase activity" *The Journal of Industrial Microbiology and Biotechnology*, 2011, pp. 441-450, vol. 38.

Wang, Q. et al. "Construction and characterization of an *ldh* deletion mutant of *Bacillus coagulans*" *A special conference of the Society for industrial Microbiology, $32^{nd}$ Symposium on Biotechnology for Fuels and Chemicals*, Apr. 19, 2010, Section 1-10, pp. 1-2.

Shanmugam, K. T. et al. "Engineering Thermotolerant Biocatalysts for Biomass Conversion to Products" *Technical Report (final)*, May 20, 2010, DOE Contract No. FG36-04G014019.

Zhang, Z. et al. "One-step production of lactate from cellulose as the sole carbon source without any other organic nutrient by recombinant cellulolytic *Bacillus subtilis*" *Metabolic Engineering*, 2011, pp. 364-372, vol. 13.

Brenda [online], "Information on EC 1.1.1.6—glycerol dehydrogenase" retrieved on Sep. 20, 2016, retrieved from the internet, URL: http://www.brenda-enzymes.de/enzyme.php?ecno=1.1.1.6, pp. 1-9.

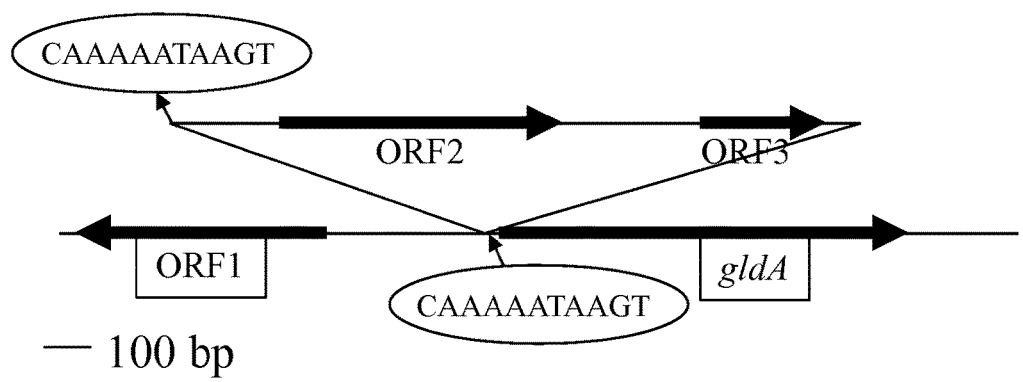
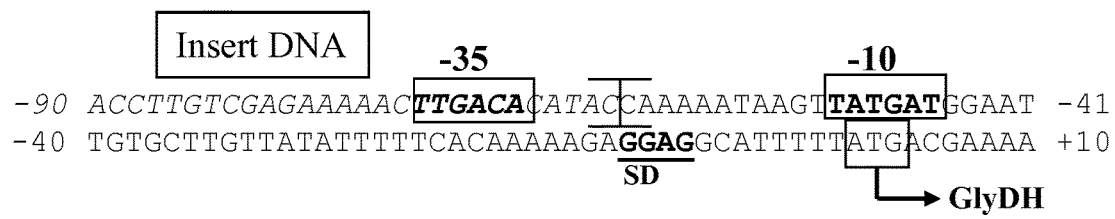
FIG. 5

```
  1 mTKIITSPSK FIQGPDELSR LSAYTERlgk KAFIIADDFV TGLVGKTVEE SYAGKETGYQ
 61 mALFGGEcSK PEIERLcEMS KSEEADVVVG IGGGKtldta kavgyynnip vivaptiast
121 naptsalsvi ykengefeey lmlplnptfv imdtkviasa parllvsgmg dalatyfear
181 atkrankttm aggrvteaai alaklcydtq ileglkaklA AEKHLVTEAV EKiieantyl
241 sgigsesggl aaahaihngl tvleethhmy hgekVAFGTL AQLILEDAPK aeieevvsfc
301 lsvglpvtlg dlgvkelnee klrkvaelsc aegetiynmp fevtpdlvya aivtadsvgr
361 yykekwa (SEQ ID NO: 1)
```

FIG. 11

```
Native GlyDH    MTKIITSPSKFIQGPDELSRLSAYTERLGKKAFIIADDFVTGLVGKTVEE    50
QZ19 GlyDH*     ..................................................    50

Native GlyDH    SYAGKETGYQMALFGGECSKPEIERLCEMSKSEEADVVVGIGGGKTLDTA    100
QZ19 GlyDH*     ..................................................    100

Native GlyDH    KAVGYYNNIPVIVAPTIASTDAPTSALSVIYKENGEFEEYLMLPLNPTFV    150
QZ19 GlyDH*     ....................N.............................    150

Native GlyDH    IMDTKVIASAPARLLVSGMGDALATYFEARATKRANKTTMAGGRVTEAAI    200
QZ19 GlyDH*     ..................................................    200

Native GlyDH    ALAKLCYDTQILEGLKAKLAAEKHLVTEAVEKIIEANTYLSGIGFESGGL    250
QZ19 GlyDH*     ...........................................S.....    250

Native GlyDH    AAAHAIHNGLTVLEETHHMYHGEKVAFGTLAQLILEDAPKAEIEEVVSFC    300
QZ19 GlyDH*     ..................................................    300

Native GlyDH    LSVGLPVTLGDLGVKELNEEKLRKVAELSCAEGETIYNMPFEVTPDLVYA    350
QZ19 GlyDH*     ..................................................    350

Native GlyDH    AIVTADSVGRYYKEKWA    367
QZ19 GlyDH*     .................    367
```

FIG. 12

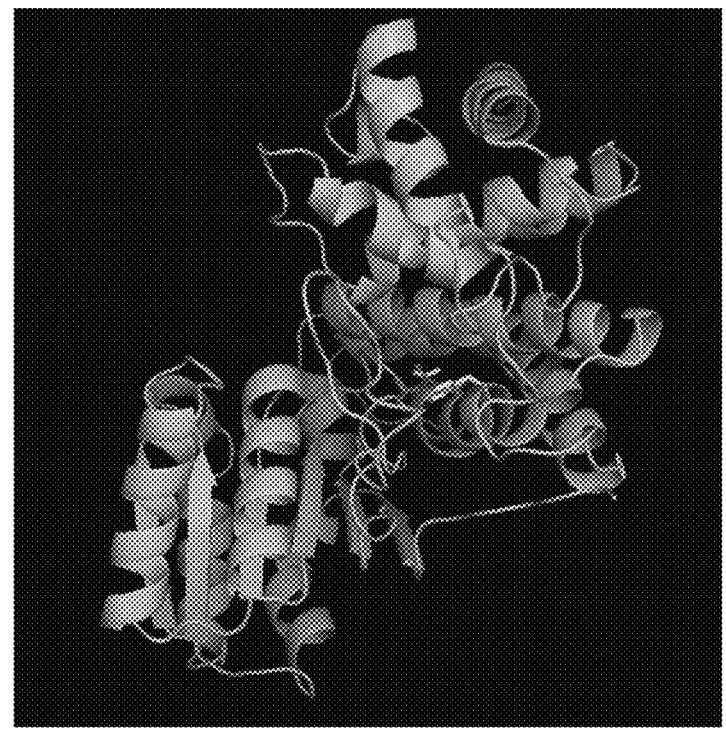
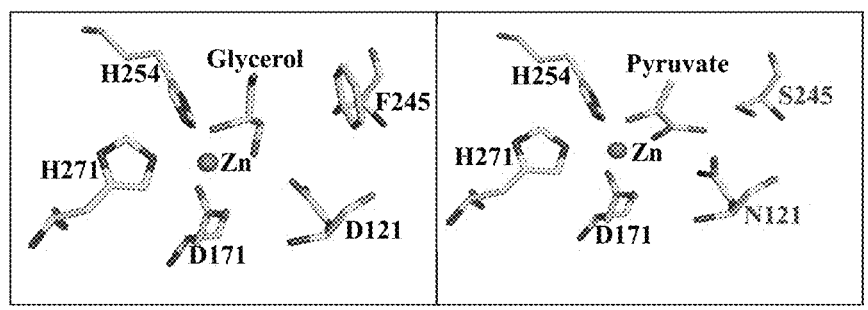
FIG 13

FIG. 14

Glycerol Dehydrogenase from *B. coagulans* strain P4-102B aligned with other bacterial GlyDHs

```
B. coagulans P4-102B              --------------------MTKIIT-SPSKFIQGPDELSRLSAYTERLGK 30
B. coagulans 36D1                 --------------------MTKIIT-SPSKFIQGPDELSRLSAYTERLGK 30
Symbiobacterium thermophilum      --------------------MSKVIV-APGKYIQGPGELDRLAEHTGQLGA 30
Vibrio parahaemolyticus           --------------------MDKIII-SPSKYVQGEQVLTSIAHYVKTLGE 30
Vibrio alginolyticus              --------------------MDKIII-SPSKYVQGEQVLTSIAHYVKTLGE 30
Psychromonas sp.                  --------------------MDKIII-SPSKYIQGENVLAAISEYVLPVGR 30
Pseudovibrio sp.                  --------------------MDQIII-SPSKYVQGEDTIAKIGDYIKPLGQ 30
Proteus penneri                   --------------------MLKVIQ-SPAKYIQGPDALYHIGKYAKPFGD 30
Proteus mirabilis                 --------------------MLKVIQ-SPAKYIQGPDALYHIGKYTKPLGE 30
Klebsiella pneumoniae             --------------------MLKVIQ-SPAKYLQGPDAAVLFGQYAKNLAE 30
Klebsiella varicola               --------------------MLKVIQ-SPAKYLQGPDAAVLFGQYAKNLAE 30
Citrobacter koseri                -----------------MTGMLKVIQ-SPAKYLQGPDASVLFGQYAKDLAD 33
Yersinia mollaretii               --------------------MLKVIQ-SPSKYIQGANALQSIGEFAKLLAN 30
Xenorhabdus bovienii              --------------------MLKVIQ-SPSKYIQGPGALSHIGQYTKILAD 30
T. thermosaccharolyticum          --------------------MTKAII-GPSKYVQGNGELRRISEHTKSLGK 30
Thermosediminibacter oceani       MRIPVPGVILIKYLGGRFTVTRAII-GPGKYVQGNGVLKDIKEHTMKLGR 49
Clostridium ljungdahlii           --------------------MSRIII-STGKYVQGNGELKNISNYVENLGD 30
Clostridium botulinum             --------------------MAKIII-SPSKYVQGNGELKKIYDHIGNLGK 30
Ruminococcus gnavus               --------------------MAKVLI-SPGKYVQGAGEMKKLGEYAQNYGK 30
Geobacillus thermoglucosidasius   --------------------MARIIN-SPTKYIQGRGELQNLGKYINSLGN 30
Salmonella enterica LT2           --------------------MDRIIQ-SPGKYIQGANVIARLGDYLKPMAN 30
Escherichia coli MG1655           --------------------MDRIIQ-SPGKYIQGADVINRLGEYLKPLAE 30
Enterobacter cloacae              --------------------MDRIIQ-SPGKYIQGADVLTRLGDYLKPLAT 30
Tolumonas auensis                 --------------------MDKIIQ-SPGKYVQGAGVISRVGQYAAPFAK 30
Sebaldella termitidis             --------------------MDKIIL-SPSKYVQGYNTIERLEVYTSSLGK 30
Paenibacillus sp. JDR-2           --------------------MRKAFI-SPSKYVQGENELLNLGFFVQSYGD 30
Geo. stearothermophilus           ------------------MAAERVFI-SPAKYVQGKNVITKIANYLEGIGN 32
Staphylococcus epidermidis        --------------------MSKFIYQSPGRYVQGKGIVSSIAEETERLGS 31
                                                          :  .  .. ::: *       .    .

B. coagulans P4-102B              KAFIIADDFVTGLVGKTVEESYAGKE-TGYQMALFGGECSKPEIERLCEM 79
B. coagulans 36D1                 KAFIIADDFVTGLVGKTVEESYAGKE-TGYQMALFGGECSKPEIERLCEM 79
Symbiobacterium thermophilum      HAFVIADEFVMNLTGDRVTASYAKAG-AAVTMERFQGEITQAEIERLTAR 79
Vibrio parahaemolyticus           RPLVIADEFVTNLVGDDVKQSFADEK-LPLTMNIFGGECSRVEIERITDI 79
Vibrio alginolyticus              RPLVIADEFVTNLVGDDVKQSFADEK-LPLTMNIFGGECSRVEIERITDI 79
Psychromonas sp.                  QAMAIADEFVTGLVGETVKQSFRDQD-SELTMEIFNGECSRTEIERLLLL 79
pseudovibrio|B6QWR7|B6QWR7_9RH    KAAILADSFVTGLVGDTVKKSCADAG-IEQRMEEFGGECSRAEIDRLMEI 79
Proteus penneri                   RALIIADKFVMDLVGSTVKDSMSQYE-VNGHFELFNGECTHNEINRLSEL 79
Proteus mirabilis                 RALIIADKFVMDLAGSIVKDSMTQYE-VNGHFEQFHGECTHKEIDRLVEI 79
Klebsiella pneumoniae             SFFVIADDFVMKLAGEKVVNGLQSHD-IRCHAERFNGECSHAEINRLMAI 79
Klebsiella varicola               SFFVIADDFVMKLAGEKVVNGLQSHD-IRCHAERFNGECSHVEINRLMAI 79
Citrobacter koseri                SFFVIADDFVMKLAGEKVLNGLNSHE-IRCHAERFNGECSHVEINRLMAI 82
Yersinia mollaretii               NYFIIADDFVMKLTADTVSSSLHGSE-LENHFSRFNGECSRQEIERLTVE 79
Xenorhabdus bovienii              HVFVIADNFVMSLIGDAVSKSLEAHA-VTSHFEIFNGECSRGEIKRLSDI 79
T. thermosaccharolyticum          NFLVIASSNGIIRTKSIIEESFSNTE-ISLCFESFGGECSEEEIERLRNF 79
Thermosediminibacter oceani       SFFIIASENGIKRTKPVIEESFAGEK-VELVFEPFNGECSENEIERLKGL 98
Clostridium ljungdahlii           SFFIIASENGIKRTRDAIEESFKGKD-SLLAFEAFNGECSKNEIDRLCKK 79
Clostridium botulinum             SFLFIVSKSGFKRTGDVIKKSFENTN-SKITFEIFNGECSHNEIERLKKV 79
Ruminococcus gnavus               KALILISKGGYKRIGAMVEKSFEGKE-CGYVFDYFNGECSKKEIKRLGEI 79
Geobacillus thermoglucosidasius   SFLVIADQFVLNFTKETIEQSFSDQE-STLTFETFRGECSKQEVNRLQTI 79
Salmonella enterica LT2           NWLVVGDKFVLGFAEETLRKSLTDAG-LSVEIAPFGGECSQNEIDRLRAV 79
Escherichia coli MG1655           RWLVVGDKFVLGFAQSTVEKSFKDAG-LVVEIAPFGGECSQNEIDRLRGI 79
Enterobacter cloacae              RWLVVGDKFVLGFAEETLRQSFKNAE-LHAEIAPFGGECSQNEIDRLKKL 79
Tolumonas auensis                 KLLVISDAFVLGLIEGKVTASFKESA-TDFVIEKFKGECSRNEVNRLITI 79
Sebaldella termitidis             NSLIIADDFITKIIKEPVSNSYQNSS-SNILFEKFNGECSKTEINRLMEI 79
Paenibacillus sp. JDR-2           SALLIAHPEDVKRVKDKLDFTSNKFN-ITLVESGFRGECSREEIARLKEL 79
Geo. stearothermophilus           KTVVIADEIVWKIAGHTIVNELKKGN-IAAEEVVFSGEASRNEVERIANI 81
Staphylococcus epidermidis        HALIIADEVVWNITEEKIKESFSANNNVDFEYEVFKGESSEEEIQRIVKQ 81
                                  :                              *  *  :. *: *
```

FIG. 14 (continued)

```
                                                                            D121N
B. coagulans QZ19
B. coagulans P4-102B                  SKSEEADVVVGIGGGKTLDTAKAVGYYN-NIPVIVAPTIASTDAPTSALS 128
B. coagulans 36D1                     SKSEEADVVVGIGGGKTLDTAKAVGYYN-NIPVIVAPTIASTDAPTSALS 128
Symbiobacterium thermophilum          CKESQADVVVGIGGGKTLDSAKAVAYYCGNLPAVVVPTVASTDAPCSALS 129
Vibrio parahaemolyticus               CATQKHDVIVGIGGGKTLDTAKAVAFYT-KIPVVVVPTIASTDAPTSALA 128
Vibrio alginolyticus                  CATQKHDVIVGIGGGKTLDTAKAVAFYT-KIPVVVVPTIASTDAPTSALA 128
Psychromonas sp.                      SEQANADVIIGIGGGKTLDTAKAIGFYR-KIPVVVVPTIASTDAPTSALA 128
pseudovibrio|B6QWR7|B6QWR7_9RH        FKAEGSDVVVGIGGGKTLDTAKAIGFYH-KIPVVVVPTIASTDAPTSALA 128
Proteus penneri                       VKEQASLVIVGVGGGKTLDTAKAVAYKC-QLPVVISPTIASTDAPTSALS 128
Proteus mirabilis                     AKQQAALVIIGVGGGKTLDTAKAVAYKC-QLPVVISPTIASTDAPTSALS 128
Klebsiella pneumoniae                 LQKQGCRGVVGIGGGKTLDTAKAIGYYQ-KLPVVVIPTIASTDAPTSALS 128
Klebsiella varicola                   LQKQGCRGVVGIGGGKTLDTAKAIGYYQ-KLPVVVIPTIASTDAPTSALS 128
Citrobacter koseri                    LKQKGCRGVVGIGGGKTLDTAKAIGYYQ-KLPVVIIPTIASTDAPTSALS 131
Yersinia mollaretii                   LKKHHCNGVIGIGGGKTLDTAKAIAHYQ-HIPVIVVPTIASTDAPTSALS 128
Xenorhabdus bovienii                  SASHQCQAVIGIGGGKTLDTAKAIAHAC-RLPVIISPTIASTDAPTSALS 128
T. thermosaccharolyticum              VKKTNSDVIVGIGGGKIFDTVKAVAYYE-NIPVVIVPTIASTDAPCSALS 128
Thermosediminibacter oceani           AEKNNSQVIVGIGGGKVLDTAKAIAYFL-KLPVVVVPTVASTDAPCSALS 147
Clostridium ljungdahlii               LKENKNNVVIGIGGGKIFDTAKAVAYYA-KVPVVIVPTIAATDAPCSALS 128
Clostridium botulinum                 CAENNCDVVVGVGGGKILDTAKAVSYYE-KSPVVIVPTIASTDAPCSALS 128
Ruminococcus gnavus                   VKKEACDVVIGIGGGKIFDTAKAVAYYE-KTPVLICPTIASTDAPCSALS 128
Geobacillus thermoglucosidasius       AKEKQIDVIVGVGGGKTLDTAKAVAFYS-KLPVVIVPTIASTDAPCSALS 128
Salmonella enterica LT2               AEKSQCGAVLGIGGGKTLDTAKALAHFM-NVPVAIAPTIASTDAPCSALS 128
Escherichia coli MG1655               AETAQCGAILGIGGGKTLDTAKALAHFM-GVPVAIAPTIASTDAPCSALS 128
Enterobacter cloacae                  ADSADCMAVLGIGGGKTLDTAKALAHFM-DVPVAIAPTIASTDAPCSALS 128
Tolumonas auensis                     LQNENCDGVVGVGGGKTLDTAKAVAYYA-KVPVVIAPTIASTDAPCSALS 128
Sebaldella termitidis                 IQQNKIDSIVGIGGGKTLDTAKAVSYYA-KIPVVIVPTIASTDAPCSALS 128
Paenibacillus sp. JDR-2               AREKNCSCTIGLGGGKAIDTAKCVAEGE---ALIIVPTIAATDAPTSHSA 126
Geo. stearothermophilus               ARKAEAAIVIGVGGGKTLDTAKAVADEL-DAYIVIVPTAASTDAPTSALS 130
Staphylococcus epidermidis            YKEKNIDVVIGLGGGKALDTGKAVAFEL-KASVIDFASTASMDAPTAAVS 130
                                       :*:****  :*: *. .         .: *: *** :   :

B. coagulans P4-102B                  VIYKENGEFEEYLMLPLNPTFVIMDTKVIASAPARLLVSGMGDALATYFE 178
B. coagulans 36D1                     VIYKENGEFEEYLMLPLNPTFVIMDTKVIASAPARLLVSGMGDALATYFE 178
Symbiobacterium thermophilum          VIYKEDGSFERYLFLPSNPAVVVVDTAIIANAPVRLLVAGMGDALASTYFE 179
Vibrio parahaemolyticus               VIYTPEGEFAEYLMIPKNPDMVIMDTSVIAKAPVRLLVSGMGDALSTYFE 178
Vibrio alginolyticus                  VIYTPEGEFAEYLMIPKNPDMVIMDTSVIAKAPVRLLVSGMGDALSTYFE 178
Psychromonas sp.                      VIYTPEGQFSEYLMIPTNPNMVIMDSKIIAAAPVRLLVSGMGDALSTHFE 178
pseudovibrio|B6QWR7|B6QWR7_9RH        VIYTPEGEFSEYLLFPSNPNLVIMDTKIIAGAPVRLLVAGIGDALSTYFE 178
Proteus penneri                       VIYTELGAFDSYLFYPTNPDVVVMDTNIIASAPARLLVAGMGDALATYFE 178
Proteus mirabilis                     VIYTELGAFDSYLFYPKNPDIVVMDTNVIASAPPRLLVAGMGDALATYFE 178
Klebsiella pneumoniae                 VIYTEAGEFEEYLIYPKNPDMVVMDTAIIAKAPVRLLVSGMGDALSTWFE 178
Klebsiella varicola                   VIYTEAGEFEEYLIYPKNPDMVVMDTAIIAKAPVRLLVSGMGDALSTWFE 178
Citrobacter koseri                    VIYTEAGEFEEYLIYPKNPDMVVMDTAIIAKAPVRLLVSGMGDALSTWFE 181
Yersinia mollaretii                   VIYTEQGEFAEYLIYPKNPDIVLMDSAIIAKAPVRLLVSGMGDALSTYFE 178
Xenorhabdus bovienii                  VLYTELGFDGYLLYPQNPNIVLMDTVTRIIAKAPVRLLVAGMGDALATYFE 178
T. thermosaccharolyticum              VIYTSEGIFSKYLLLPKNPDLVLVDTEIIASAPARLLVAGMGDALATYFE 178
Thermosediminibacter oceani           VIYTDEGVFSKYLILPRNPDVVMVDTGFIVKAPARLLAAGMGDALATYFE 197
Clostridium ljungdahlii               VIYTDEGVFSEYLALPKNPDLVLVDSSIVAKAPVRLLVSGMGDALATYFE 178
Clostridium botulinum                 VIYTEDGTFSEYILLPKNPDIVLMDTEIISKAPARLLVAGMGDALATFFE 178
Ruminococcus gnavus                   VIYTEGVFEEYLFLPSNPDMVMMDTEIIAESPVRLTVAGMGDALATYFE 178
Geobacillus thermoglucosidasius       VLYTEEGVFDEYLILPKNPDIVLVDTQIVANAPARLLAAGIGDALATYVE 178
Salmonella enterica LT2               VIYTDAGEFDRYLLLPHNPNMVIVDTQIVAGAPARLLAAGIGDALATWFE 178
Escherichia coli MG1655               VIYTDEGEFDRYLLLPNNPNMVIVDTKIVAGAPARLLAAGIGDALATWFE 178
Enterobacter cloacae                  VIYTDSGEFERYLMLPHNPNMVIVDTKVVAGAPPRLLAAGIGDALATWFE 178
Tolumonas auensis                     VIYTDTGEFESYLILPCNPNVVLVDTEIVAGAPARLLAAGIGDAMATYFE 178
Sebaldella termitidis                 VIYTDEGVFSEYLFLSKNPDLVIMDTKIIANAPVRLLAAGMGDALATYFE 178
Paenibacillus sp. JDR-2               VIYTNDGAFEDYAYFKSSPSVVMIDTTVIANAPTRFLVSGMGDALSTYFE 176
Geo. stearothermophilus               VIYSDDGVFESYRFYKKNPDLVLVDTKIIANAPPRLLASGIADALATWVE 180
Staphylococcus epidermidis            VIYNEDGSFSGYEFYPKNPDTVIVDSEIVAQAPVRLFASGMSDGLATLIE 180
                                       *:*.  * * *     .*  *: *: .:   :* *: ..*:.*..::* .*
```

FIG. 14 (continued)

```
B. coagulans P4-102B              ARATKRANKTTMAG-----------GRVTEAAIALAKLCYDTQILEGLK 216
B. coagulans 36D1                 ARATKRANKTTMAG-----------GRVTEAAIALAKLCYDTQISEGLK 216
Symbiobacterium thermophilum      ARAAQRAHKLNIVG-----------GHGTQAAMALARLCYDTLLQEGIK 217
Vibrio parahaemolyticus           ARANMTSGKATMAG-----------GLATRSAQALAKLCYETLLEDGLK 216
Vibrio alginolyticus              ARANMTSGKATMAG-----------GLATRSAQALAKLCYETLLEDGVK 216
Psychromonas sp.                  ARANARSGGKTMAG-----------GAPTKAAQALAKLCYETLLADGLQ 216
pseudovibrio|B6QWR7|B6QWR7_9RH    ARANGLSGKATMAG-----------GLPTKAAQALAKLCYETLLADGYK 216
Proteus penneri                   ARACSQAQKQTMAG-----------GKSTLAALALAELCYNTLLEDGYK 216
Proteus mirabilis                 ARACSRAQKQTMAG-----------GKTTLAALALAELCYHTLLEDGYK 216
Klebsiella pneumoniae             AKACYDARATSMAG-----------GQSTEAALSLARLCYDTLLAEGEK 216
Klebsiella varicola               AKACYDARATSMAG-----------GQSTEAALSLARLCYDTLLAEGEK 216
Citrobacter koseri                AKACYDARATSMAG-----------GQSTAAALSLARLCYDTLLAEGEK 219
Yersinia mollaretii               AQACFDAKAISMAG-----------GASTLAAVTLARLCYETLLAEGYK 216
Xenorhabdus bovienii              ARANSAAHKPTMAG-----------GATSNTGLALAKLCYDTLLAEGYK 216
T. thermosaccharolyticum          ARACLRSNASTMAG-----------AKSTKAAMALAKLCYDTLLEDGLK 216
Thermosediminibacter oceani       ARACFRSNATTLAG-----------GKSTKAAMALAELCYRTLLEDGLK 235
Clostridium ljungdahlii           ARACVRSGAVTMSG-----------GKATKAAFALSKLCYDTLLEDGLK 216
Clostridium botulinum             ARACAKANANNMSG-----------GKITKAALALATLCYETLIEDGLK 216
Ruminococcus gnavus               ARACQRSDAASCAG-----------GKITGAAMALAKLCFDTLMEEGVK 216
Geobacillus thermoglucosidasius   ARACYEANATPMAG-----------GTITKAAIALAELCQNILFEDGIK 216
Salmonella enterica LT2           ARACSRSGATTMAG-----------GKCTQAALALAELCYNTLIEEGEK 216
Escherichia coli MG1655           ARACSRSGATTMAG-----------GKCTQAALALAELCYNTLLEEGEK 216
Enterobacter cloacae              ARACSRSGATTMAG-----------GKCTQAALALAELCYNTLIEEGEK 216
Tolumonas auensis                 ARACYQSRATTMAG-----------GESTEAAMSLARLCFDTLLAEGHK 216
Sebaldella termitidis             ARACTAANKKTMAG-----------GTATKASAALAELCYNTLLSDGYL 216
Paenibacillus sp. JDR-2           ARATSRSFSKVNAGLPNGVHAGAAPIARGTKAALALAKLCYETLLEDGVQ 226
Geo. stearothermophilus           ARSVIKSGGKTMAG-----------GIPTIAAEAIAEKCEQTLFKYGKL 218
Staphylococcus epidermidis        VESTLRRQGQNMFH-----------GKPTLASLAIAQKCEEVIFEYGYS 218
                                  ..:                       : :.  :: *    : *

F245S
B. coagulans QZ19                 AKLAAEKHLVTEAVEKIIEANTYLSGIGFESGGLAAAHAIHNGLTVLE-E 265
B. coagulans P4-102B              AKLAAEKHLVTEAVEKIIEANTYLSGIGFESGGLAAAHAIHNGLTVLE-E 265
B. coagulans 36D1                 AKLAAEKHLVTEAVEKIIEANTYLSGIGFESGGLAAAHAIHNGLTVLE-E 265
Symbiobacterium thermophilum      AKAAAEAHVITEALERIVEANTYLSGLGFESCGLAAAHAIHNGLSALE-E 266
Vibrio parahaemolyticus           AKAAVENGVSTKAVENIIEANTYLSGIGFESSGLAGAHAIHNGLTKLE-E 265
Vibrio alginolyticus_             AKAAVENGVSTKAVENIIEANTYLSGIGFESSGLAGAHAIHNGLTKLE-E 265
Psychromonas sp.                  AKIAVENGLSSQAVENIIEANTYLSGLGFESSGLAGAHAIHNGLTKLE-E 265
pseudovibrio|B6QWR7|B6QWR7_9RH    AKVAVENRVSSTAVKNIIEANTLLSGLGFESSGLAAAHAIHNGLTKLE-E 265
Proteus penneri                   AKLAVSRGVCTAAVENIIEANTFLSGIGFESAGLAAAHAIHNGFTALE-E 265
Proteus mirabilis                 AKLAVSRSVCTTAVENIIEANTFLSGIGFESAGLAAAHAIHNGFTALE-E 265
Klebsiella pneumoniae             ARLAAQAGVVTEALERIIEANTYLSGIGFESSGLAAAHAIHNGFTILE-E 265
Klebsiella varicola               ARLAAQAGVVTEALERIIEANTYLSGIGFESSGLAAAHAIHNGFTILE-E 265
Citrobacter koseri                ARLAAQAGVVTDALERIVEANTYLSGIGFESSGLAGAHAIHNGFTILE-E 268
Yersinia mollaretii               AKLAVEAGVVTEAVERIIEANTYLSGIGFESSGLAAAHAIHNGFTVLE-E 265
Xenorhabdus bovienii              AKLAVEAGVSTPAVENIIEANTYLSGIGFESAGLAAAHAIHNGFTVLE-E 265
T. thermosaccharolyticum          AKLAVENKTVTKAVENIVEANTYLSGIGFESGGLAAAHAIHNGFTVIE-E 265
Thermosediminibacter oceani       AKLAVENNACTLAVENIVEANTYLSGIGFESGGLAAAHAIHNGFTVLE-E 284
Clostridium ljungdahlii           AKMAVINKVPTKAVENIIEANTYLSGVGFESSGLAAAHAIHNGFTALE-E 265
Clostridium botulinum             AKLAVEKKVCTKAVENIVEANTYLSGIGFESAGLAAAHAIHNGFTVLE-E 265
Ruminococcus gnavus               AKLALEADACTEAVEKVIEANTLLSGIGFESGGLAGAHAIHNGLTVLE-E 265
Geobacillus thermoglucosidasius   AFLAVEQNIVTKAVENIVEANTYLSGIGFESGGLAAAHAIHNGFTVID-D 265
Salmonella enterica LT2           AMLAAEQHVVTPALERIVEANTYLSGVGFESSGLAAAHAIHNGLTAIP-D 265
Escherichia coli MG1655           AMLAAEQHVVTPALERVIEANTYLSGVGFESSGLAAAHAVHNGLTAIP-D 265
Enterobacter cloacae              AMLAAEQHVVTPALERIIEANTYLSGVGFESSGLAAAHAIHNGMTAVP-D 265
Tolumonas auensis                 AMLAVQKKVVTEAVERIIEANTYLSGVGFESGGLAAAHAVHNGLTVIP-D 265
Sebaldella termitidis             AKLSVENKVVTKSLENIIEANTYLSGVGFESGGLAAAHAIHNGLTVVE-E 265
Paenibacillus sp. JDR-2           AKLASDSNKVTTALENIIETNILLSGLGFESGGLAAAHAIHNGLTVLE-G 275
Geo. stearothermophilus           AYESVKAKVVTPALEAVVEANTLLSGLGFESGGLAAAHAIHNGFTALEGE 268
Staphylococcus epidermidis        AYTSVEKHIVTPQVDAVIEANTLLSGLGFENGGLAGAHAIHNGFTALEGD 268
                                  *  :         :   :*:.   ***:***. ***.***:***:: :
```

FIG. 14 (continued)

```
B. coagulans P4-102B              THHMYHGEKVAFGTLAQLILEDAPKAEIEEVVSFCLSVGLPVTLGDLGVK 315
B. coagulans 36D1                 THHMYHGEKVAFGTLAQLILEDAPKAEIEEVVSFCLSVGLPVTLGDLGVK 315
Symbiobacterium thermophilum      THGAYHGEKVAFGTLAQLVLENAPLDEIEEVIEFCLNVGLPVTLADLGVH 316
Vibrio parahaemolyticus           CHHLYHGEKVAFGTLVQLVLENAAMEEINTVLAFCRSVGLPTNLFDMGVK 315
Vibrio alginolyticus              CHHLYHGEKVAFGTLVQLVLENAAMEEINTVLAFCRSVGLPTNLFDMGVK 315
Psychromonas sp.                  CHHLFHGEKVAFGTLVQLVLENAPMEEINTVLEFCHSVGLPTNLHAMGVK 315
pseudovibrio|B6QWR7|B6QWR7_9RH    CHHLYHGEKVAFGTLTQLLLENAPMEEIQEVLTLCRSVGLPTNLFDMGVK 315
Proteus penneri                   CHNMYHGEKVAFGTLVQLVLENSPLEELEEFLDFCILVGLPVTLEELGIN 315
Proteus mirabilis                 CHAMYHGEKVAFGTLVQLVLENSPLEEIEEVLDFCVQVGLPVTLEELGVH 315
Klebsiella pneumoniae             CHHLYHGEKVAFGTLAQLVLQNSPMDEIETVLGFCQRVGLPVTLAQMGVK 315
Klebsiella varicola               CHHLYHGEKVAFGTLAQLVLQNSPMDEIETVLGFCQRVGLPVTLAQMGVK 315
Citrobacter koseri                CHHLYHGEKVAFGTLAQLVLQNSPMEEIETVLGFCEKVGLPITLAQMGVK 318
Yersinia mollaretii               CHHLYHGEKVAFGTLTQLVLQNSSMEEIETVLSFCQQLGLPITLAEMGVT 315
Xenorhabdus bovienii              CHHLYHGEKVAFGTLAQLMLENSPNEELETVLDFCVQVGLPVTLEQLGLR 315
T. thermosaccharolyticum          CHQLYHGEKVAFGTLVQLVLENSPLEEIEEVVEFCMSVGLPVTLEDIGIK 315
Thermosediminibacter oceani       CHHMYHGEKVAFGTIVQLVLENSPMEELEEVVGFCLDVGLPVTLEDLGIK 334
Clostridium ljungdahlii           CHGLYHGEKVAFGALVQLVLENSPMEEIEEVIDFCLQVGLPITLNDLGIK 315
Clostridium botulinum             CHHLYHGEKVAFGTIVQLILENSPMEEIQEVLEFCIELGLPVTLKQLGIN 315
Ruminococcus gnavus               CHHMYHGEKVAFGTITQLVLENIPSEELQQVIDFCIECGLPVTLEQLGAG 315
Geobacillus thermoglucosidasius   THHLYHGEKVAFGVITQLVLENRSTEEIQKYIAFCTELGLPVTLEDMGIT 315
Salmonella enterica LT2           AHHYYHGEKVAFGTLTQLVLENAPVEEIETVAALCHSVGLPITLAQLDIK 315
Escherichia coli MG1655           AHHYYHGEKVAFGTLTQLVLENAPVEEIETVAALSHAVGLPITLAQLDIK 315
Enterobacter cloacae              AHHFYHGEKVAFGTLTQLVLENAPVEEIETVAALCHSVGLPITLAQLNIK 315
Tolumonas auensis                 AHHFYHGEKVAFGTLQLILENAPKAELDTVCALCTRVGLPITLAQLDIK 315
Sebaldella termitidis             LHHLYHGEKVTFGVLVQLVLENAPKNEIEDVLSFCKKINLPVCFKDMGIE 315
Paenibacillus sp. JDR-2           THHYFHGEKVAFSTIAQLVLENAPKEEVNEVLAFCAAVGLPVCLSDIGVD 325
Geo. stearothermophilus           IHHLTHGEKVAFGTLVQLALEEHSQQEIERYIELYLSLDLPVTLEDIKLK 318
Staphylococcus epidermidis        IHHLTHGEKVAYGILVQLVLENAPTEKFMKYKTFFDNINMPTTLEGLHIE 318
                                   *    *****::. :.** *::  . :.     :    .:*  :   :

B. coagulans P4-102B              ELN---EEKLRKVAELSCAEGETIYNMPFEVTPDLVYAAIVTADSVGRYY 362
B. coagulans 36D1                 ELN---EEKLRKVAELSCAEGETIYNMPFEVTPDLVYAAIVTADSVGRYY 362
Symbiobacterium thermophilum      TVR---EEQIRRVAELSCAEGETIFNMPFEVTPEKVYAAILTADRLGHLY 363
Vibrio parahaemolyticus           ELN---HAKLREVAEASTAEGETIHNMPFPVTAENVYSAILTAHQLGQ-- 360
Vibrio alginolyticus_             ELN---HAKLREVAEASTAEGETIHNMPFPVTAENVYSAILTAHQLGQ-- 360
Psychromonas sp.                  VLD---RDKLLEVAKASCAEGETIHNMPFVVTPIAVLSAILVAHELGSKK 362
pseudovibrio|B6QWR7|B6QWR7_9RH    ELD---HAKLMEVAEASCAEGETIHNMPFPVTPEMVYAAMLCAHQIGLK- 361
Proteus penneri                   ATGDELNEKIMAVAELSCAEGETIYNMPFDIDSDKVYAAILTADQLGREW 365
Proteus mirabilis                 ATGDELNEKIMAVAELSCAEGETIYNMPFDVDSDKVFAAIMAADQLGREW 365
Klebsiella pneumoniae             EG---IDEKIAAVAKATCAEGETIHNMPFAVTPESVHAAILTADLLGQQW 362
Klebsiella varicola               EG---IDAKIAAVAKATCAEGETIHNMPFAVTPESVHAAILTADLLGQQW 362
Citrobacter koseri                DG---IEGKIQAVAKATCAEGETIHNMPFEVTPDSVYAAILTADLLGQQW 365
Yersinia mollaretii               QD---IERKIRAVAQASCAEGETIHNMPFAVTPDSVYAAIIVADSLGEAF 362
Xenorhabdus bovienii              DSE-KLHQKIMEVAKASCAEGETIHNMPFKVTPEQVYAAIMAADRMGMDW 364
T. thermosaccharolyticum          EIN---YEKIKKVAEASCAPDETIHNMPFKVVAADVYAAILSADAIGKMY 362
Thermosediminibacter oceani       EVK---EADIRKVAEASCAEGETIHNMPFKVTPEDVYNAILGADALGRTL 381
Clostridium ljungdahlii           KVN---NEDIMKVAEISCAENDTMHNMPFEVTKEDVYSAILAADELGKQY 362
Clostridium botulinum             EIN---EEKLMEVSKTSCAEGETIYNMPFEVTPNDVYAAILAADALGQSL 362
Ruminococcus gnavus               KIT---EEQLMKVAEAACAETDTLHNMPFEVTPKKVADAIKAADAYGHYF 362
Geobacillus thermoglucosidasius   EDI---EPKIRKVAEAACQEGETIYNMPFPVTPDDVYAAIISADILGRKY 362
Salmonella enterica LT2           QDI---PAKMRTVAEASCAEGETIHNMPGGATPDEVYAALLVADQYGQRF 362
Escherichia coli MG1655           EDV---PAKMRIVAEAACAEGETIHNMPGGATPDQVYAALLVADQYGQRF 362
Enterobacter cloacae              EDI---PAKMRLIAEASCAEGETIHNMPGGVSPDQVYAALLVADQYGQRF 362
Tolumonas auensis                 EGI---EEKMRAAAEAACAEGETIHSMPFKVTATKVYAAMIAADQYGQDY 362
Sebaldella termitidis             NIN---KEKIYEAAKLACAEGETIYNMPFEVTVDDVYSAILTANSLGEDF 362
Paenibacillus sp. JDR-2           SIT---DEELAQVAALACIPEESIHAMPFPITEEAVAAAIIVADQLGQAF 372
Geo. stearothermophilus           DAS---REDILKVAKAATAEGETIHN-AFNVTADDVADAIFAADQYAKAY 364
Staphylococcus epidermidis        NTS---YEELVQVGERALTPNDTFANLSDKITADEIADAILTVNDLSKSQ 365
                                              .   . :    :::   .      :   *:  ..  .
```

FIG. 14 (continued)

```
B. coagulans P4-102B              KEKWA- 367
B. coagulans 36D1                 KEKWA- 367
Symbiobacterium thermophilum      KGG--- 366
Vibrio parahaemolyticus           ------
Vibrio alginolyticus_             ------
Psychromonas sp.                  ------
pseudovibrio|B6QWR7|B6QWR7_9RH    ------
Proteus penneri                   LY---- 367
Proteus mirabilis                 LY---- 367
Klebsiella pneumoniae             LAR--- 365
Klebsiella varicola               LAR--- 365
Citrobacter koseri                LAR--- 368
Yersinia mollaretii               LN---- 364
Xenorhabdus bovienii              LY---- 366
T. thermosaccharolyticum          KNKRSR 368
Thermosediminibacter oceani       KNQYIR 387
Clostridium ljungdahlii           K----- 363
Clostridium botulinum             S----- 363
Ruminococcus gnavus               LGE--- 365
Geobacillus thermoglucosidasius   K----- 363
Salmonella enterica LT2           LQEWE- 367
Escherichia coli MG1655           LQEWE- 367
Enterobacter cloacae              LQEWE- 367
Tolumonas auensis                 IKQNTK 368
Sebaldella termitidis             SS---- 364
Paenibacillus sp. JDR-2           KQGRKS 378
Geo. stearothermophilus           KEKHRK 370
Staphylococcus epidermidis        FN---- 367
```

FIG. 17

**Insertion sequence upstream of the *gldA* gene in *Bacillus coagulans* strain QZ19**

```
   1  caaaaataag tatgtgtaaa attttactcg acggggcata tgagtggaaa aaaatgggaa
  61  gacgctctat catctaattg tacacttcaa gatgaacatc tagagagaga ggtcttccca
 121  tggatattat atcaataatt gctggattat taaaggatac aaagagtctt atcgaatttg
      >..........................ORF-2............................>
 181  aagaacagct taaacttctg atgcagaagg cttttacaca atgggttggg gaaatatttg
      >..........................ORF-2............................>
 241  aagagttaga taaaataatt aaacaggaga agttagagga gggctgggtg tactgccgga
      >..........................ORF-2............................>
 301  gtgataacag aaacattcag tttctatttg gaagtgtgac ctttaaacgt tcattaatgc
      >..........................ORF-2............................>
 361  atgacaagag aggaaattcc cattatcctc tggatgaatg gttagggctg gtaccacacc
      >..........................ORF-2............................>
 421  aacgatacag cccgttagtg gaattaaagg tggcagagtt ggcaagtgag aacacctatc
      >..........................ORF-2............................>
 481  gggaagtagc tgatatttta aaagagtgga cagcagtgag tcttagtcac acaactgtag
      >..........................ORF-2............................>
 541  ggaacatggt aaaacacgta gggaaaactc aggcggaagc cgataaggca cttgtagaag
      >..........................ORF-2............................>
 601  agctagaaat agctgtttcc ctgcctgagg ggaagaaggt agactacctg ttttctgaag
      >..........................ORF-2............................>
 661  cagatggtgt attcgttcgg ggactaaaaa agaaacagag tatggaagtc caccacgcca
      >..........................ORF-2............................>
 721  ttctctatga gggatggcaa accaatggta aaagggtctc cctgcgtcag cccacagtca
      >..........................ORF-2............................>
 781  tcatgacaac ggaagccatc cagacatttt ggggatgaag tccaagcaca gctgccaaca
      >...............ORF-2.................>>
 841  cctactccct cgaaaaaacg catgtcatta caaacagtga tggaggtgcg ggatacacag
 901  ctgaacggtt tcaaacagct ttctcacagt cggaatttcc ggtgctcaac cagctggata
 961  cctaccacgt tgcacaagcc atcataagga catttggggg cggaaagagc gagatcaagg
1021  agcaaattag aaaagcgatt agaacgcatg acctggacca actcacgtta tatttggata
1081  cgcacgaaag caccttgacg gataaaaagg ctctcaagaa aatcaaggaa ttccgttcgt
1141  atatcttgaa aaactgggac cgcattttg actggagaga cagggtgaaa aacgtgccgg
1201  aaggtgcgag aggcctagga gcgatggaat cgaatcaaag gcatatctcc ttcaggatga
      >>..............ORF-3.................>
1261  aaaaaagggg catgcattgg agtgaacttg gcgcagaagc catggtgaaa atcaaacaag
      >..........................ORF-3............................>
1321  gcatactcaa tgggacattg agagaagtct atctgaaaca ccgttcaaga agcgagagaa
      >..........................ORF-3............................>
1381  agcaacggaa cttgaaacaa ttcatcagga tgtctcaact gctcaagcag cctgtacgcc
      >..........................ORF-3............................>
1441  cgtcagtggg cgtaaagcac ggatcagttg ccctgcattc aagcagttca tcggcaatgg
      >..........................ORF-3............................>
1501  gacatttaag caaaatatta gagctttcgt tttaagcctg gctcagtggg gactgatcgt
      >...............ORF-3.................>>
1561  tgaggcgcgc gaaatttacg agactcctgc gggaaaagcg agccaggaga daccccgcag
1621  cgaggtacga gcgaggaggc tcgccggccg accgcggaaa gcgagtgaat ttcgcgcgcc
1681  tcaacatccc cgttatccat ctttatacgg aaatattaca tcttttccga aaattacacc
1741  gagcaagtaa agcacggtag ccgaaagtgt acaaaagag tgtcttggaa tacccgatat
1801  ttaaaccttg tcgagaaaaa cttgacacat ac
```

FIG. 18
Insertion sequence upstream of the *gldA* gene of *Bacillus coagulans* strain QZ19 with the *gldA* gene included

```
   1  caaaaataag tatgtgtaaa attttactcg acggggcata tgagtggaaa aaaatgggaa
  61  gacgctctat catctaattg tacacttcaa gatgaacatc tagagagaga ggtcttccca
                                                                        >
 121  tggatattat atcataatt gctggattat taaaggatac aaagagtctt atcgaatttg
      >..................ORF-3..............................>
 181  aagaacagct taaacttctg atgcagaagg cttttacaca atgggttggg gaaatatttg
      >..................ORF-3..............................>
 241  aagagttaga taaaataatt aaacaggaga agttagagga gggctgggtg tactgccgga
      >..................ORF-3..............................>
 301  gtgataacag aaacattcag tttctatttg gaagtgtgac ctttaaacgt tcattaatgc
      >..................ORF-3..............................>
 361  atgacaagag aggaaattcc cattatcctc tggatgaatg gttagggctg gtaccacacc
      >..................ORF-3..............................>
 421  aacgatacag cccgttagtg gaattaaagg tggcagagtt ggcaagtgag aacacctatc
      >..................ORF-3..............................>
 481  gggaagtagc tgatatttta aaagagtgga cagcagtgag tcttagtcac acaactgtag
      >..................ORF-3..............................>
 541  ggaacatggt aaaacacgta gggaaaactc aggcggaagc cgataaggca cttgtagaag
      >..................ORF-3..............................>
 601  agctagaaat agctgtttcc ctgcctgagg ggaagaaggt agactacctg ttttctgaag
      >..................ORF-3..............................>
 661  cagatggtgt attcgttcgg ggactaaaaa agaaacagag tatggaagtc caccacgcca
      >..................ORF-3..............................>
 721  ttctctatga gggatggcaa accaatggta aaagggtctc cctgcgtcag cccacagtca
      >..................ORF-3..............................>
 781  tcatgacaac ggaagccatc cagacatttt ggggatgaag tccaagcaca gctgccaaca
      >................ORF-3.................>>
 841  cctactccct cgaaaaaacg catgtcatta caaacagtga tggaggtgcg ggatacacag
 901  ctgaacggtt tcaaacagct ttctcacagt cggaatttcc ggtgctcaac cagctggata
 961  cctaccacgt tgcacaagcc atcataagga catttggggg cggaaagagc gagatcaagg
1021  agcaaattag aaaagcgatt agaacgcatg acctggacca actcacgtta tatttggata
1081  cgcacgaaag caccttgacg gataaaaagg ctctcaagaa aatcaaggaa ttccgttcgt
1141  atatcttgaa aaactgggac cgcattttg actggagaga cagggtgaaa aacgtgccgg
1201  aaggtgcgag aggcctagga gcgatggaat cgaatcaaag gcatatctcc ttcaggatga
                            >>................ORF-6...............>
1261  aaaaaagggg catgcattgg agtgaacttg gcgcagaagc catggtgaaa atcaaacaag
      >..................ORF-6..............................>
1321  gcatactcaa tgggacattg agagaagtct atctgaaaca ccgttcaaga agcgagagaa
      >..................ORF-6..............................>
1381  agcaacggaa cttgaaacaa ttcatcagga tgtctcaact gctcaagcag cctgtacgcc
      >..................ORF-6..............................>
1441  cgtcagtggg cgtaaagcac ggatcagttg ccctgcattc aagcagttca tcggcaatgg
      >..................ORF-6..............................>
1501  gacatttaag caaaatatta gagctttcgt tttaagcctg gctcagtggg gactgatcgt
      >................ORF-6.........>>
```

FIG. 18 (continued)

```
1561  tgaggcgcgc gaaatttacg agactcctgc gggaaaagcg agccaggaga gaccccgcag
1621  cgaggtacga gcgaggaggc tcgccggccg accgcggaaa gcgagtgaat ttcgcgcgcc
1681  tcaacatccc cgttatccat ctttatacgg aaatattaca tcttttccga aaattacacc
1741  gagcaagtaa agcacggtag ccgaaagtgt acaaaaagag tgtcttggaa tacccgatat 1801  ttaaaccttg tcgagaaaaa cttgacacat acCAAAAATA AGTTATGATG GAATTGTGCT 1861  TGTTATATTT TTCACAAAAA GAGGAGGCAT TTTTATGACG AAAATCATTA CCTCTCCAAG
                                                 >>..........gldA............>
1921  CAAGTTTATA CAAGGCCCCG ATGAATTGTC CAGGCTTTCG GCGTATACGG AAAGGCTTGG
      >.................................gldA...................................>
1981  CAAAAAAGCA TTTATTATTG CGGATGATTT TGTCACCGGC CTTGTCGGCA AAACGGTTGA
      >.................................gldA...................................>
2041  AGAAAGCTAT GCCGGCAAAG AAACGGGGTA TCAAATGGCA TTATTCGGTG GCGAGTGTTC
      >.................................gldA...................................>
2101  TAAACCGGAA ATCGAACGGC TTTGTGAAAT GAGCAAATCC GAGGAAGCCG ATGTCGTTGT
      >.................................gldA...................................>
2161  CGGAATCGGC GGCGGAAAAA CATTGGATAC CGCAAAAGCA GTCGGGTATT ACAATAACAT
      >.................................gldA...................................>
2221  TCCGGTGATT GTCGCGCCGA CCATCGCTTC CACCAATGCC CCGACAAGCG CCCTGTCTGT
      >.................................gldA...................................>
2281  TATTTACAAA GAGAACGGCG AGTTTGAAGA ATACTTGATG CTGCCGCTGA ACCCGACTTT
      >.................................gldA...................................>
2341  TGTCATTATG GATACGAAAG TGATTGCCTC TGCCCCTGCC CGCCTGCTCG TTTCCGGCAT
      >.................................gldA...................................>
2401  GGGAGATGCG CTTGCGACGT ATTTTGAAGC GCGCGCCACT AAGCGGGCAA ATAAAACGAC
      >.................................gldA...................................>
2461  GATGGCAGGC GGGCGTGTTA CGGAAGCGGC GATCGCGCTT GCAAAACTTT GTTATGACAC
      >.................................gldA...................................>
2521  GCAAATTTTG GAAGGTTTAA AAGCAAAACT GGCAGCGGAA AAACATCTTG TTACGGAAGC
      >.................................gldA...................................>
2581  AGTGGAAAAA ATCATTGAAG CGAATACGTA TCTGAGCGGA ATCGGTTCTG AAAGCGGCGG
      >.................................gldA...................................>
2641  CCTTGCTGCG GCACATGCGA TCCATAATGG GCTTACCGTG CTCGAAGAAA CCCATCATAT
      >.................................gldA...................................>
2701  GTACCACGGC GAAAAAGTGG CATTCGGTAC CCTCGCCCAG CTGATTTTGG AAGATGCGCC
      >.................................gldA...................................>
2761  GAAAGCGGAA ATTGAAGAGG TGGTCTCCTT CTGCCTGAGT GTCGGACTTC CCGTCACGCT
      >.................................gldA...................................>
2821  CGGGGATTTG GGCGTGAAAG AACTGAATGA GGAAAAGCTC CGAAAAGTGG CTGAACTTTC
      >.................................gldA...................................>
2881  CTGTGCGGAA GGCGAAACGA TTTATAACAT GCCGTTTGAA GTCACGCCTG ACCTTGTGTA
      >.................................gldA...................................>
2941  CGCAGCAATC GTTACCGCTG ATTCCGTCGG GCGGTATTAT AAGGAAAAAT GGGCATGACA
      >.................................gldA...................................>>
3001  GTAAAAAGGG GCTGCTCCCG GTTCCGGGGA CAGCCCTTTT TGCCCATTTT CACTGTAATC
3061  CAGTTGTACA GATTTTTTCT TCCAGTTCGT CTTTTTCGGC CGCTGATAGC AGGTTTTCAG
```

FIG. 19

Native gldA sequence without the insertion sequence
Position of insertion is marked by arrow

```
   1  cgttcttctg ctaacatcct tcattcctcc gtctgatgat attttatcac atagttattc
  61  ataatcaacc gttttcaatc aaaaaatatc attttattc aaaacacatc atatttctgt
 121  cacattttgt cgatacagct ctattttact tgttattccc cgaaaattga acgtttttga
 181  aaaagtatgg atgataggat gaaaaggttt tcttatctgc aaaaataagt tatgatggaa
 241  ttgtgcttgt tatattttc acaaaaagag gaggcatttt tatgacgaaa atcattacct
                                                       >>......gldA.......>
 301  ctccaagcaa gtttatacaa ggccccgatg aattgtccag gctttcggcg tatacggaaa
      >...........................gldA............................>
 361  ggcttggcaa aaaagcattt attattgcgg atgattttgt caccggcctt gtcggcaaaa
      >...........................gldA............................>
 421  cggttgaaga aagctatgcc ggcaaagaaa cggggtatca aatggcatta ttcggtggcg
      >...........................gldA............................>
 481  agtgttctaa accggaaatc gaacggcttt gtgaaatgag caaatccgag gaagccgatg
      >...........................gldA............................>
 541  tcgttgtcgg aatcggcggc ggaaaaacat tggataccgc aaaagcagtc gggtattaca
      >...........................gldA............................>
 601  ataacattcc ggtgattgtc gcgccgacca tcgcttccac caatgccccg acaagcgccc
      >...........................gldA............................>
 661  tgtctgttat ttacaaagag aacggcgagt ttgaagaata cttgatgctg ccgctgaacc
      >...........................gldA............................>
 721  cgactttttgt cattatggat acgaaagtga ttgcctctgc ccctgcccgc ctgctcgttt
      >...........................gldA............................>
 781  ccggcatggg agatgcgctt gcgacgtatt ttgaagcgcg cgccactaag cgggcaaata
      >...........................gldA............................>
 841  aaacgacgat ggcaggcggg cgtgttacgg aagcggcgat cgcgcttgca aaactttgtt
      >...........................gldA............................>
 901  atgacacgca aattttggaa ggtttaaaag caaaactggc agcggaaaaa catcttgtta
      >...........................gldA............................>
 961  cggaagcagt ggaaaaaatc attgaagcga atacgtatct gagcggaatc ggttctgaaa
      >...........................gldA............................>
1021  gcggcggcct tgctgcggca catgcgatcc ataatgggct taccgtgctc gaagaaaccc
      >...........................gldA............................>
1081  atcatatgta ccacggcgaa aaagtggcat tcggtaccct cgcccagctg attttggaag
      >...........................gldA............................>
1141  atgcgccgaa agcggaaatt gaagaggtgg tctccttctg cctgagtgtc ggacttcccg
      >...........................gldA............................>
1201  tcacgctcgg ggatttgggc gtgaaagaac tgaatgagga aaagctccga aaagtggctg
      >...........................gldA............................>
1261  aactttcctg tgcggaaggc gaaacgattt ataacatgcc gtttgaagtc acgcctgacc
      >...........................gldA............................>
1321  ttgtgtacgc agcaatcgtt accgctgatt ccgtcgggcg gtattataag gaaaaatggg
      >...........................gldA............................>
1381  catgacagta aaagggggct gctcccggtt ccggggacag ccctttttgc ccatttttcac
      >..>>
1441  tgtaatccag ttgtacagat tttttcttcc agttcgtctt tttcggccgc tgatagcagg
```

VARIANTS OF GLYCEROL DEHYDROGENASE HAVING D-LACTATE DEHYDROGENASE ACTIVITY AND USES THEREOF

CROSS-REFERENCE TO RELATED APPLICATION

This application claims the benefit of U.S. Provisional Application Ser. No. 61/543,003, filed Oct. 4, 2011, the disclosure of which is hereby incorporated by reference in its entirety, including all figures, tables and amino acid or nucleic acid sequences.

This invention was made with government support awarded by Department of Energy (DE-FG36-04G014019 and DE-FG36-08G088142) and U.S. Department of Agriculture, National Institute of Food and Agriculture (2011-10006-30358). The government has certain rights in the invention.

BACKGROUND OF THE INVENTION

Petroleum serves as the primary source of automotive fuel and as the dominating feedstock for organic chemicals and plastics. The finite nature of the petroleum reserves and the negative environmental impact of petroleum use have shifted attention towards alternatives from renewable feedstocks (1-4). Fermentation of carbohydrates has been shown to produce short chain hydroxy acids as well as other chemicals that can be polymerized into plastics and replace petroleum (5). Commercial production of lactic acid using pure bacterial cultures started as early as 1895 (6) and current annual production is >300,000 metric tons. Although lactic acid is primarily used by food and pharmaceutical industries, its application in production of polylactic acid biopolymers (PLA) is expected to exceed other uses, provided the cost of PLA production can be lowered (7, 8).

Lactic acid is condensed into lactide dimers, purified and polymerized into a thermoplastic (7, 9). Blending D(−)- and L(+)-lactic acid polymers provides substantial control of the physical and thermochemical properties and the rate of biodegradation (9). Although lactic acid can be synthesized from petroleum, chemical synthesis produces a mixture of isomers that are not suitable for PLA. Optically pure lactic acid required for PLA synthesis can be readily produced by microbial fermentation (8). L(+)-lactic acid is produced commercially by lactic acid bacteria such as *Lactobacillus*, *Lactococcus*, etc. at high yield and titers from glucose and sucrose at temperatures between 30° C. and 40° C. (8, 10). Derivatives of *Escherichia coli* are the only known commercial D(−)-lactic acid producers (11, 12) and these also operate optimally at 40° C. or lower.

Alternative sources of fermentable sugars such as lignocellulosic biomass and improved microbial biocatalysts are needed to eliminate the use of food carbohydrates (glucose, sucrose) for lactic acid production (13). With cellulose as a feedstock, however, commercial fungal cellulases represent a significant process cost. This cost could be reduced by the development of thermotolerant biocatalysts that effectively ferment under conditions that are optimal (pH 5.0, 50° C.) for fungal cellulases (14, 15).

Lactic acid biocatalysts used by industry metabolize pentose sugars (from hemicellulose) by the phosphoketolase pathway, preventing efficient conversion of these sugars to lactic acid. Lactic acid produced from pentoses using this pathway is contaminated with an equimolar amount of acetic acid (FIG. 1) (8, 16-18). Attempts to improve the xylose fermentation properties of these lactic acid bacteria have met with limited success (18, 19). Although all the pentoses in hemicellulose are efficiently fermented by the *E. coli* derivatives to D(−)- or L(+)-lactic acid through the pentose-phosphate pathway, the temperature or pH tolerance of this biocatalyst is insufficient to permit cellulosic fermentations at the optimal temperature (50° C.) or pH (5.0) for commercial cellulases (20).

*Bacillus coagulans* has many desirable properties for the fermentation of lignocellulosic sugars into lactic acid. This bacterium ferments both hexoses and pentoses to L(+)-lactic acid using the highly efficient pentose phosphate pathway (FIG. 1) at 50-55° C. and pH 5.0, conditions that are optimal for commercial fungal cellulases (15, 17, 21). Native strains produce optically pure L(+)-lactic acid at concentrations as high as 180 g $L^{-1}$ in fed-batch fermentations from either glucose or xylose, and perform well during simultaneous saccharification and fermentation (SSF) of cellulose using fungal cellulases (21, 22). This match in optima both for the fermentation of *B. coagulans* and for fungal cellulase activity allowed a 4-fold reduction in cellulase usage in comparison to SSF with mesophilic bacterial biocatalysts (21). *B. coagulans* also grows and ferments sugars in mineral salt medium with inexpensive corn steep liquor (0.25%, w/v) supplementation in contrast to lactic acid bacteria that require complex nutrients (8, 15, 18). Although *B. coagulans* has excellent potential as a biocatalyst for the conversion of cellulose to optically pure L(+)-lactic acid, an equivalent microbe for production of D(−)-isomer of lactic acid has not been previously described.

BRIEF SUMMARY OF THE INVENTION

The present invention provides methods of designing and generating glycerol dehydrogenase (GlyDH) variants that have altered function as compared to a parent polypeptide. The present invention further provides nucleic acids encoding GlyDH polypeptide variants having altered function as compared to the parent polypeptide. Host cells comprising polynucleotides encoding GlyDH variants and methods of producing lactic acids are also provided in various aspects of the invention.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIG. 5. Insertion of DNA in the upstream region of gldA gene of *B. coagulans* strain QZ13 that enhanced gldA expression. An insert DNA (1,821 bp) indicated in italics starts after "C" at −62 of the gldA gene ("A" in ATG as +1) and continues upstream. An eleven base direct repeat (enclosed within the oval) is present at the ends of the insertion, one at the 5-end of the insert and the second at the 5-end of the gldA gene immediately after the 3-end of the insert. ORF1, a putative DeoR family transcriptional regulator; ORF2 and ORF3 in the insert DNA, putative transposase; gldA, glycerol dehydrogenase. Putative −10, −35 and Shine-Dalgarno sequences (SD) are indicated.

FIG. 11. Amino acid sequence of glycerol dehydrogenase with D-lactate dehydrogenase activity from *B. coagulans* strain QZ19. The amino acids in uppercase were identified after trypsin digestion and LC-MS/MS of fragments.

FIG. 12. Amino acid sequence of glycerol dehydrogenase (GlyDH) (SEQ ID NO: 3) from *B. coagulans* wild type strain P4-102B and its D-lactate producing derivative, strain QZ19 (SEQ ID NO:1), which contains two mutational changes in the GlyDH (GlyDH*).

FIG. 13. Model of *B. coagulans* GlyDH based on *B. stearothermophilus* GlyDH (PDB 1JPU) constructed by Swiss-Model. Native enzyme is colored green and the enzyme from QZ19 (GlyDH*) is in cyan and superimposed. Amino acids 121 and 245 are highlighted, native amino acid in yellow and the altered amino acid (strain QZ19) in magenta. Bottom: Only the amino acids at the active site, based on *B. stearthermophilus* enzyme structure, are listed. Left, native GlyDH with glycerol at the active site; right, GlyDH* (D121N, F245S) with pyruvate at the active site.

FIG. 14 provides an alignment of various GlyDH polypeptides (SEQ ID NOs: 5-32). As indicated in the alignment, the aspartic acid and phenylalanine found at the positions corresponding to amino acids 121 and 245 of SEQ ID NO: 3 are conserved among all the polypeptides.

FIG. 17. Insertion sequence upstream of the gldA gene in *Bacillus coagulans* strain QZ19 (SEQ ID NO: 53).

FIG. 18. Insertion sequence upstream of the gldA gene of *Bacillus coagulans* strain QZ19 with the gldA gene included. Lowercase letters represent the insertion sequence and uppercase letters represent the gldA sequence and its immediate upstream sequence up to the location of the insertion (after −62 with "A" in "ATG" as +1). The sequence "ttgaca" in lower case, bold, italicized and underlined _____ (positions 1822-1827 in SEQ ID NO: 54) is the putative −35 sequence that was introduced into the gldA upstream sequence by the insertion sequence. The native upstream sequence of gldA did not have the putative −35 sequence. Introduction of this new −35 sequence through the insertion enabled the gldA gene to be expressed and the protein produced at a high level in strain QZ13 and its descendents. The putative −10 sequence from the native gldA gene is also highlighted (bold, italics and double-underlined).

FIG. 19. Native gldA sequence without the insertion sequence. Position of insertion is marked by an arrow (after base 219 of SEQ ID NO: 55).

DETAILED DISCLOSURE OF THE INVENTION

Figure 1:
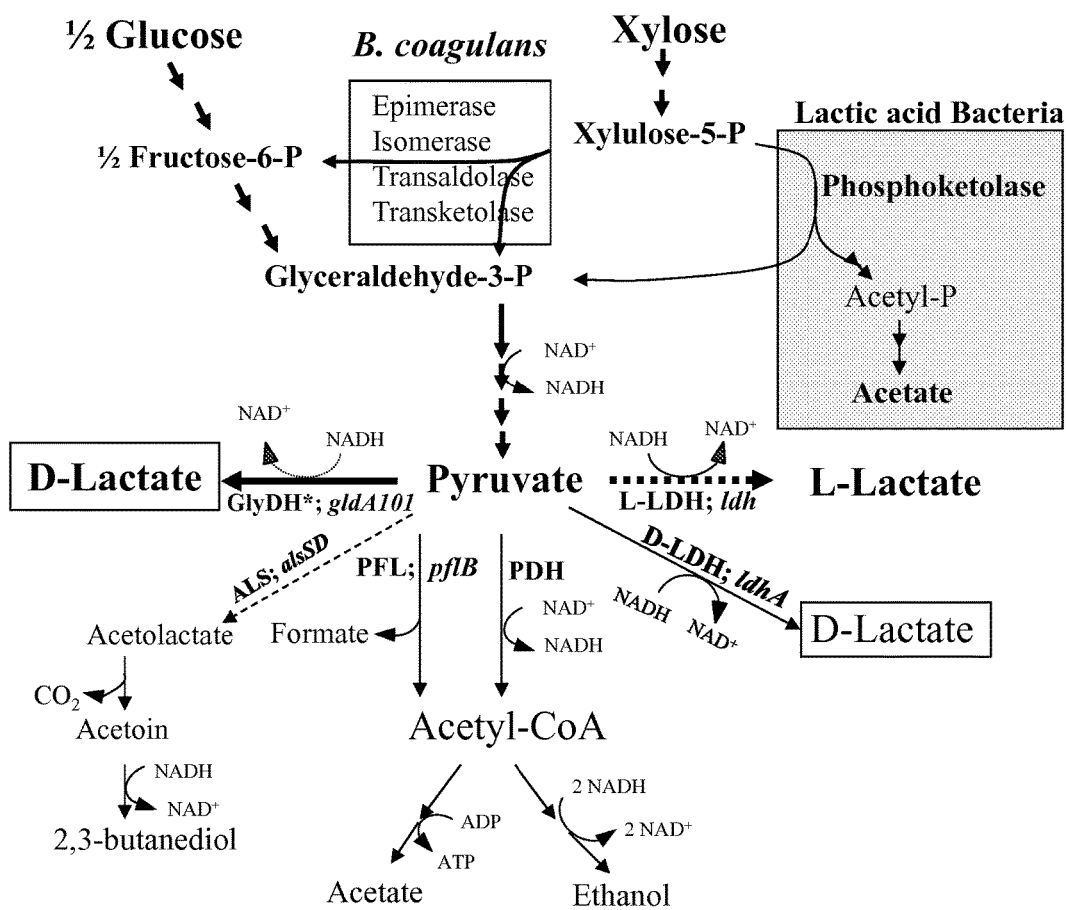
FIG. 1. Anaerobic metabolic pathways of glucose and xylose in *B. coagulans* strain P4-102B. Thickness of the arrow indicates glucose or xylose flux to L-lactate (broken line) as the preferred route during anaerobic growth of wild type and to D-lactate in strain QZ19 constructed in this study. Broken arrows (L-LDH and ALS) represent mutations in the two pathways introduced in this study. Xylose fermentation pathway in lactic acid bacteria, such as *L. lactis* utilizing phosphoketolase pathway resulting in an equimolar lactate and acetate, is also presented for comparison. See Patel et al. for details on pentose fermentation by *B. coagulans* and *L. lactis* (17).

"Nucleotide sequence", "polynucleotide" or "nucleic acid" can be used interchangeably and are understood to mean, according to the present invention, either a double-stranded DNA, a single-stranded DNA or products of transcription of the said DNAs (e.g., RNA molecules). It should also be understood that the present invention does not relate to genomic polynucleotide sequences in their natural environment or natural state. The nucleic acid, polynucleotide, or nucleotide sequences of the invention can be isolated, purified (or partially purified), by separation methods including, but not limited to, ion-exchange chromatography or molecular size exclusion chromatography, or by genetic engineering methods such as amplification, subtractive hybridization, cloning, subcloning or chemical synthesis, or combinations of these genetic engineering methods.

Both protein and nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW. Sequence comparisons are typically conducted using default parameters provided by the vendor or using those parameters set forth in the above-identified references, which are hereby incorporated by reference in their entireties. As discussed below, GlyDH sequences can be aligned to identify phenylalanine and aspartic acid amino acid residues that correspond to those found at positions 245 and 121, respectively, of SEQ ID NO: 3, and those amino acids can be subsequently substituted by another amino acid, such as serine or asparagine.

The subject invention also provides genetic constructs comprising a polynucleotide sequence encoding a variant GlyDH polypeptide. Genetic constructs as disclosed herein can contain additional regulatory elements such as promoters and enhancers and, optionally, selectable markers. Also within the scope of the subject invention are vectors or expression cassettes containing genetic constructs as set forth herein or polynucleotides encoding the variant GlyDH polypeptides disclosed herein operably linked to regulatory elements. The vectors and expression cassettes may contain additional transcriptional control sequences as well. The vectors and expression cassettes may further comprise selectable markers. The expression cassettes may contain at least one additional gene, operably linked to control elements, to be co-transformed into the organism. Alternatively, the additional gene(s) and control element(s) can be provided on multiple expression cassettes. Such expression cassettes are provided with a plurality of restriction sites for insertion of the sequences of the invention to be under the transcriptional regulation of the regulatory regions. The expression cassette(s) may additionally contain selectable marker genes operably linked to control elements.

The expression cassette will include, in the 5'-3' direction of transcription, a transcriptional and translational initiation region, a DNA sequence of the invention, and a transcriptional and translational termination region. The transcriptional initiation region, the promoter, may be native or analogous, or foreign or heterologous, to the host cell. By "foreign" is intended that the transcriptional initiation region is not found in the organism into which the transcriptional initiation region is introduced.

The subject invention also provides for the expression of a variant GlyDH polypeptide, encoded by a polynucleotide sequence disclosed herein comprising the culture of a host cell transformed with a polynucleotide encoding said variant GlyDH polypeptide under conditions that allow for the expression of the polypeptide and, optionally, recovering the expressed polypeptide.

Yet another aspect of the invention provides polynucleotides encoding a variant GlyDH (e.g., SEQ ID NO: 1), as well as recombinant vectors and recombinant host cells comprising the nucleic acids or recombinant vectors encoding a variant GlyDH. In one embodiment, the polynucleotide encoding the variant GlyDH of SEQ ID NO: 1 comprises SEQ ID NO: 2.

Yet another aspect of the invention provides variant GlyDH polypeptides having D-lactate dehydrogenase activity. In various embodiments of this aspect of the invention, a GlyDH polypeptide is mutated (altered) such that a phenylalanine corresponding to position 245 of SEQ ID NO: 3 is substituted with a serine (F245S) and/or an aspartic acid corresponding to position 121 of SEQ ID NO: 3 is substituted with an asparagine (D121N). In one embodiment, the variant GlyDH has a single amino acid substitution (F245S or D121N). Other embodiments provide a variant GlyDH that has two amino acid substitutions (F245S or D121N). Yet another embodiment provides a variant GlyDH that comprises SEQ ID NO: 1, or a fragment thereof that has D-lactate dehydrogenase activity. In certain preferred embodiments, fragments of the variant GlyDH polypeptides disclosed herein retain at least one property or activity of the full-length variant GlyDH polypeptide. Such a property or activity is D-lactate dehydrogenase activity. Another embodiment of this aspect of the invention provides for the substitution of the amino acid corresponding to the phenylalanine at position 245 with an amino acid that is synonymous to serine (e.g., Thr, Gly or Asn) and the aspartic acid at corresponding to position 121 of SEQ ID NO: 3 is substituted with an amino acid that is synonymous to asparagine (e.g., Gln).

Other aspects of the invention provide compositions comprising the GlyDH variants disclosed herein. In various embodiments, such compositions typically comprise a carrier, such as a buffer or other liquid medium, in combination with a variant GlyDH as disclosed herein.

Yet another aspect of the invention provides a promoter that causes increased constitutive expression of nucleic acid sequences that are operably linked to the promoter. The new reconstructed promoter (FIG. 5) appears to function constitutively and the level of transcription from this promoter is high (Table 2; gldA mRNA level; Protein level in the SDS-PAGE gel—FIG. 4). This promoter functions in *Bacillus coagulans* (Gram-positive) and *E. coli* (Gram-negative). The "-10 and -35" sequences are essentially *E. coli* consensus and derived by insertion of the transposon. In some embodiments, the nucleotides cga aaattacacc gagcaagtaa agcacggtag ccgaaagtgt acaaaaagag tgtcttggaa tacccgatat ttaaaccttg tcgagaaaaa cttgacacat acCAAAAATA AGTTAT-GATG GAATTGTGCT TGTTATATTT TTCAC (SEQ ID NO: 56) or tcgagaaaaa cttgacacat acCAAAAATA AGTTAT-GATG GAATTGTGCT TGTTATATTT TTCAC (nucleotides 84-148 of SEQ ID NO: 56) can be operably linked to a heterologous sequence in order to drive expression of a heterologous gene sequence.

Yet other aspects of the invention provide bacterial cells, fungal cells and yeast cells that demonstrate increased production of D-lactic acid (have increased D-lactate dehydrogenase activity), as compared to reference bacterial, fungal or yeast cells (cells not producing a variant GlyDH polypeptide as disclosed herein). Bacterial cells can be either Gram-negative bacteria or Gram-positive bacteria. In this aspect of the invention, the Gram-negative bacterial cell can be selected from a genus selected from the group consisting of *Escherichia, Zymomonas, Acinetobacter, Gluconobacter, Geobacter, Shewanella, Salmonella, Enterobacter* and *Klebsiella*. Gram-positive bacteria can be selected from the group consisting of *Bacillus, Clostridium, Corynebacterium, Lactobacillus, Lactococcus, Oenococcus, Streptococcus* and Eubacterial cells. Various thermophilic bacterial cells, such as Thermoanaerobes (e.g., *Thermoanaerobacterium saccharolyticum*), can also be manipulated to increase lactic acid production by way of expression of a variant GlyDH polypeptide as disclosed herein. Other thermophilic microorganisms include, but are not limited to, *Bacillus* spp., e.g., *Bacillus coagulans* strains, *Bacillus licheniformis* strains, *Bacillus subtilis* strains, *Bacillus amyloliquifaciens* strains, *Bacillus megaterium* strains, *Bacillus macerans* strains, *Paenibacillus* spp. strains or *Geobacillus* spp. such as *Geobacillus stearothermophilus* strains which can be genetically modified. Other *Bacillus* strains can be obtained from culture collections such as ATCC (American Type Culture Collection) and modified (transformed with a polynucleotide encoding one or more variant GlyDH polypeptides) to have increased lactate dehydrogenase activity by expression of one or more of the variant GlyDH polypeptides disclosed herein. Certain embodiments specifically exclude *B. coagulans* strain QZ19 (deposited Nov. 4, 2010 with the Agricultural Research Service Culture Collection, 1815 N. University Street, Peoria, Ill., 61604 U.S.A as accession number NRRL B-50443) in its native (untransformed) state.

Other embodiments provide for a yeast cell or fungal cell having increased D-lactate dehydrogenase activity. The yeast cell may be a *Candida, Hansenula, Kluyveromyces, Pichia, Saccharomyces, Schizosaccharomyces,* or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

In other embodiments, the cell having increased D-lactate dehydrogenase activity may be a fungal cell. "Fungi" as used herein includes the phyla Ascomycota, Basidiomycota, Chytridiomycota, Zygomycota, Oomycota and all mitosporic fungi. A fungal cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell. For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, Proc. Natl. Acad. Sci. USA 81: 1470-1474, and Christensen et al., 1988, Bio/Technology 6: 1419-1422. Suitable methods for transforming *Fusarium* species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, J. Bacteriol. 153: 163; and Hinnen et al., 1978, Proc. Natl. Acad. Sci. USA 75: 1920.

Various other aspects of the invention provide methods of producing lactic acid. In these aspects of the invention, known bacterial, fungal or yeast cells are transformed with a polynucleotide that encodes a variant GlyDH as disclosed herein and then used to produce D-lactic acid. In various embodiments, the methods comprise culturing a bacterial, fungal or yeast cell comprising a polynucleotide encoding a variant GlyDH as disclosed herein under conditions that allow for the production of D-lactic acid.

As used herein, "isolated" refers to bacterial, fungal or yeast cells partially or completely free from contamination by other bacteria. An isolated bacterial, fungal or yeast cell can exist in the presence of a small fraction of other bacteria which do not interfere with the properties and function of the isolated bacterial, fungal or yeast cell (e.g., a bacterial, fungal or yeast cell having increased D-lactate dehydrogenase activity). An isolated bacterial, fungal or yeast cell will generally be at least 30%, 40%, 50%, 60%, 70%, 80%, 85%, 90%, 95%, 98%, or 99% pure. Preferably, an isolated bacterial, fungal or yeast cell according to the invention will be at least 98% or at least 99% pure. A "recombinant cell" is a bacterial, fungal or yeast cell that contains a heterologous polynucleotide sequence (e.g., a polynucleotide encoding a variant GlyDH as disclosed herein).

A wild-type bacterial, fungal or yeast cell is the typical form of an organism or strain, for example a bacterial cell, as it occurs in nature, in the absence of mutations. Wild-type refers to the most common phenotype in the natural population. "Parental bacterial, fungal or yeast strain", "parental bacterial strain", "parental fungal strain" or "parental yeast strain" is the standard of reference for the genotype and phenotype of a given bacterial, fungal or yeast cell and may be referred to as a "reference strain" or "reference bacterial, fungal or yeast cell". A "parental bacterial, fungal or yeast strain" may have been genetically manipulated or be a "wild-type" bacterial cell depending on the context in which the term is used. Where D-lactate dehydrogenase expression is increased in genetically modified bacterial, fungal or yeast cells, the reference strain or reference bacterial, fungal or yeast cell will be a wild-type bacterial, fungal or yeast cell.

In various embodiments, compositions comprising microbial cells, such as a bacterial, fungal or yeast cells, transformed with a polynucleotide encoding a variant GlyDH polypeptide as disclosed herein are provided. These compositions can comprise a culture medium appropriate for a particular microbial cell which has been transformed with a polynucleotide encoding a variant GlyDH polypeptide as disclosed herein.

The terms "increasing", "increase", "increased" or "increases" refer to increasing by at least 5%, for example, 5, 6, 7, 8, 9, 10, 15, 20, 25, 30, 35, 40, 45, 50, 55, 60, 65, 70, 75, 80, 85, 90, 95, 99, 100% or more, a particular activity (e.g., increased D-lactate dehydrogenase activity or the increased production of D-lactic acid).

Various aspects of the invention provide for the use of a variety of hydrolysates for the production of D-lactic acid, including, but not limited to, hydrolysate derived from a biomass, a hemicellulosic biomass, a lignocellulosic biomass or a cellulosic biomass. Yet other aspects of the invention provide a bacterial, fungal or yeast cell with increased D-lactate dehydrogenase activity that produces D-lactic acid.

Another aspect of the present invention provides methods of designing and generating glycerol dehydrogenase (GlyDH) variants that have altered function as compared to a parent polypeptide. The present invention further provides nucleic acids encoding GlyDH polypeptide variants having altered function as compared to the parent polypeptide (e.g., alteration of a native GlyDH polypeptide within a host cell or another GlyDH polypeptide such that phenylalanine corresponding to the phenylalanine at position 245 of SEQ ID NO: 3 is changed to serine, glycine, threonine or asparagine and/or the aspartic acid corresponding to the aspartic acid at position 121 of SEQ ID NO: 3 is changed to an asparagine or glutamine). Host cells comprising polynucleotides encoding GlyDH variants and methods of producing lactic acids are also provided in various aspects of the invention.

One aspect of the present invention provides methods of designing and generating GlyDH variants that have altered function as compared to a parent polypeptide. The methods generally involve: a) providing a library of GlyDH polypeptides and aligning the amino acid sequences; b) selecting one or more of the GlyDH polypeptides; c) altering an amino acid corresponding to phenylalanine at position 245 of SEQ ID NO: 3 to serine, glycine, threonine or asparagine and/or altering an amino acid corresponding to aspartic acid at position 121 of SEQ ID NO: 3 to an asparagine or glutamine; and d) optionally testing the altered GlyDH polypeptide for the ability to produce lactic acid. In some embodiments, the individual effect of a single amino acid substitution (at either a phenylalanine corresponding to position 245 or an aspartic acid corresponding to position 121 of SEQ ID NO: 3) on the function of a GlyDH polypeptide is determined. In other embodiments, the effect of two amino acid substitutions (substitutions at a phenylalanine corresponding to position 245 and an aspartic acid corresponding to position 121 of SEQ ID NO: 3) on the function of a GlyDH polypeptide is determined.

In another aspect of the invention, the variant GlyDH polypeptides have altered substrate specificity and/or altered activity as compared to the parent GlyDH polypeptide. Particularly, the variant GlyDH polypeptides can be used to produce D-lactate (D-lactic acid). One embodiment of this aspect of the invention provides a polypeptide comprising SEQ ID NO: 1, or fragments thereof that catalyze the formation of D-lactic acid or have D-lactate dehydrogenase activity.

Finally, the terms "comprising", "consisting of" and "consisting essentially of" are defined according to their standard meaning. The terms may be substituted for one another throughout the instant application in order to attach the specific meaning associated with each term. The phrases "isolated" or "biologically pure" refer to material that is substantially or essentially free from components which normally accompany the material as it is found in its native state. Thus, isolated peptides in accordance with the invention preferably do not contain materials normally associated with the peptides in their in situ environment.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1

Materials and Methods

Bacterial Strains and Plasmids

Bacterial strains, plasmids and primers used in this study are listed in Tables 3 and 4. *B. coagulans* strain P4-102B used as the wild-type strain was described previously (17). Plasmid pGK12 replicates in several Gram-positive bacteria and *E. coli* (30, 31) and its replication is naturally restricted to temperatures ≤42° C. This temperature-sensitive nature of plasmid pGK12 replication at 50° C. provides an opportunity to select for chromosomal DNA integrants of *B. coagulans* that can grow at 50-55° C.

Medium and Growth Condition

Growth and fermentation conditions have been described previously (15, 21-23). Cultures were grown in L-broth (LB) at pH 5.0 or 7.0, as needed. Sterile glucose was added before inoculation.

Gene Deletions in *B. coagulans*

Construction of deletion mutants of *B. coagulans* was based on previously described methods (32). Plasmid pGK12 was used as the primary vehicle for transfer of DNA to *B. coagulans* for deletion construction. Presence of plasmid in each cell in a population ($10^9$ CFU $ml^{-1}$) at 37° C. helps to overcome the low transformation efficiency of plasmid DNA into this bacterium and chromosomal integrants in the population were readily identified when the plasmid was eliminated by growth at 50-55° C.

Metabolic Evolution

Metabolic evolution was carried out by sequentially subculturing in small pH-controlled fermenters under indicated conditions. Sequential transfers (2% inoculum; v/v) were made every 1-3 days, as growth permitted.

Enzyme Assays

Cultures were grown (LB-glucose medium in pH-controlled fermenters) to mid-exponential phase, harvested, and used for enzyme assays as previously described (23). Glycerol dehydrogenase from strain QZ19 was purified using differential ammonium sulfate precipitation followed by anion-exchange and hydrophobic interaction chromatography. GlyDH and GlyDH* were also purified as N-terminal His-tagged enzymes (33). GlyDH and LDH were assayed using standard methods (34, 35).

Analytical Methods

Glucose and fermentation products were determined by HPLC as previously described (36). Optical isomers of D-(-)- and L-(+)-lactic acids were determined by HPLC (Chirex 31266(D)-penicillamine column; 150×4.6 mm, 5 micron; Phenomenex) using 2 mM $CuSO_4$ as mobile phase, and enzymatically using D-lactate dehydrogenase (Sigma Chemical Co., St. Louis, Mo.).

Lactate Dehydrogenase Genes in B. coagulans

B. coagulans strain P4-102B typically produces L-lactate with low (15, 17) or undetectable level of the D-isomer (Table 1). Using the annotated genome sequence of a related B. coagulans strain 36D1 (GenBank Accession number CP003056) as a guide, homologous genes encoding both L-lactate dehydrogenase (ldh) and D-lactate dehydrogenase (ldhA) activities in strain P4-102B were amplified by PCR and confirmed by sequencing. The gene encoding D-lactate dehydrogenase in strain P4-102B was also identified by its ability to suppress anaerobic growth defect of an E. coli mutant (ldhA, pflB) followed by sequencing the corresponding cloned ldhA gene. With appropriate deletions to block competing pathways (FIG. 1), this organism has the potential to produce either D(-)-lactate or L(+)-lactate using only native genes.

Figure 6A:
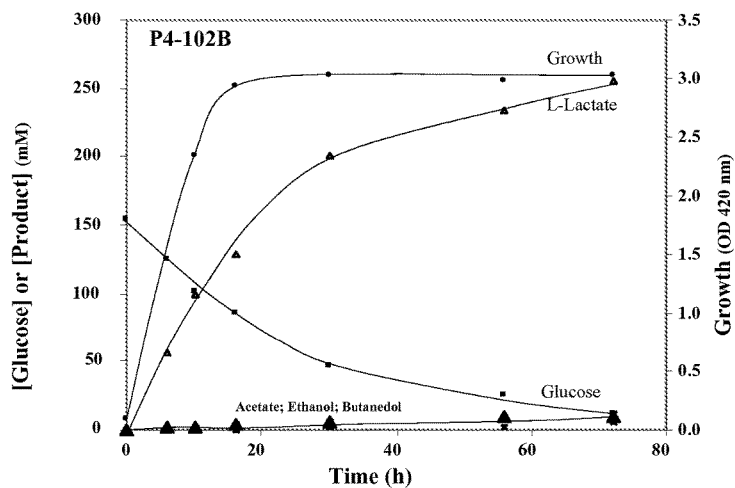
FIGS. 6A, 6B, 6C. Fermentation profile of *B. coagulans* wild type P4-102B (FIG. 6A) and its ldh (strain QZ4, FIG. 6B), and ldh, als (strain QZ5, FIG. 6C) mutants. Fermentations were at 50° C. in small fermenters with pH control at 5.0 by automatic addition of KOH in LB+glucose (0.16M).
Figure 6B:
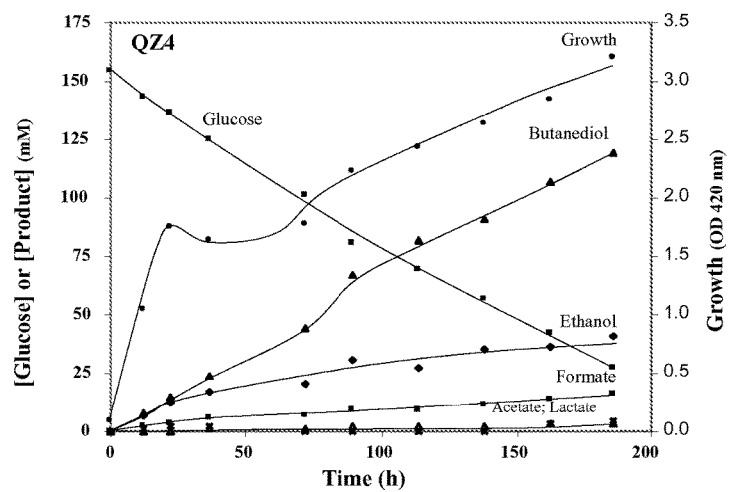
Figure 6C:
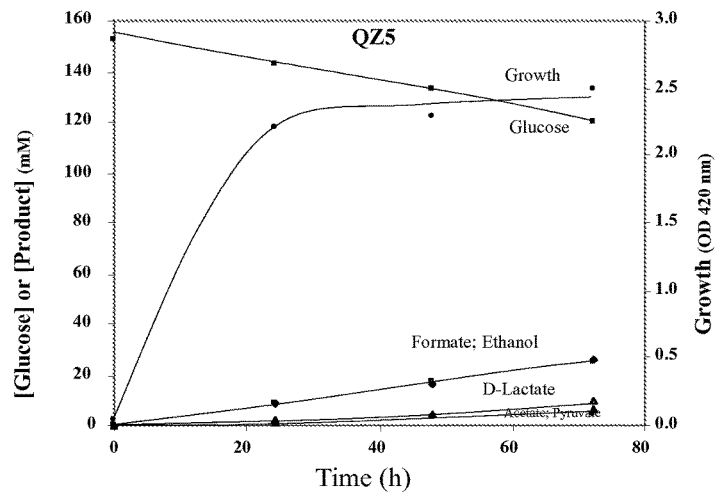

Deletion of Native L-(+)-Lactate Dehydrogenase (ldh) and Acetolactate Synthase (alsS) Genes B. coagulans strain P4-102B produced L-lactic acid as the primary fermentation product at pH 5.0 (Table 1; FIG. 6) together with small amounts of acetate and ethanol. Deletion of the ldh gene encoding L-(+)-lactate dehydrogenase (L-LDH) (strain QZ4) using methods developed for B. coagulans eliminated the primary route for NADH oxidation, slowing growth and sugar metabolism. However, production of 2,3-butanediol was increased dramatically with only a small increase in D(-)-lactate (Table 1; FIG. 6). At pH 7.0, the primary product of fermentation was ethanol as seen previously with an ldh mutant of a related strain 36D1 (23).

Strain QZ4 was further modified by deleting acetolactate synthase (alsS), essential for 2,3-butanediol production (FIG. 1). The resulting strain (QZ5) metabolized glucose rapidly at pH 7.0 with ethanol, acetate and formate as primary products (Table 1). In this strain and at this pH, pyruvate flux to D-lactate was only about 5% of the total. However, strain QZ5 did not grow anaerobically when cultured at pH 5.0 in the same medium. Fermentation profiles of strain QZ5 at pH 5.0 were determined by starting cultures with air in the gas phase to support growth. Depletion of $O_2$ in the medium, due to increasing cell density, initiated and maintained anaerobic metabolism of the bacterium. The specific rate of glucose consumption by strain QZ5 at pH 5.0 during the $O_2$-limited phase (0.9 mmoles $h^{-1}$ g cells$^{-1}$) was about 15% of the pH 7.0 culture (5.9 mmoles $h^{-1}$ g cells$^{-1}$) under similar conditions. The 6-fold lower specific glucose consumption rate and formate titer (Table 1) suggest that pyruvate formate-lyase (PFL) activity limits anaerobic growth of strain QZ5 at pH 5.0. Strain QZ5 also had higher D-LDH activity and a corresponding increase in ldhA mRNA as compared to strain QZ4 (Table 2). However, the D(-)-lactate titer was only about 10 mM in the QZ5 broth irrespective of the culture pH with yields of <0.15 lactate per glucose metabolized (theoretical yield of 2 per glucose).

Since the double mutant produced significant amounts of formate and other products of PFL activity, a triple mutant lacking PFL was constructed. However, this triple mutant lacking L-LDH, ALS and PFL activities failed to grow anaerobically under all conditions tested and was not investigated further.

Growth-Based Selection Increased D(-)-Lactate Production

Sugar metabolism, ATP production and anaerobic growth are apparently constrained in strain QZ5, especially at pH 5.0, by inadequate routes for NADH oxidation (Table 1; FIG. 1). Increasing the level of D(-)-lactate produced by strain QZ5 is expected to restore anaerobic growth of the double mutant to a level similar to that of the parent during L(+)-lactate production. Growth-based metabolic evolution is a powerful tool for selection of advantageous mutations (24) but this requires design of appropriate selection. Since strain QZ5 produced low levels of PFL activity at pH 5.0, as determined by the relative concentration of formate in the broth (Table 1), metabolic evolution of this strain for anaerobic growth at this pH offers a route to co-select increased production of D-lactate.

Figure 7:
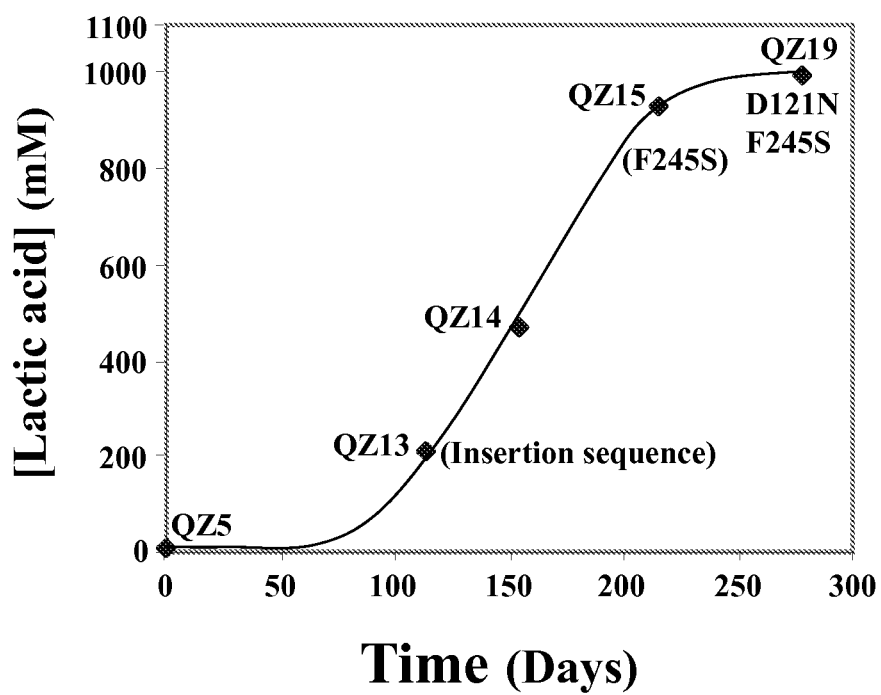
FIG. 7. Metabolic evolution of *B. coagulans* strain QZ5 to D-lactate producing strain QZ19 in small fermenters. Lactic acid titer during metabolic evolution was determined every three days. See text for other details.

Metabolic evolution of strain QZ5 at pH 5.0 for higher cell yield in LB+glucose fermentation yielded a derivative with improved growth after 113 days of selection. Cell yield of this strain (QZ13) was higher than the wild type, with a 20-fold increase in D-(-)-lactate production (Table 1; FIG. 7). To further increase the D-lactate yield and titer, strain QZ13 was further evolved at pH 7.0 in LB+glucose fermentations with $CaCO_3$. Addition of $CaCO_3$ to the medium was previously shown to overcome lactate inhibition of B. coagulans fermentation and permit titers approaching 2M in fed-batch fermentations (22). Since solid $CaCO_3$ buffered the medium better at pH 7.0 than at pH 5.0, further metabolic evolutions were at this higher pH. After 42 days of selection, strain QZ14 was isolated and tested. With strain QZ14, D(-)-lactate represented over 90% of the total fermentation products with a yield of 88% of the fermented glucose (Table 1).

Figure 2:
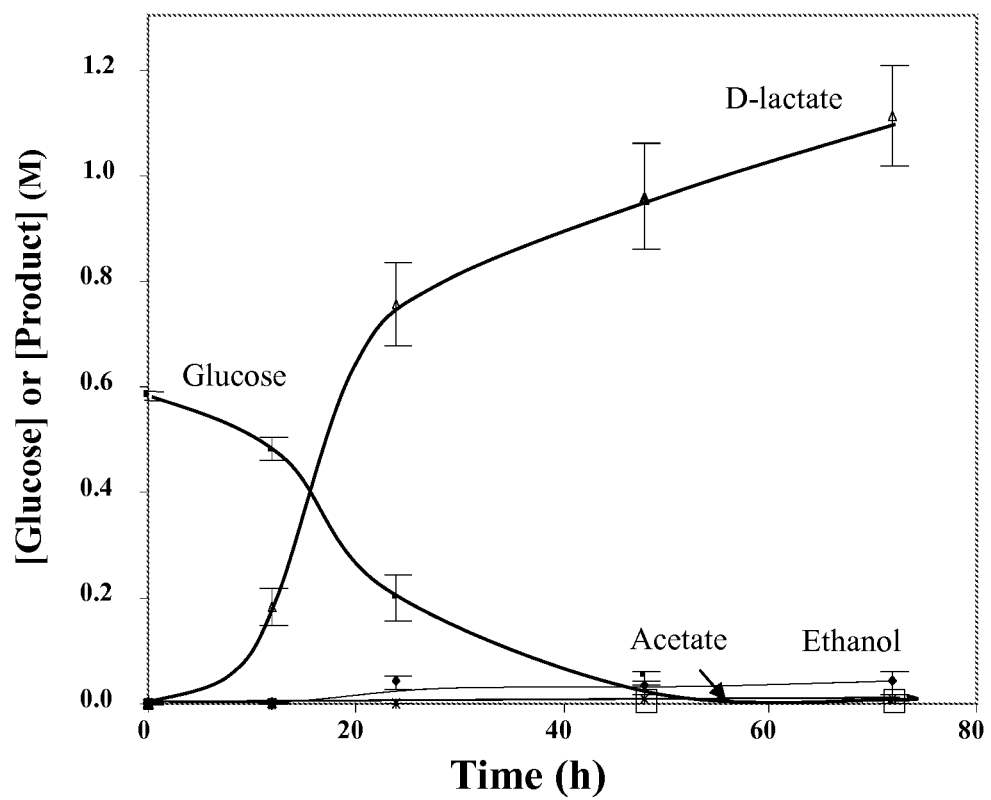
FIG. 2. Fermentation profile of D-lactate producing *B. coagulans* strain QZ19. Glucose concentration for the fermentation at 50° C. was 110 g $L^{-1}$ (0.6M) and the medium pH at 5.0 was maintained by addition of $Ca(OH)_2$.
Figure 8:
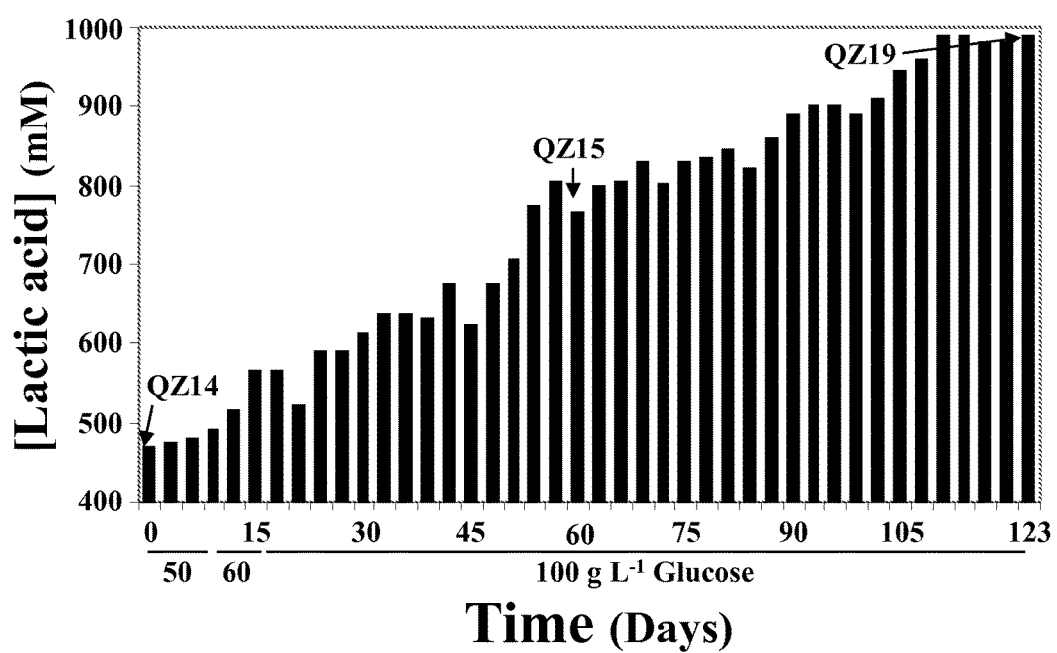
FIG. 8. Metabolic evolution of *B. coagulans* strain QZ14 in small fermenters in LB+glucose at pH 7.0 with increasing glucose concentration. Medium also contained 0.2M CaCO$_3$. Starting glucose concentration was 50 g L$^{-1}$ (0.28M). After the third transfer, glucose concentration was increased to 60 g L$^{-1}$ (0.33M). Glucose concentration of the medium was 100 g (0.56M) after the fifth transfer. Lactic acid titer of the culture was determined after 3 days of each transfer. After 60 days of incubation, strain QZ15 that produced about 0.8 M lactic acid was isolated. Strain QZ19 was isolated after an additional 63 days of metabolic evolution.

Strain QZ15 was isolated after an additional 60 days of serial transfers at pH 7.0 with increasing glucose concentrations (FIGS. 7 and 8). The D(-)-lactic acid titer of strain QZ15 at pH 7.0 was close to 1 M in 72 hours (Table 1). Continued metabolic evolution of strain QZ15 using 100 g $L^{-1}$ (0.56 M) glucose led to further increase in glucose flux to lactic acid. Strain QZ19 was isolated after 63 days of transfer (FIG. 8) and this strain produced about 1.0 M D(-)-lactate in less than 48 hours at pH 7.0 (Table 1). Fermentation of glucose by strain QZ19 at pH 5.0 started after a short lag with a titer of 1.1 M lactate in 72 hours (FIG. 2). Formate was not detected in the fermentation broth of strains QZ15 and QZ19 producing high levels of lactate. Formate is an indicator of PFL activity since these strains lack formate hydrogen-lyase activity. The small amount of ethanol and acetate (<5% of glucose carbon) produced by strain QZ19 is probably derived from acetyl-CoA produced by the pyruvate dehydrogenase complex (25).

These results show that deletion of the ldh and alsS genes combined with metabolic evolution led to alteration of the primary fermentation product of B. coagulans from L(+)-lactate to D(-)-lactate. Although the pfl genes are still present and transcribed in strain QZ19 at levels that are comparable to that of strain QZ4 (about 1.2 ng $ml^{-1}$ of total RNA), glucose flux through PFL was minimal as seen by the absence of formate in the fermentation broth. This is apparently a consequence of increasing metabolic flux to D-lactate that supplanted any pyruvate flux through PFL to acetyl-CoA during growth-based selection (Table 1).

Fermentation Characteristics of D-Lactate Producing Strain QZ19

Figure 9:
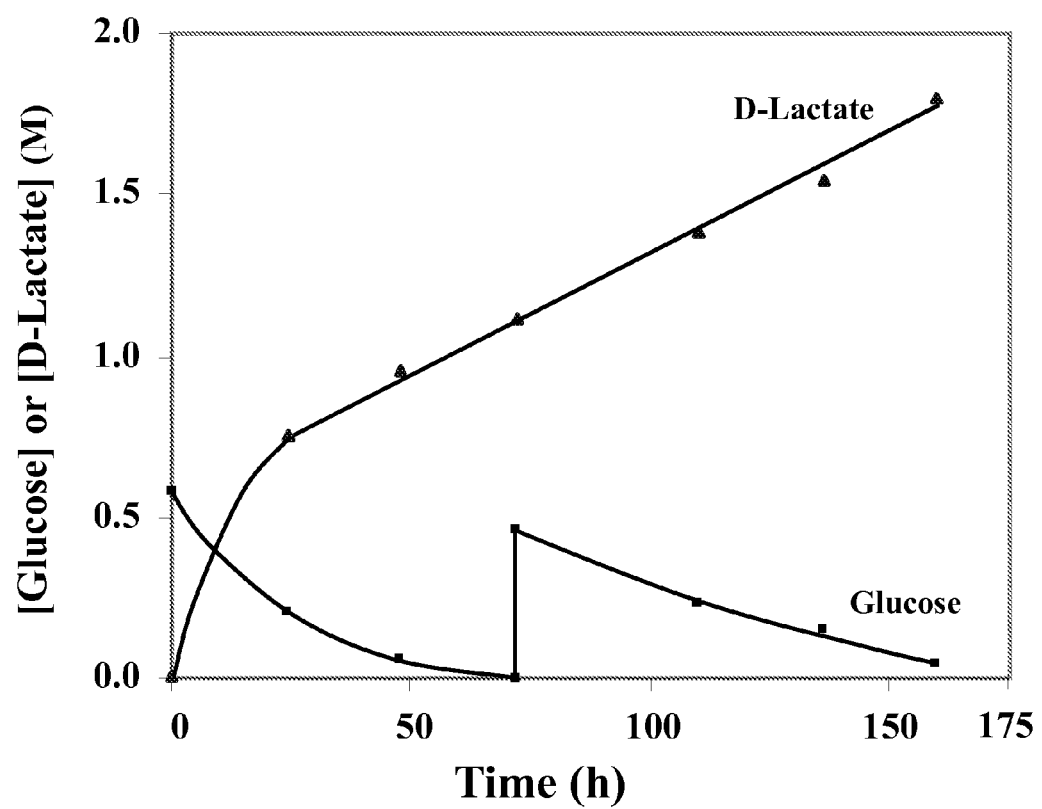
FIG. 9. Fed-batch fermentation of glucose to D-lactic acid by *B. coagulans* strain QZ19, at pH 5.0 and 50° C. Fermentations with pH control in LB+glucose were started with 100 g (0.56M) of glucose and at 72 hours, another 100 g L$^{-1}$ (0.56M) of glucose was added. Culture pH was maintained at 5.0 by Ca(OH)$_2$ addition.
Figure 10:
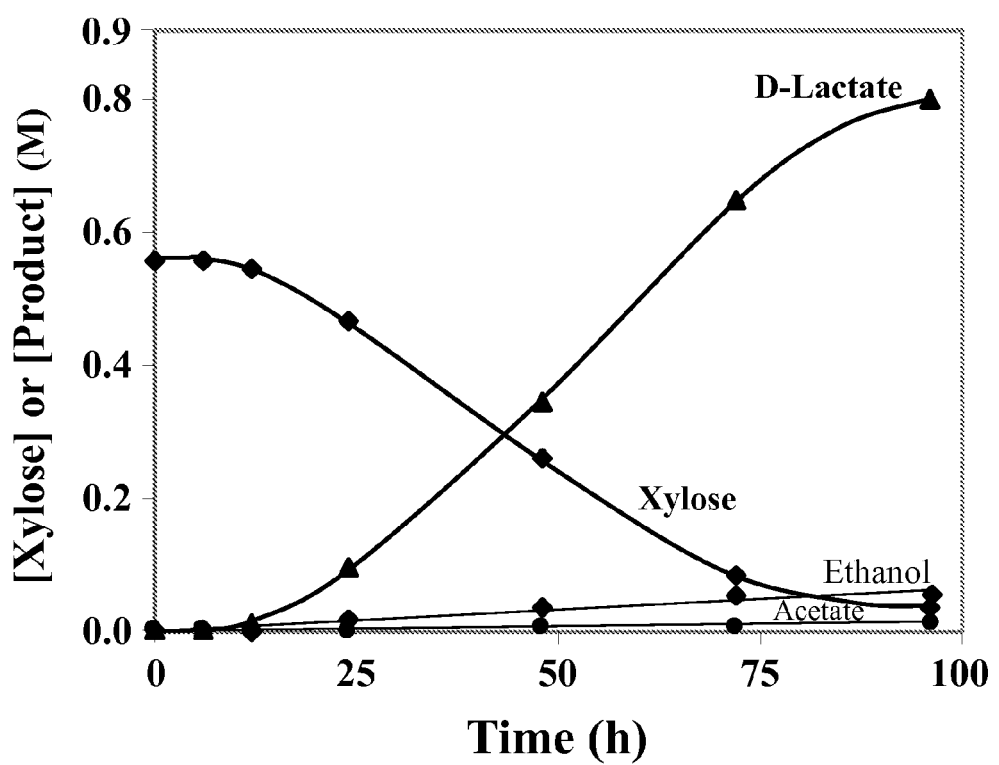
FIG. 10. Fermentation of xylose to D-lactic acid by *B. coagulans* strain QZ19 at 50° C. and pH 5.0. LB medium contained 80 g (0.53M) of xylose and 0.2 M CaCO$_3$.

Strain QZ19 produced close to 2M D-lactate in a fed-batch fermentation of glucose at pH 5.0 (FIG. 9). In such a fed-batch fermentation, the first 100 g L$^{-1}$ (0.56 M) of glucose was fermented in about 50 hours and fermentation of the second 100 g L$^{-1}$ (0.56 M) of glucose required an additional 72 hours, although the rate of lactate production was linear during this phase. Strain QZ19 also fermented xylose to D-lactic acid after a short lag. Approximately 80 g L$^{-1}$ (0.53 M) of xylose was converted to D(−)-lactate in 72 hours at 90% yield by weight (FIG. 10).

Simultaneous Saccharification and Fermentation (SSF) of Cellulose to D-Lactic Acid by Strain QZ19

Figure 3:
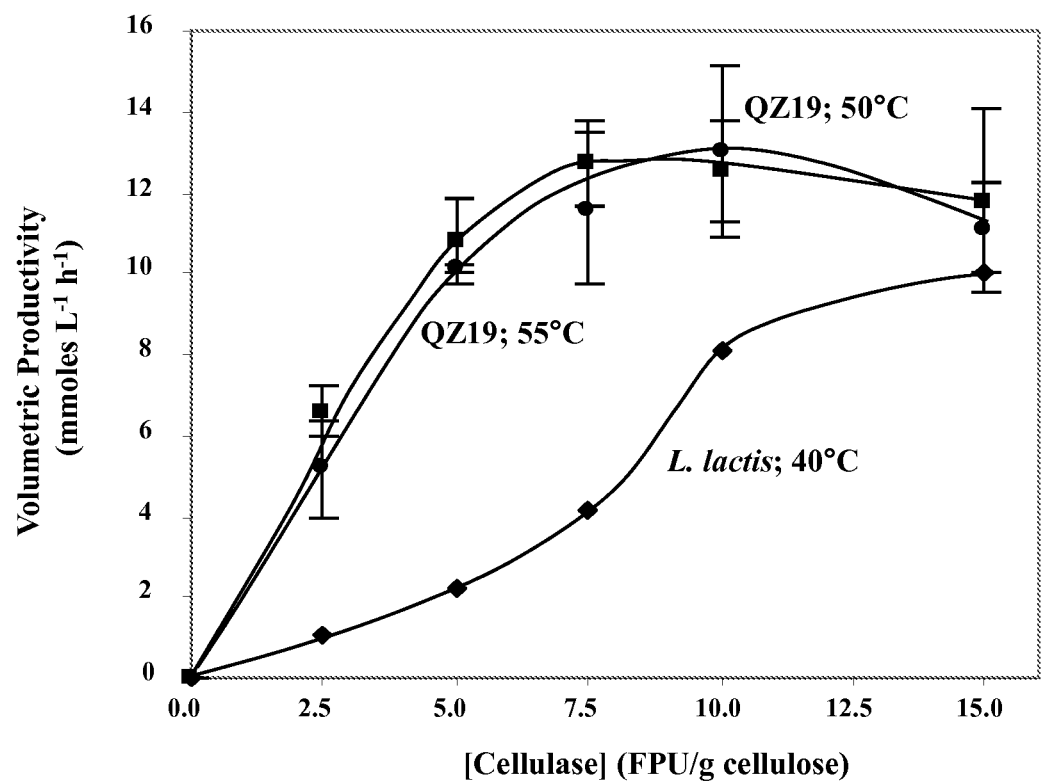
FIG. 3. Simultaneous saccharification and fermentation of crystalline cellulose to D-lactic acid by *B. coagulans* strain QZ19 at 50° C., pH 5.0. *Lactococcus lactis* data was from Ou et al. (22) and included for comparison. Initial cellulose (Solka Floc) concentration was 40 g L$^{-1}$.

One of the advantages of using *B. coagulans* as a microbial biocatalyst for lactic acid production is to lower the cellulase enzyme loading in SSF of cellulose to lactic acid due to its higher operating temperature and lower pH that match the optimum for commercial cellulase activity (50° C. and pH 5.0) (14, 15). Strain QZ19 reached the highest volumetric productivity for D-lactate with crystalline cellulose as feedstock at about 7.5 FPU (g cellulose)$^{-1}$ (FIG. 3) With this enzyme loading, the productivity of a typical lactic acid bacterium *Lactococcus lactis* at 40° C. was only 1/3 that of strain QZ19. These results are in agreement with previous studies on lower cellulase requirements for optimal L-lactate production by unmodified *B. coagulans* compared to other lactic acid bacteria (21). Strain QZ19 is better suited for SSF of cellulose to D-lactate and requires significantly lower levels of cellulase for cost-effective metabolism of this non-food carbohydrate.

Identification of Glycerol Dehydrogenase as the Source of D(−)-LDH Activity in Strain QZ19

Cell-free extracts of strain QZ19 had D(−)-lactate dehydrogenase activity (0.2 unit per mg protein) while the wild-type *B. coagulans* had no detectable D-LDH activity (Table 2). An observed 30-fold increase in D-LDH activity in strain QZ19 compared to strain QZ5 did not correlate with the 1.3-fold increase in the mRNA of the ldhA gene identified as encoding D-LDH. To identify potential mutation(s) in the D-LDH protein that could be responsible for the unusually high D-lactate dehydrogenase activity, the ldhA and flanking DNA from strains P4-102B and QZ19 were sequenced. However, both sequences were identical, indicating that ldhA-encoded D-LDH is not responsible for the large increase in D(−)-lactate production in strain QZ19. Only a single copy of ldhA was also found in the chromosome of strains QZ19 and P4-102B, eliminating gene duplication as a potential basis for D(−)-lactate production. This conclusion was further supported by comparable ldhA mRNA levels of strain QZ19 and its pre-evolution parent, strain QZ5 (Table 2). Higher levels of ldhA mRNA in these strains compared to the wild type could be responsible for the small amount of D(−)-lactate produced by strain QZ5 and other evolved strains, but do not explain the high D-lactate titer and yield observed with strain QZ19. The highest level of ldhA mRNA (D-LDH) in strain QZ19 was only about 10% of the level of ldh mRNA encoding L(+)-LDH, the primary fermentation route in the parent (FIG. 1; Table 2). These results suggest that another enzyme with D-LDH activity is present in strain QZ19, contributing to high D-lactate titer.

Figure 4:
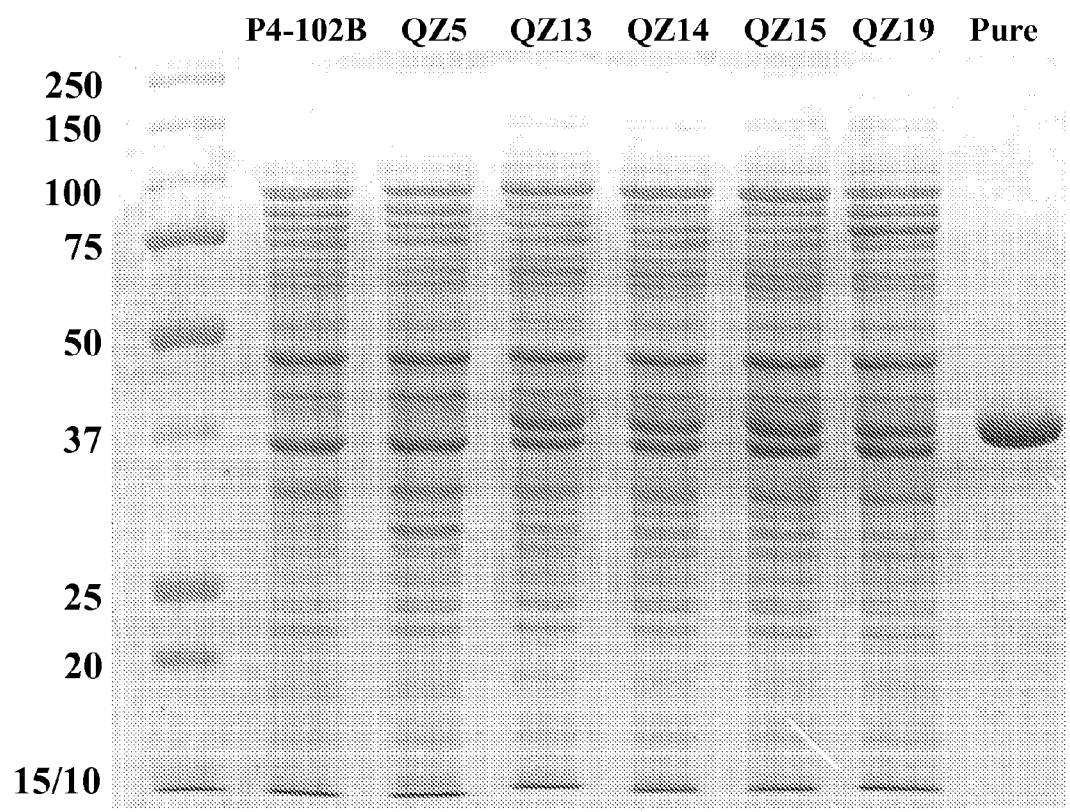
FIG. 4. SDS-PAGE of proteins from the crude extracts of various *B. coagulans* strains on the path to D-lactic acid producing strain QZ19. Cultures grown in LB+glucose (30 g L$^{-1}$) in pH-controlled (5.0) fermentations were harvested during mid- to late-exponential phase of growth and cell extracts were prepared and analyzed. Left lane, molecular weight standards. Numbers on the left represent the corresponding molecular mass of the proteins in kilodaltons. Right lane, pure GlyDH* from strain QZ19.

Cell-free extracts from strain QZ13 through QZ19 contained an abundant protein (apparent molecular mass of 37 KDa) that was absent in the wild-type strain P4-102B and in the pre-evolution strain QZ5 (FIG. 4). This protein was calculated to represent 11% of the total proteins in the extract of these strains. A protein with D-LDH activity was purified from strain QZ19. The size of this purified protein, 37 KDa, was comparable to the new abundant protein found in the evolved strains. After trypsin digestion of the protein with D-LDH activity, the fragments were separated by LC-MS/MS and identified. Of the 22 peptides generated, 9 were identical to predicted tryptic peptides from a protein in the *B. coagulans* strain 36D1 genome (Bcoa_1919; Accession number AEP01106.1) that was identified as glycerol dehydrogenase (gldA) by comparative sequence analysis (26) (FIG. 11). Based on the gldA gene sequence of *B. coagulans* strain 36D1, the gldA genes of strains P4-102B and QZ19 were amplified, cloned and sequenced. The gldA gene from strain QZ19 had two mutations compared to the native gene: G361A and T734C. These two mutations led to amino acid changes, D121N and F245S; the allele is designated as gldA101 and the protein as GlyDH* (FIG. 12). In addition to these two mutations in the coding region, a 1,821 bp DNA fragment was found to be inserted upstream of −62 ("A" in ATG as +1) of the gldA gene in QZ19 (FIG. 5). Two ORFs were identified within this insert (103 and 232 amino acids in length), both with similarity to a putative transposase (ISLhe15) from *Lactobacillus helveticus* strain H10 (25% identity and 48% similarity) (27).

The purified protein from strain QZ19 corresponding to the 37 KDa protein in the SDS-PAGE gel had both glycerol oxidation and pyruvate reduction activities. The GDH activity (glycerol oxidation to dihydroxyacetone) was 1.2 units (μmole min$^{-1}$) per mg protein and the pyruvate reduction to D-lactate activity was 0.8 unit per mg protein. The native enzyme purified from recombinant *E. coli* had a GlyDH activity of 7.1 units and an LDH activity of 0.01 unit per mg protein. These results suggest that a GlyDH in the *B. coagulans* genome acquired D-LDH activity through two mutations during the metabolic evolution of strain QZ19. The high level of expression of this protein apparently resulted from the upstream transposon insertion.

GlyDH* from Strain QZ19 Produced D-LDH Activity in *E. coli*

To confirm that the gldA101 allele in strain QZ19 encodes D-LDH activity, the gene was cloned from strain QZ19 (plasmid pQZ115) and introduced into *E. coli* strain AH242. *E. coli* strain AH242 is anaerobic minus due to mutations in ldhA and pflB that abolished the ability to oxidize NADH produced during glycolysis (25). Anaerobic growth of strain AH242 was restored by plasmid pQZ115 with D(−)-lactate as the fermentation product. Strain AH242 carrying plasmid pQZ109 that lacks the C-terminal 10 amino acids of the GlyDH* did not grow anaerobically, indicating that the truncated form of this protein lacks D-LDH activity. These results establish that GlyDH* from *B. coagulans* strain QZ19 has D(−)-LDH activity.

To further confirm that the gldA101 from strain QZ19 encodes a protein with D-LDH activity, the gene was cloned from strain QZ19 (plasmid pQZ113) and expressed in recombinant *E. coli* with N-terminal His-tag for protein purification. The recombinant GlyDH* also had both GlyDH and D-LDH activities. The specific activity of the enzyme with glycerol and NAD$^+$ was 0.68 unit per mg protein. With pyruvate and NADH as substrates (LDH reaction), the specific activity of the protein was an unexpectedly high 6.9 units per mg protein and the reaction product was identified as D-lactic acid by HPLC. In the reverse reaction, the enzyme was active only with D(−)-lactate and NAD$^+$ as substrates (specific activity of 0.17 unit per mg protein). Activity with L(+)-lactate as substrate was undetectable.

These results show that during metabolic evolution of strain QZ5, the native GlyDH acquired D-LDH activity. Native GlyDH from *B. stearothermophilus* has been reported to lack LDH activity (28) and in agreement with this, the LDH activity of *B. coagulans* native GlyDH purified from recombinant *E. coli* had less than 0.15% of the GlyDH activity.

Boosting gldA Transcription by Insertion of DNA in the D-Lactate Producing Strains In addition to evolution of the enzyme as D-LDH, the level of expression of gldA101 in strain QZ19 was the highest of the genes analyzed in this study (Table 2). This increase in transcription is apparently due to the 1,821 bp DNA insertion upstream of the gldA101 gene contributing a strong promoter for gldA101 expression in the evolved strain (FIG. 5).

Although consensus sequences corresponding to Shine-Dalgarno (GGAG) and −10 region (TATGAT) can be identified in the upstream DNA of gldA gene of the wild type, a corresponding −35 region could not be discerned. An inverted repeat with a 6 base pair stem and 11 base pair loop was found at the projected −35 region, suggesting that expression of this gene is only moderate, at best, in the native bacterium. Insertion of the 1,821 bp sequence in the upstream region of the gldA gene in strain QZ19 introduced a consensus −35 sequence to the gldA gene (FIG. 5). The high level of expression of the gldA gene and GDH* protein in strain QZ19 (Table 2) is apparently due to this reconstruction of the gldA upstream region in strain QZ13 and its derivatives yielding a strong promoter.

Evolutionary Path to D-Lactate Production in Strain QZ19

There are apparently three seminal events that occurred in the evolutionary path of *B. coagulans* strain QZ5 to strain QZ19 that produced over 90 g of D-lactate in about 48 hours: two mutations in the GlyDH (D121N and F245S) and the change in the promoter structure of gldA101 by insertion. DNA sequence analysis of the various intermediate strains in the evolutionary path revealed that the transposon DNA insertion occurred first in strain QZ13. This is in agreement with the elevated levels of gldA mRNA and GlyDH activity in strain QZ13 (about 100-fold and 50-fold, respectively, over the levels of strain QZ5) and other derivatives of this strain (Table 2). The higher GlyDH activity in strain QZ13 also led to a slight increase in D-LDH activity. However, the ratio of D-LDH to GlyDH activity in this strain was only 0.003, suggesting that the GlyDH still lacks significant D-LDH activity. The first GlyDH mutation (F245 S) was detected in strain QZ15 after the increase in transcription of gldA and this mutation apparently increased D-LDH/GlyDH ratio by about 7-fold to 0.02 (Table 2). The second mutation (D121N) occurred during the evolution of strain QZ19 from strain QZ15 and this second mutation increased the D-LDH/GlyDH ratio by about 10-fold to 0.22. It is interesting to note that with the increase in D-LDH activity, the enzyme lost part of its GlyDH activity. A 10-fold increase in D-LDH activity of the enzyme due to the two mutations (QZ19 vs QZ14) in strain QZ19 lowered the GlyDH activity by about 7-fold from that of strain QZ14 (Table 2). This loss in GlyDH activity in the extracts of strain QZ19 is apparently not due to lower protein levels in the cell since this protein band still accounted for about 11% of the total proteins (FIG. 4).

The mutations in the GlyDH of strain QZ19 occurred in two of nine critical amino acids forming a deep pocket where the nicotinamide ring of $NAD^+$ binds in the enzyme from *B. stearothermophilus* (29). A model of the GlyDH of *B. coagulans* also shows the deep cleft between the two domains of the enzyme with the mutated amino acids in the edge (FIG. 13). Glycerol C1 and C3 are reported to be stabilized in the *B. stearothermophilus* GlyDH by van der Walls interactions with the benzyl ring of Phe247. Changing the corresponding Phe245 of *B. coagulans* GlyDH to serine is expected to abolish this interaction, resulting in the observed reduction in glycerol oxidation activity of the enzyme from strain QZ19. The Asn121 and Ser245 probably stabilize pyruvate at the active site through their interactions with C1 and C2 of pyruvate (FIG. 13), resulting in the observed LDH activity.

These results show that an increase in the expression level of gldA and acquisition of D-LDH activity by the GlyDH through two mutations are responsible for the increase in D-lactate titer of *B. coagulans* strain QZ19 fermentations (Table 1).

Biochemical Properties of the Native and Various Mutated Forms of Glycerol Dehydrogenase from *B. coagulans*

Figure 15:
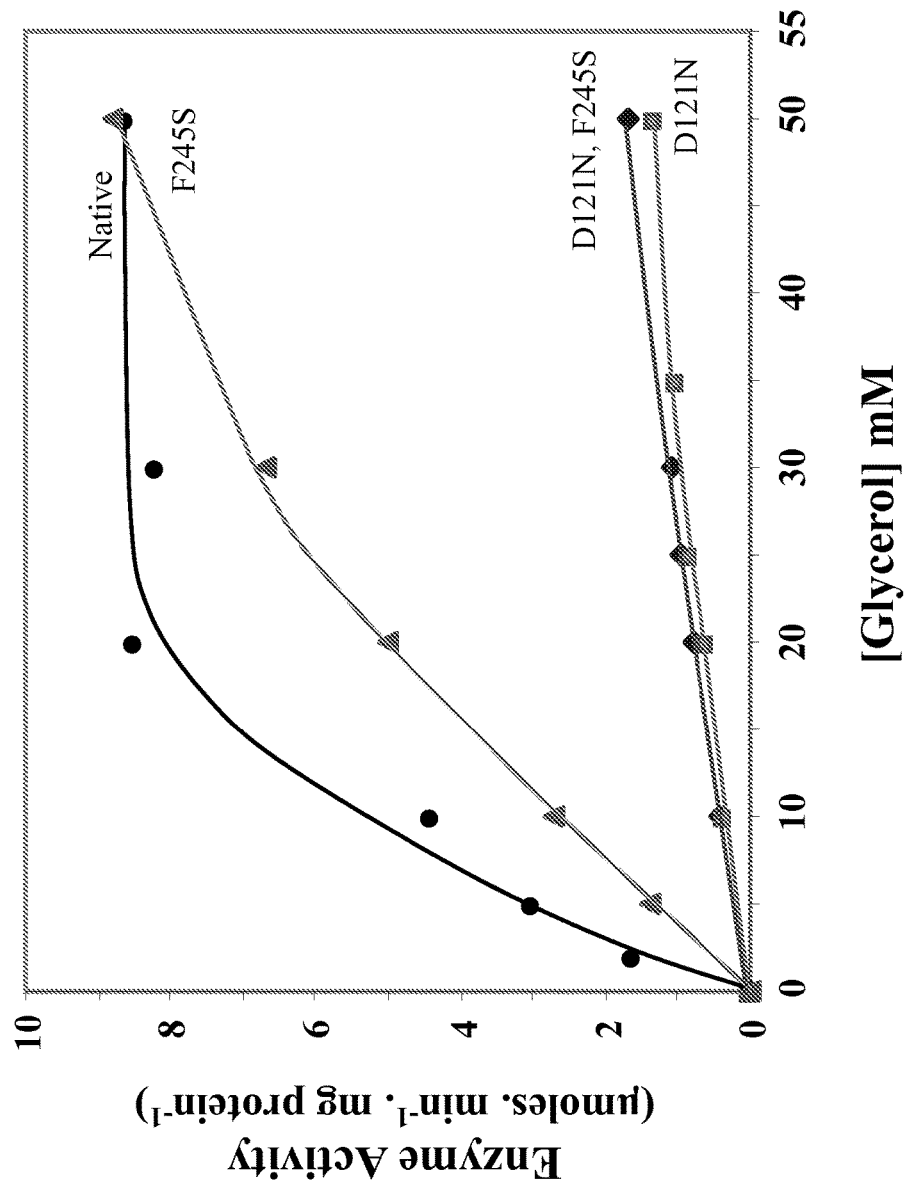
FIG. 15. Glycerol dehydrogenase activity of native protein and altered forms of the enzyme obtained during growth-based selection of *B. coagulans* for D-lactic acid production.

During the development of a D-lactate producing *B. coagulans* derivative (strain QZ19), a glycerol dehydrogenase (GDH) with two mutations (D121N and F245S) evolved to catalyze the reduction of pyruvate to D-lactate (Table 1 and FIG. 7). The first derivative that produced a significant D-lactate titer, strain QZ15, carried a single mutation that changed the amino acid phenylalanine at position 245 to serine. As strain QZ15 was further selected for higher lactate productivity, the GDH protein acquired a second mutation in amino acid position 121 (D121N) (FIG. 15). Combination of these two mutations led strain QZ19 to produce D-lactic acid at a titer close to 100 g/L in 48 hours at pH 5.0 and 50° C. in pH-controlled fermentations. In order to evaluate the role of each of these two mutations in the catalysis of pyruvate reduction to D-lactate, GDH/LDH enzyme with either of the two substitutions (D121N or F245S) and the protein with both changes were expressed in *E. coli*, purified, and their biochemical properties were determined.

Figure 16:
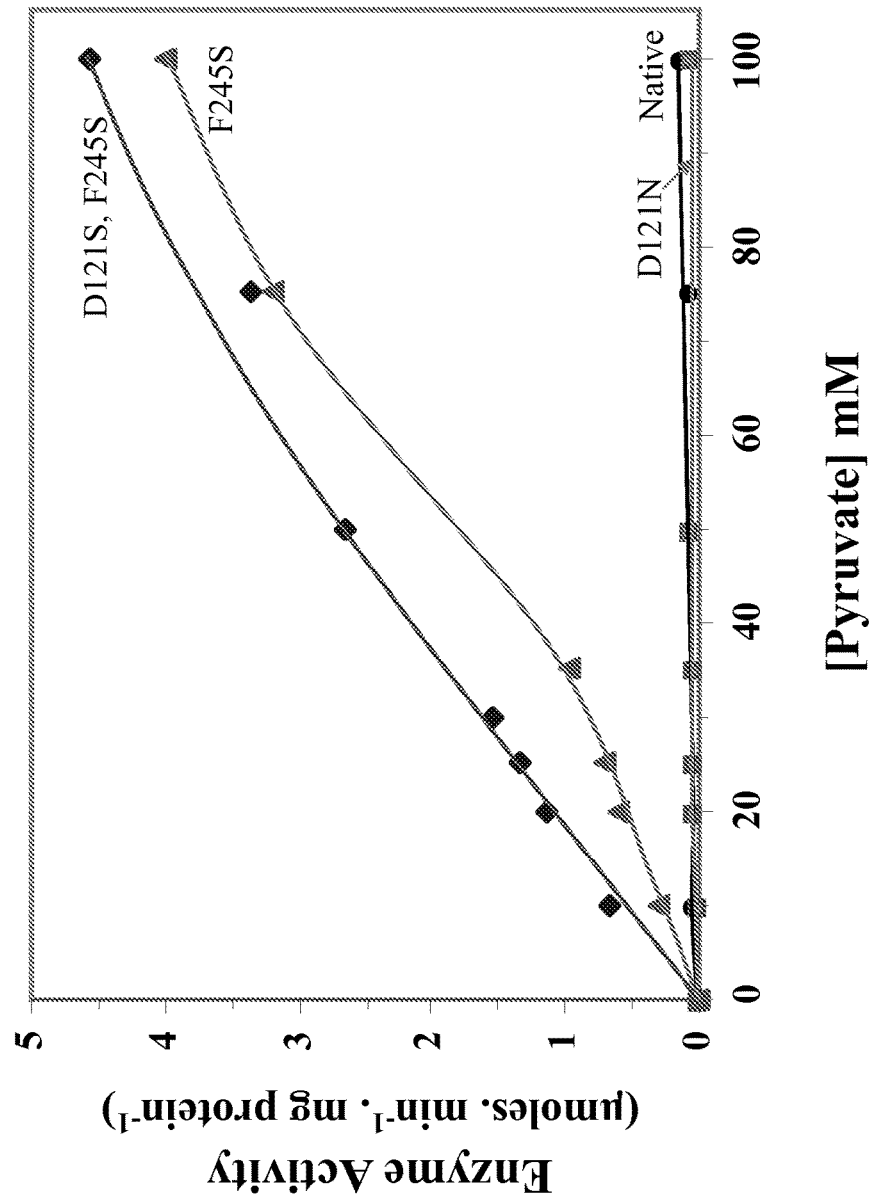
FIG. 16. Lactate dehydrogenase activity of native protein and altered forms of the enzyme obtained during growth-based selection of *B. coagulans* for D-lactic acid production.

The native GDH oxidized glycerol at a specific activity of about 22.5 units (µmole $min^{-1}$ mg $protein^{-1}$) at 55° C. (Table 5). The specific activity of this enzyme increased from about 8.6 units at room temperature to the 22.5 units at the optimum temperature for activity of 55° C., which is also the optimum growth temperature for *B. coagulans*. The GDH activity of the native enzyme saturated at about 20 mM glycerol which is in agreement with an apparent Km for this enzyme of 11.7 mM glycerol (FIG. 16; Table 6).

The native enzyme also oxidized several other substrates (Table 5). Although the levels of activity with ethane-1,2-diol and propane-1,2-diol are significantly lower than the activity with glycerol, specific activity with 2,3-butanediol was almost 2 times higher than the rate of glycerol oxidation. 1,2-butanediol and 1,3-butanediol also served as substrates for the native enzyme. These results suggest that the GDH enzyme from *B. coagulans* has broader substrate specificity. Although this enzyme exhibited pyruvate reduction activity (D-LDH), this activity was less than 1.5% of the glycerol oxidation activity (LDH to GDH activity ratio of 0.013). In addition to reducing pyruvate, this enzyme also had a very low but detectable level of 2-ketobutyric acid reduction (to 2-hydroxybutyric acid) activity. The low pyruvate reduction activity of this enzyme could be attributed to the very high apparent Km for pyruvate (1M; about 100-fold higher than that for glycerol) (Table 6). The native enzyme is about 1,000 times more efficient at oxidizing glycerol with $NAD^+$ as an electron acceptor than reducing pyruvate using NADH.

*B. coagulans* strain QZ15, a derivative of strain QZ5, fermented glucose at 55° C. and produced about 80 g/L D-lactic acid in about 72 hours. The GDH in this strain carries an amino acid change, phenylalanine to serine, at position 245 (FIG. 7). This change significantly altered the ratio of LDH to GDH to 0.16 from that of 0.01 for the native enzyme with minimal reduction in GDH activity (Table 5; FIG. 15). In addition to gaining significant pyruvate reduction activity (LDH) (FIG. 16), this F245S form of the enzyme also had higher activity with 1,2-propanediol and 1,2-butanediol as substrates compared to the native enzyme (Table 5). These differences in the GDH and LDH activities of the F245S enzyme could be attributed to an increase in apparent Km for glycerol (78.6 mM compared to the value of 11.7 for the native enzyme) and a reduction in apparent Km for pyruvate (0.23 M vs 1.0 M for the native enzyme) (Table 6).

Further growth- and fermentation-based selection of *B. coagulans* strain QZ15 led to strain QZ19, which produced close to 100 g/L D-lactic acid in about 48 hours at pH 5.0 and 55° C. The GDH enzyme from this strain carries a second alteration, D121N, in addition to the F245S. GDH with this change alone had significantly lower activity with glycerol and other diols tested (Table 5). A slight increase in apparent Km for glycerol could not explain this almost 7-fold reduction in specific activity (Table 6). Although the D121N mutation decreased the glycerol oxidation activity, this change had no detectable effect on pyruvate reduction activity (D-LDH) of the enzyme that was comparable to that of the native enzyme.

The negative effect of the D121N mutation on the oxidation of glycerol and other diols is retained even when this mutation was introduced into the F245S form of the enzyme. The enzyme with both alterations (F245S and D121N) had an LDH/GDH activity ratio of about 1.8 compared to the value of 0.01 for the native enzyme (Table 5). The D121N mutation also lowered the apparent Km for pyruvate from 231 mM for the enzyme with the F245S mutation alone to 51 mM for the enzyme with both changes (Table 6), probably the primary cause of the higher catalytic efficiency with pyruvate as substrate. These results show that both these changes are essential for the enzyme to function as a D-LDH in strain QZ19 developed for D-LDH production. The F245S mutation increased the D-LDH activity of the enzyme while the D121N mutation greatly lowered the GDH activity of the protein that further enhanced the D-LDH activity.

Based on the crystal structure of a GDH from *Geobacillus stearothermophilus* (29) that is 47% identical to the *B. coagulans* GDH amino acid sequence, the aspartate at position 121 forms a hydrogen bond with the oxygen in the C2 position of glycerol. This secondary alcohol (H—C—OH) at the C2 position of glycerol is the one that is oxidized to a C=O in the oxidation of glycerol to dihydroxyacetone. Changing this aspartate to asparagine apparently minimized this interaction with the substrate glycerol. In addition, the phenylalanine at 245 is expected to interact with the C1 and C3 of glycerol while the C2-O is interacting with D121. Replacing the phenylalanine with serine could minimize this interaction of the enzyme with the substrate glycerol and this could account for the higher observed apparent Km in these altered forms of the enzymes. However, these observations do not predict that the F245S alone or with D121N would support interaction of the GDH enzyme with pyruvate as a substrate and the altered enzyme would function as a D-LDH.

These results suggest that the native enzyme is indeed a polyol dehydrogenase with broad substrate specificity. The higher activity of the F245S enzyme with various short-chain diols coupled with their thermophilic characteristics (optimum of 55° C.) makes these enzymes useful in bioconversion of various diols and polyols to corresponding ketones with stereoselectivity. For example, 1,3-butanediol can be oxidized to 4-hydroxy-2-butanone, a potential pharmaceutical intermediate of commercial interest, which is currently produced by the chemical industry.

TABLE 1

Fermentation profiles of *B. coagulans* derivatives on the path to D(−)-lactic acid production at 50° C.

| Strain | Genotype | Culture pH | Cell Yield | Glucose Consumed (mM) | Qs* | L(+)- Lactate | D(−) Lactate | Pyruvate | Acetate | Succ | Formate | Ethanol | Yield† Lactate | Total |
|---|---|---|---|---|---|---|---|---|---|---|---|---|---|---|
| P4-102B | wild type | 5.0 | 3.0 | 144.3 | 5.7 | 255.6 | UD | UD | 5.7 | 0.6 | UD | 10.5 | 0.89 | 1.00 |
|  |  | 7.0 | 7.1 | 188.6 | 18.4 | 336.4 | UD | UD | 15.9 | 0.4 | UD | 4.6 | 0.89 | 0.96 |
| QZ4‡ | Δldh | 5.0 | 1.8 | 53.8 | 0.8 | UD | 1.0 | UD | UD | 1.0 | 6.5 | 20.3 | 0.01 | 1.03 |
|  |  | 7.0 | 8.1 | 226.0 | 4.3 | UD | 9.7 | UD | 42.3 | 6.7 | 90.6 | 224.5 | 0.02 | 1.17 |
| QZ5 | Δldh Δ alsD | 5.0 | 2.5 | 32.8 | 0.5 | UD | 9.8 | 4.5 | 4.6 | 0.1 | 25.3 | 25.6 | 0.15 | 0.72 |
|  |  | 7.0 | 5.8 | 152.5 | 6.8 | UD | 12.8 | 10.1 | 95.4 | 2.1 | 154.6 | 164.5 | 0.04 | 0.94 |
| QZ13 | Evolved§ | 5.0 | 4.3 | 128.8 | 2.4 | UD | 212.4 | 6.1 | 2.7 | 0.6 | 24.3 | 23.4 | 0.82 | 0.95 |
|  |  | 7.0 | 6.0 | 162.6 | 4.0 | UD | 219.8 | 9.3 | 14.8 | 0.4 | 66.9 | 58.1 | 0.68 | 0.93 |
| QZ14 | Evolved§ | 7.0 | ND¶ | 265.7 | 5.4 | UD | 468.4 | 1.6 | UD | 1.3 | 21.5 | 28.4 | 0.88 | 0.93 |
| QZ15 | Evolved§ | 7.0 | ND¶ | 562.6 | 17.0 | UD | 928.2 | UD | 22.6 | 8.1 | UD | 97.5 | 0.83 | 0.94 |
| QZ19 | Evolved§ | 5.0‖ | ND | 580.0 | 12.5 | UD | 1,108.1 | UD | 10.2 | UD | UD | 40.9 | 0.96 | 1.00 |
|  |  | 7.0 | ND¶ | 590.0 | 19.4 | UD | 993.0 | UD | 45.3 | 5.7 | UD | 84.2 | 0.84 | 0.96 |

All fermentations were in LB medium with glucose and the reported values were after 72 h, unless indicated otherwise. Cell yield is expressed in OD420 nm.

*Qs, rate of glucose consumption - mmoles glucose consumed $L^{-1}$ $h^{-1}$.

†Product yield is presented as a fraction of theoretical yield from glucose (for lactate, the theoretical yield is 2 per glucose).

‡Strain QZ4 also produced acetoin and 2,3-butanediol; pH 5.0 culture, 44.5 mM 2,3-butanediol; pH 7.0 culture, 31.6 mM acetoin and 93.1 mM 2,3-butanediol. These two products were not detected in the broths from other cultures.

§Evolved, various stages in evolution (FIG. 7).

¶Due to the presence of $CaCO_3$ in the medium, the cell density of these cultures was not determined.

‖Fermentation pH was maintained by addition of $Ca(OH)_2$ and cell density was not determined due to the presence of Ca-salts.

UD—undetectable, less than 0.5 mM; Succ, succinate.

TABLE 2

Enzyme and mRNA levels of *B. coagulans* strains during evolution for high level of D-lactate production

| Strain | Genotype | mRNA level | | | Enzyme Activity | | Ratio |
|---|---|---|---|---|---|---|---|
| | | ldh | gldA | ldhA | GlyDH | D-LDH | D-LDH/GlyDH |
| P4-102B | Wild type | 61.90 | 1.13 | 0.12 | 0.19 | <0.001 | <0.005 |
| QZ4 | Δldh | 0.02 | 1.29 | 1.08 | 0.13 | 0.002 | 0.015 |
| QZ5 | Δldh, ΔalsS | UD | 1.51 | 4.87 | 0.13 | 0.007 | 0.050 |
| QZ13 | Evolution | UD | 148.50 | 3.62 | 7.06 | 0.028 | 0.003 |
| QZ14 | Evolution | UD | 175.20 | 3.77 | 7.12 | 0.021 | 0.003 |
| QZ15 | Evolution | UD | 176.70 | 5.12 | 5.60 | 0.112 | 0.020 |
| QZ19 | Evolution | UD | 243.50 | 6.12 | 1.01 | 0.221 | 0.219 |

All cultures were grown in pH-controlled fermentations in LB + glucose (30 g/L) at pH 5.0. mRNA levels are ng ml$^{-1}$ of total RNA. ldh and ldhA represent the mRNA encoding L-LDH and D-LDH, respectively. gldA, glycerol dehydrogenase mRNA.
Enzyme activities were determined in cell extracts and expressed as µmoles min$^{-1}$ mg protein$^{-1}$.
UD—Undetectable, <0.01 ng ml$^{-1}$ of total RNA.

TABLE 3

Bacterial strains and plasmids used in this study

| | Relevant genotype | Source or Reference |
|---|---|---|
| Strain | | |
| *B. coagulans* P4-102B | Wild type | (17) |
| *E. coli* Top 10 | mcrA Δ(mrr-hsdRMS-mcrBC) φ80lacZΔM15 ΔlacX74 nupG recA1 araD139 Δ(ara-leu)7697 galE15 galK16 rpsL(Str$^R$) endA1 | Invitrogen |
| *E. coli* AH242 | ΔldhA, Δ(focA-pflB) | (25) |
| *B. subtilis* HB1000 | SPβ2Δ 2::Tn917::pSK10Δ6 attSPβ | (37) |
| QZ3 | P4-102B ldh::pQZA4, Em$^R$ | This work |
| QZ4 | QZ3 Δldh | This work |
| QZ5 | QZ4 ΔalsS | This work |
| QZ13 | QZ5 evolved at pH 5.0 for higher cell yield | This work |
| QZ14 | QZ13 evolved at pH 7.0 for higher lactic acid titer | This work |
| QZ15 | QZ14 evolved for higher sugar use | This work |
| QZ19 | QZ15 further evolved for higher rate of lactate production. | This work |
| Plasmid | | |
| pGK12 | Broad host-range, Cm$^R$, Em$^R$ | (38) |
| pUC19 | Plasmid vector Ap$^R$ | Lab stock |
| pQZ44 | pGK12 with promoterless ldh (P4-102B) with 100 bp deletion | This work |
| pQZ45 | pUC19 with P4-102B alsSD | This work |
| PQZ45-1 | pUC19 with 2,380 bp promoterless P4-102B alsSD | This work |
| pQZ54 | pQZ45-1 with 596 bp alsS deletion with Em$^R$ gene insertion | This work |
| pQZ64 | pGK12 with 506 bp alsS deletion with Em$^R$ gene insertion | This work |
| PQZ109 | pUC19 with 3,185 bp fragment from QZ19 with truncated gldA | This work |
| PQZ113 | pET15b with gldA from QZ19 | This work |
| PQZ115 | pUC19 with 3,422 bp fragment from QZ19 with gldA | This work |

TABLE 4

Primers used in this study

| Primer name | Sequence (5'-3') |
|---|---|
| Primer9 | ccc<u>tacgta</u>TTGGAACGGGTGCAGTTGGT (SEQ ID NO: 33) |
| Primer10 | ccc<u>gaattc</u>CCGGGTTGCTGGCAACAAGA (SEQ ID NO: 34) |
| Primer11 | ccc<u>gaattc</u>TTTGAGCGCCCAATTTGGAA (SEQ ID NO: 35) |
| Primer12 | ccc<u>aggcct</u>CCGGAACGCCAACGTACACA (SEQ ID NO: 36) |
| Primer17 | ACGAGCCGCTGACACTGGAT (SEQ ID NO: 37) |
| Primer18 | GCCGTCTTCGCCTTCGTTCA (SEQ ID NO: 38) |
| Primer21 | TGTCATAAGTCGCCGAACCG (SEQ ID NO: 39) |
| Primer22 | TGATTGTATGCCGCCACGAA (SEQ ID NO: 40) |
| Primer23 | GGTGTTGCAGAAGAGCTTGT (SEQ ID NO: 41) |
| Primer24 | GTGCCGCAATCGGAATAATC (SEQ ID NO: 42) |
| Primer29 | AGATCTTAAGCCGTGTGGAG (SEQ ID NO: 43) |

TABLE 4-continued

Primers used in this study

| Primer name | Sequence (5'-3') |
|---|---|
| Primer30 | CGCAACAATACTGCCGATTC (SEQ ID NO: 44) |
| Primer33 | TTGGAGGCGAACAAAGAACA (SEQ ID NO: 45) |
| Primer34 | CGGCAATGGAAAAAGAAATG (SEQ ID NO: 46) |
| Primer GDH10-R | AGTCCGACACTCAGGCAGAA (SEQ ID NO: 47) |
| Primer GDH11-F | GGCTTACCGTGCTCGAAGAA (SEQ ID NO: 48) |
| D-LDH-3 | GCGTTCTTCTGCTAACATCC (SEQ ID NO: 49) |
| GDH-6 | GTGCTCGCTTCCTATATCGT (SEQ ID NO: 50) |
| GDH-7 | gggctcgagATGACGAAAATCATTACCTC (SEQ ID NO: 51) |
| GDH-12 | gggggatccGTGCTCGCTTCCTATATCGT (SEQ ID NO: 52) |

Capital letters represent B. coagulans sequence. Lower case letters indicate the restriction enzyme recognition sequence and 5'extensions for optimum cleavage of the PCR-amplified product by the respective enzyme.

TABLE 5

Specific activity of B. coagulans GDH and its derivatives on various substrates

| | Specific Activity ($\mu$mole · min$^{-1}$ · mg protein$^{-1}$) | | | |
|---|---|---|---|---|
| Substrate | GDH | F245S | D121N | F245S D121N |
| Glycerol | 22.5 | 16.8 | 3.5 | 2.6 |
| Ethane-1,2-diol | 4.5 | 4.3 | 0.6 | 1.8 |
| Propane-1,2-diol | 4.3 | 45.2 | 2.9 | 8.4 |
| 2,3-butanediol | 46.1 | 68.0 | 1.1 | 9.0 |
| 1,2-butanediol | 4.7 | 42.9 | 6.6 | 10.5 |
| 1,3-butanediol | 10.8 | 4.0 | 3.0 | 0.6 |
| 1-butanol | UD | UD | UD | UD |
| 2-butanol | UD | UD | UD | UD |
| 1,4-butanediol | 0.2 | 0.2 | 0.01 | 0.03 |
| Pyruvate* | 0.3 | 2.70 | 0.2 | 4.6 |
| 2-ketobutyric acid* | 0.1 | 2.70 | 0.2 | 3.7 |
| Lactate* | UD | UD | UD | 1.8 |
| Malate* | 0.02 | UD | 0.1 | UD |
| LDH/GDH | 0.01 | 0.16 | 0.06 | 1.77 |

[Substrate], 100 mM; Temperature, 55° C.
*With pyruvate and 2-ketobutyric acid the forward reaction was monitored and with lactate and malate, the reverse reaction was followed.
UD, undetectable, less than 0.01 unit of activity.

TABLE 6

Kinetic properties of native and mutated forms of Glycerol dehydrogenase of B. coagulans

| Substrate | Native | F245S | D121N | S245S, D121N |
|---|---|---|---|---|
| | Km(nM) | | | |
| Glycerol | 11.7 | 78.6 | 132.5 | 141.4 |
| Pyruvate | 1,030.0 | 231.0 | 683.0 | 51.4 |
| NAD$^+$ | 0.6 | 0.6 | 0.2 | 0.4 |
| NADH | 0.4 | 0.4 | 0.4 | 0.5 |
| D-lactate | ND | ND | 243.0 | 72.9 |
| | Kcat (s$^{-1}$) | | | |
| Glycerol | 28.0 | 62.5 | 13.2 | 16.7 |
| Pyruvate | 3.3 | 19.5 | 2.0 | 35.5 |
| D-lactate | ND | ND | 1.9 | 14.5 |

TABLE 6-continued

Kinetic properties of native and mutated forms of Glycerol dehydrogenase of B. coagulans

| Substrate | Native | F245S | D121N | S245S, D121N |
|---|---|---|---|---|
| | Kcat/Km (s$^{-1}$ · mM$^{-1}$) | | | |
| Glycerol | 2.4 | 0.8 | 0.1 | 0.1 |
| Pyruvate | 0.003 | 0.08 | 0.003 | 0.7 |
| D-lactate | ND | ND | 0.008 | 0.2 |

Kinetic properties were determined using glycerol oxidation, pyruvate reduction or lactate oxidation reactions at 55° C.
ND, not determined due to low activity.

REFERENCES

1. Demain, A L (2009) Biosolutions to the energy problem. J. Ind. Microbiol. Biotechnol. 36:319-332.
2. Lynd, L R, Laser, M S, Bransby, D, Dale, B E, Davison, B, Hamilton, R, Himmel, M, Keller, M, McMillan, J D, Sheehan, J, Wyman, C E (2008) How biotech can transform biofuels. Nature Biotechnol. 26:169-172.
3. Mecking, S (2004) Nature or petrochemistry?-biologically degradable materials. Angew. Chem. Int. Ed. 43:1078-1085.
4. Ragauskas, A J, Williams, C K, Davison, B H, Britovsek, G, Cairney, J, Eckert, C A, Frederick, W J, Jr., Hallett, J P, Leak, D J, Liotta, C L, Mielenz, J R, Murphy, R, Templer, R, Tschaplinski, T (2006) The path forward for biofuels and biomaterials. Science 311:484-489.
5. Chen, G-Q (2009) A microbial polyhydroxyalkanoates (PHA) based bio- and materials industry. Chem. Soc. Rev. 38:2434-2446.
6. Benninga, H (1990) A history of lactic acid making (Kluyver Academic Publishers, Dordrecht, the Netherlands).
7. Datta, R, Henry, M (2006) Lactic acid: recent advances in products, processes and technologies—a review. J. Chem. Technol. Biotechnol. 81:1119-1129.
8. Hofvendahl, K, Hans-Hagerdal, B (2000) Factors affecting the fermentative lactic acid production from renewable resources. Enz. Microb. Technol. 26:87-107.
9. Tsuji, H (2005) Poly(lactide) stereocomplexes: formation, structure, properties, degradation, and applications. Macromol. Biosci. 5:569-597.

10. Teusink, B, Smid, E J (2006) Modelling strategies for the industrial exploitation of lactic acid bacteria. *Nature Rev. Microbiol.* 4:46-56.
11. Grabar, T B, Zhou, S, Shanmugam, K T, Yomano, L P, Ingram, L O (2006) Methylglyoxal bypass identified as source of chiral contamination in L(+) and D(−)-lactate fermentations by recombinant *Escherichia coli*. *Biotechnol. Lett.* 28:1527-1535.
12. Zhou, S, Shanmugam, K T, Yomano, L P, Grabar, T B, Ingram, L O (2006) Fermentation of 12% (w/v) glucose to 1.2 M lactate by *Escherichia coli* strain SZ194 using mineral salts medium. *Biotechnol. Lett.* 28:663-670.
13. Tenenbaum, D J (2008) Food vs. fuel: Diversion of crops could cause more hunger. *Environ. Health Perspect.* 116: A254-A257.
14. Iyer, Pv, Lee, Y Y (1999) Product inhibition in simultaneous saccharification and fermentation of cellulose into lactic acid. *Biotechnol. Letters* 21:371-373.
15. Patel, M A, Ou, M, Ingram, L O, Shanmugam, K T (2005) Simultaneous saccharification and co-fermentation of crystalline cellulose and sugar cane bagasse hemicellulose hydrolysate to lactate by a thermotolerant acidophilic *Bacillus* sp. *Biotech. Prog.* 21:1453-1460.
16. Garde, A, Jonsson, G, Schmidt, A S, Ahring, B K (2002) Lactic acid production from wheat straw hemicellulose hydrolysate by *Lactobacillus pentosus* and *Lactobacillus brevis*. *Bioresource Technol* 81:217-23.
17. Patel, M A, Ou, M S, Harbrucker, R, Aldrich, H C, Buszko, M L, Ingram, L O, Shanmugam, K T (2006) Isolation and characterization of acid-tolerant, thermophilic bacteria for effective fermentation of biomass-derived sugars to lactic acid. *Appl. Environ. Microbiol.* 72:3228-3235.
18. Tanaka, K, Komiyama, A, Sonomoto, K, Ishizaki, A, Hall, S J, Stanbury, P E (2002) Two different pathways for D-xylose metabolism and the effect of xylose concentration on the yield coefficient of L-lactate in mixed-acid fermentation by the lactic acid bacterium *Lactococcus lactis* 10-1. *Appl. Microbiol. Biotechnol.* 60:160-167.
19. Okano, K, Yoshida, S, Yamada, R, Tanaka, T, Ogino, C, Fukuda, H, Kondo, A (2009) Improved production of homo-D-lactic acid via xylose fermentation by introduction of xylose assimilation genes and redirection of the phosphoketolase pathway to the pentose phosphate pathway in L-Lactate dehydrogenase gene-deficient *Lactobacillus plantarum*. *Appl. Environ. Microbiol.* 75:7858-7861.
20. Jarboe, L R, Zhang, X, Wang, X, Moore, J C, Shanmugam, K T, Ingram, L O (2010) Metabolic engineering for production of biorenewable fuels and chemicals: contributions of synthetic biology. *J. Biomed. Biotechnol.* 2010:ID 761042.
21. Ou, M S, Mohammed, N, Ingram, L O, Shanmugam, K T (2009) Thermophilic *Bacillus coagulans* requires less cellulases for simultaneous saccharification and fermentation of cellulose to products than mesophilic microbial biocatalysts. *Appl. Biochem. Biotechnol.* 155:379-385.
22. Ou, M S, Ingram, L O, Shanmugam, K T (2011) L: (+)-Lactic acid production from non-food carbohydrates by thermotolerant *Bacillus coagulans*. *J. Ind. Microbiol. Biotechnol.* 38:599-605.
23. Su, Y, Rhee, M S, Ingram, L O, Shanmugam, K T (2010) Physiological and fermentation properties of *Bacillus coagulans* and a mutant lacking fermentative lactate dehydrogenase activity. *J. Ind. Microbiol. Biotechnol.* 38:441-450.
24. Turner, N J (2009) Directed evolution drives the next generation of biocatalysts. *Nature Chem. Biol.* 5:567-573.
25. Kim, Y, Ingram, L O, Shanmugam, K T (2007) Construction of an *Escherichia coli* K-12 mutant for homoethanologenic fermentation of glucose or xylose without foreign genes. *Appl. Environ. Microbiol.* 73:1766-1771.
26. Altschul, S F, Gish, W, Miller, W, Myers, E W, Lipman, D J (1990) Basic local alignment search tool. *J. Mol. Biol.* 215:403-410.
27. Zhang, H, Zhao, W, Chen, Y, Sun, Z, Sun, T, Meng, H (2010) Complete genome sequence of *Lactobacillus helveticus* strain H10. GenBank Acc. No. CP002429.1.
28. Spencer, P, Bown, K J, Scawen, M D, Atkinson, T, Gore, M G (1989) Isolation and characterisation of the glycerol dehydrogenase from *Bacillus stearothermophilus*. *Biochim. Biophys. Acta* 994:270-279.
29. Ruzheinikov, S N, Burke, J, Sedelnikova, S, Baker, P J, Taylor, R, Bullough, P A, Muir, N M, Gore, M G, Rice, D W (2001) Glycerol dehydrogenase. structure, specificity, and mechanism of a family III polyol dehydrogenase. *Structure* 9:789-802.
30. Kok, J, van der Vossen, J M, Venema, G (1984) Construction of plasmid cloning vectors for lactic streptococci which also replicate in *Bacillus subtilis* and *Escherichia coli*. *Appl. Environ. Microbiol.* 48:726-731.
31. Luchansky, J B, Muriana, P M, Klaenhammer, T R (1988) Application of electroporation for transfer of plasmid DNA to *Lactobacillus, Lactococcus, Leuconostoc, Listeria, Pediococcus, Bacillus, Staphylococcus, Enterococcus* and *Propionibacterium*. *Mol. Microbiol.* 2:637-646.
32. Hamilton, C M, Aldea, M, Washburn, B K, Babitzke, P, Kushner, S R (1989) New method for generating deletions and gene replacements in *Escherichia coli*. *J. Bacteriol.* 171:4617-4622.
33. Kim, Y, Ingram, L O, Shanmugam, K T (2008) Dihydrolipoamide dehydrogenase mutation alters the NADH sensitivity of pyruvate dehydrogenase complex of *Escherichia coli* K-12. *J. Bacteriol.* 190:3851-3858.
34. Lin, E C, Magasanik, B (1960) The activation of glycerol dehydrogenase from Aerobacter *aerogenes* by monovalent cations. *J. Biol. Chem.* 235:1820-1823.
35. Yoshida, A, Freese, E (1975) Lactate dehydrogenase from *Bacillus subtilis*. *Meth. Enzymol.* 41:304-309.
36. Underwood, S A, Zhou, S, Causey, T B, Yomano, L P, Shanmugam, K T, Ingram, L O (2002) Genetic changes to optimize carbon partitioning between ethanol and biosynthesis in ethanologenic *Escherichia coli*. *Appl. Environ. Microbiol.* 68:6263-6272.
37. Fredrick, K, Helmann, J D (1996) FlgM is a primary regulator of sigmaD activity, and its absence restores motility to a sinR mutant. *J. Bacteriol.* 178:7010-7013.

We claim:

1. An isolated polypeptide comprising the sequence of a glycerol dehydrogenase selected from SEQ ID NOs: 5-32 in which a phenylalanine has been substituted with an amino acid selected from serine, threonine, glycine or asparagine and, optionally, an aspartic acid has been substituted with an amino acid selected from glutamine or asparagine, wherein said phenylalanine corresponds to the phenylalanine at position 245 of SEQ ID NO: 5 and said aspartic acid corresponds to the aspartic acid at position 121 of SEQ ID NO: 5, and wherein the isolated polypeptide has D-lactate dehydrogenase activity.

2. The isolated polypeptide according to claim 1, wherein said polypeptide comprises SEQ ID NO: 1.

3. The isolated polypeptide according to claim 1, wherein said polypeptide comprises the sequence of a glycerol dehydrogenase selected from SEQ ID NOs: 5-32 in which a phenylalanine has been substituted with an amino acid selected from serine, threonine, glycine or asparagine and an aspartic acid has been substituted with an amino acid selected from glutamine or asparagine, wherein said phenylalanine corresponds to the phenylalanine at position 245 of SEQ ID NO: 5 and said aspartic acid corresponds to the aspartic acid at position 121 of SEQ ID NO: 5, and wherein the isolated polypeptide has D-lactate dehydrogenase activity.

4. The isolated polypeptide according to claim 1, wherein only the phenylalanine that corresponds to the phenylalanine at position 245 of SEQ ID NO: 5 has been substituted with an amino acid selected from serine, threonine, glycine or asparagine.

5. The isolated polypeptide according to claim 1, wherein said polypeptide comprises amino acid substitutions selected from:
   a) a phenylalanine corresponding to the phenylalanine at position 245 of SEQ ID NO: 5 has been substituted with serine and an aspartic acid corresponding to the aspartic acid at position 121 of SEQ ID NO: 5 has been substituted with glutamine;
   b) a phenylalanine corresponding to the phenylalanine at position 245 of SEQ ID NO: 5 has been substituted with threonine and an aspartic acid corresponding to the aspartic acid at position 121 of SEQ ID NO: 5 has been substituted with glutamine;
   c) a phenylalanine corresponding to the phenylalanine at position 245 of SEQ ID NO: 5 has been substituted with threonine and an aspartic acid corresponding to the aspartic acid at position 121 of SEQ ID NO: 5 has been substituted with asparagine;
   d) a phenylalanine corresponding to the phenylalanine at position 245 of SEQ ID NO: 5 has been substituted with glycine and an aspartic acid corresponding to the aspartic acid at position 121 of SEQ ID NO: 5 has been substituted with glutamine;

e) a phenylalanine corresponding to the phenylalanine at position 245 of SEQ ID NO: 5 has been substituted with glycine and an aspartic acid corresponding to the aspartic acid at position 121 of SEQ ID NO: 5 has been substituted with asparagine;

f) a phenylalanine corresponding to the phenylalanine at position 245 of SEQ ID NO: 5 has been substituted with asparagine and an aspartic acid corresponding to the aspartic acid at position 121 of SEQ ID NO: 5 has been substituted with glutamine;

g) a phenylalanine corresponding to the phenylalanine at position 245 of SEQ ID NO: 5 has been substituted with asparagine and an aspartic acid corresponding to the aspartic acid at position 121 of SEQ ID NO: 5 has been substituted with asparagine; and h) only a phenylalanine corresponding to the phenylalanine at position 245 of SEQ ID NO: 5 has been substituted with an amino acid selected from serine, threonine, glycine or asparagine in said polypeptide.

6. The isolated polypeptide according to claim 1, wherein said polypeptide consists of the sequence of the glycerol dehydrogenase with amino acid substitutions selected from:

a) a phenylalanine corresponding to the phenylalanine at position 245 of SEQ ID NO: 5 has been substituted with serine and an aspartic acid corresponding to the aspartic acid at position 121 of SEQ ID NO: 5 has been substituted with glutamine;

b) a phenylalanine corresponding to the phenylalanine at position 245 of SEQ ID NO: 5 has been substituted with threonine and an aspartic acid corresponding to the aspartic acid at position 121 of SEQ ID NO: 5 has been substituted with glutamine;

c) a phenylalanine corresponding to the phenylalanine at position 245 of SEQ ID NO: 5 has been substituted with threonine and an aspartic acid corresponding to the aspartic acid at position 121 of SEQ ID NO: 5 has been substituted with asparagine;

d) a phenylalanine corresponding to the phenylalanine at position 245 of SEQ ID NO: 5 has been substituted with glycine and an aspartic acid corresponding to the aspartic acid at position 121 of SEQ ID NO: 5 has been substituted with glutamine;

e) a phenylalanine corresponding to the phenylalanine at position 245 of SEQ ID NO: 5 has been substituted with glycine and an aspartic acid corresponding to the aspartic acid at position 121 of SEQ ID NO: 5 has been substituted with asparagine;

f) a phenylalanine corresponding to the phenylalanine at position 245 of SEQ ID NO: 5 has been substituted with asparagine and an aspartic acid corresponding to the aspartic acid at position 121 of SEQ ID NO: 5 has been substituted with glutamine;

g) a phenylalanine corresponding to the phenylalanine at position 245 of SEQ ID NO: 5 has been substituted with asparagine and an aspartic acid corresponding to the aspartic acid at position 121 of SEQ ID NO: 5 has been substituted with asparagine; and h) a phenylalanine corresponding to the phenylalanine at position 245 of SEQ ID NO: 5 has been substituted with an amino acid selected from serine, threonine, glycine or asparagine in said polypeptide.

7. A composition comprising a carrier and a polypeptide according to claim 1.

8. The composition according to claim 7, wherein said carrier comprises a hydrolysate derived from a biomass, a hemicellulosic biomass, a lignocellulosic biomass or a cellulosic biomass.

9. A composition comprising a diol and/or polyol and a polypeptide according to claim 1.

10. The composition according to claim 9, wherein the diol is 1,3-butanediol.

11. A method of producing 4-hydroxy-2-butanone comprising contacting 1,3-butanediol with a polypeptide according to claim 1 under conditions that result in the oxidation of 1,3-butanediol to 4-hydroxy-2-butanone.

12. An isolated nucleic acid comprising a polynucleotide encoding a polypeptide according to claim 1.

13. A vector or genetic construct comprising a polynucleotide according to claim 12.

14. An isolated microbial cell transformed with a nucleic acid according to claim 12.

15. The isolated microbial cell according to claim 14, wherein said microbial cell comprises a vector or genetic construct comprising said nucleic acid.

16. The isolated microbial cell according to claim 14, wherein said microbial cell is a Gram-negative or a Gram-positive bacterial cell.

17. The isolated microbial cell according to claim 16, wherein the Gram-negative bacterial cell is a bacterial cell selected from the genera of *Escherichia, Zymomonas, Acinetobacter, Gluconobacter, Geobacter, Shewanella, Salmonella, Enterobacter* or *Klebsiella* and the Gram-positive bacterial cell is a bacterial cell selected from the genera of *Bacillus, Clostridium, Corynebacteria, Lactobacillus, Lactococcus, Oenococcus, Streptococcus* and *Eubacteria*.

18. The isolated microbial cell according to claim 14, wherein the microbial cell is *Escherichia coli* or *Klebsiella oxytoca*.

19. The isolated microbial cell according to claim 14, wherein the microbial cell is selected from Thermoanaerobes, *Bacillus* spp., *Paenibacillus* spp. or *Geobacillus* spp.

20. The isolated microbial cell according to claim 14, wherein the microbial cell is a yeast cell selected from a *Candida, Hansenula, Kluyveromyces, Pichia, Saccharomyces, Schizosaccharomyces*, or *Yarrowia* cell.

21. The isolated microbial cell according to claim 20, wherein the yeast cell is *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica*.

22. The isolated microbial cell according to claim 14, wherein said microbial cell is a fungal cell selected from an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

23. The isolated microbial cell according to claim 22, wherein said fungal cell is an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense,*

*Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium* purpurogenum, *Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

24. A composition comprising culture medium and a transformed microbial cell according to claim 14.

25. The composition according to claim 24, wherein said culture medium comprises a hydrolysate derived from a biomass, a hemicellulosic biomass, a lignocellulosic biomass or a cellulosic biomass.

26. A method of making D-lactic acid comprising culturing a transformed microbial cell according to claim 14 in a culture medium under conditions that allow for the production of D-lactic acid.

27. The method according to claim 26, wherein said culture medium comprises a hydrolysate derived from a biomass, a hemicellulosic biomass, a lignocellulosic biomass or a cellulosic biomass.

* * * * *

UNITED STATES PATENT AND TRADEMARK OFFICE
CERTIFICATE OF CORRECTION

| | |
|---|---|
| PATENT NO. | : 9,745,556 B2 |
| APPLICATION NO. | : 14/347688 |
| DATED | : August 29, 2017 |
| INVENTOR(S) | : Qingzhao Wang, Keelnatham T. Shanmugam and Lonnie O'Neal Ingram |

It is certified that error appears in the above-identified patent and that said Letters Patent is hereby corrected as shown below:

Column 1,
Lines 14-19:
"This invention was made with government support awarded by Department of Energy (DE-FG36-04G014019 and DE-FG36-08G088142) and U.S. Department of Agriculture, National Institute of Food and Agriculture (2011-10006-30358). The government has certain rights in the invention."

Should read:
--This invention was made with government support under Grant No. DE-FG36-04GO14019 and DE-FG36-08GO88142 awarded by the United States Department of Energy and under Grant No. 2011-10006-30358 awarded by the United States Department of Agriculture. The government has certain rights in the invention.--

Signed and Sealed this
Ninth Day of January, 2018

Joseph Matal
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 56

<210> SEQ ID NO 1
<211> LENGTH: 367
<212> TYPE: PRT
<213> ORGANISM: Bacillus coagulans

<400> SEQUENCE: 1

```
Met Thr Lys Ile Ile Thr Ser Pro Ser Lys Phe Ile Gln Gly Pro Asp
1               5                   10                  15

Glu Leu Ser Arg Leu Ser Ala Tyr Thr Glu Arg Leu Gly Lys Lys Ala
            20                  25                  30

Phe Ile Ile Ala Asp Asp Phe Val Thr Gly Leu Val Gly Lys Thr Val
        35                  40                  45

Glu Glu Ser Tyr Ala Gly Lys Glu Thr Gly Tyr Gln Met Ala Leu Phe
    50                  55                  60

Gly Gly Glu Cys Ser Lys Pro Glu Ile Glu Arg Leu Cys Glu Met Ser
65                  70                  75                  80

Lys Ser Glu Glu Ala Asp Val Val Gly Ile Gly Gly Gly Lys Thr
                85                  90                  95

Leu Asp Thr Ala Lys Ala Val Gly Tyr Tyr Asn Asn Ile Pro Val Ile
            100                 105                 110

Val Ala Pro Thr Ile Ala Ser Thr Asn Ala Pro Thr Ser Ala Leu Ser
        115                 120                 125

Val Ile Tyr Lys Glu Asn Gly Glu Phe Glu Glu Tyr Leu Met Leu Pro
    130                 135                 140

Leu Asn Pro Thr Phe Val Ile Met Asp Thr Lys Val Ile Ala Ser Ala
145                 150                 155                 160

Pro Ala Arg Leu Leu Val Ser Gly Met Gly Asp Ala Leu Ala Thr Tyr
                165                 170                 175

Phe Glu Ala Arg Ala Thr Lys Arg Ala Asn Lys Thr Thr Met Ala Gly
            180                 185                 190

Gly Arg Val Thr Glu Ala Ala Ile Ala Leu Ala Lys Leu Cys Tyr Asp
        195                 200                 205

Thr Gln Ile Leu Glu Gly Leu Lys Ala Lys Leu Ala Ala Glu Lys His
    210                 215                 220

Leu Val Thr Glu Ala Val Glu Lys Ile Ile Glu Ala Asn Thr Tyr Leu
225                 230                 235                 240

Ser Gly Ile Gly Ser Glu Ser Gly Gly Leu Ala Ala His Ala Ile
                245                 250                 255

His Asn Gly Leu Thr Val Leu Glu Glu Thr His His Met Tyr His Gly
            260                 265                 270

Glu Lys Val Ala Phe Gly Thr Leu Ala Gln Leu Ile Leu Glu Asp Ala
        275                 280                 285

Pro Lys Ala Glu Ile Glu Glu Val Val Ser Phe Cys Leu Ser Val Gly
    290                 295                 300

Leu Pro Val Thr Leu Gly Asp Leu Gly Val Lys Glu Leu Asn Glu Glu
305                 310                 315                 320

Lys Leu Arg Lys Val Ala Glu Leu Ser Cys Ala Glu Gly Glu Thr Ile
                325                 330                 335

Tyr Asn Met Pro Phe Glu Val Thr Pro Asp Leu Val Tyr Ala Ala Ile
            340                 345                 350

Val Thr Ala Asp Ser Val Gly Arg Tyr Tyr Lys Glu Lys Trp Ala
        355                 360                 365
```

<210> SEQ ID NO 2
<211> LENGTH: 1104
<212> TYPE: DNA
<213> ORGANISM: Bacillus coagulans

<400> SEQUENCE: 2

```
atgacgaaaa tcattacctc tccaagcaag tttatacaag cccccgatga attgtccagg      60
ctttcggcgt atacggaaag gcttggcaaa aaagcattta ttattgcgga tgattttgtc     120
accggccttg tcggcaaaac ggttgaagaa agctatgccg gcaaagaaac ggggtatcaa     180
atggcattat tcggtggcga gtgttctaaa ccggaaatcg aacggctttg tgaaatgagc     240
aaatccgagg aagccgatgt cgttgtcgga atcggcggcg aaaaacatt ggataccgca      300
aaagcagtcg gtattacaa taacattccg gtgattgtcg cgccgaccat cgcttccacc      360
aatgccccga caagcgccct gtctgttatt tacaaagaga cggcgagtt tgaagaatac      420
ttgatgctgc cgctgaaccc gacttttgtc attatggata cgaaagtgat tgcctctgcc     480
cctgcccgcc tgctcgtttc cggcatggga gatgcgcttg cgacgtattt tgaagcgcgc     540
gccactaagc gggcaaataa aacgacgatg gcaggcgggc gtgttacgga agcggcgatc     600
gcgcttgcaa actttgtta tgacacgcaa atttttggaag gttaaaagc aaaactggca      660
gcggaaaaac atcttgttac ggaagcagtg gaaaaaatca ttgaagcgaa tacgtatctg     720
agcggaatcg gttctgaaag cggcggcctt gctgcgcac atgcgatcca taatgggctt     780
accgtgctcg aagaaaccca tcatatgtac cacggcgaaa agtggcatt cggtaccctc     840
gcccagctga ttttggaaga tgcgccgaaa gcggaaattg aagaggtggt ctccttctgc     900
ctgagtgtcg gacttcccgt cacgctcggg gatttgggcg tgaaagaact gaatgaggaa     960
aagctccgaa agtggctga actttcctgt gcggaaggcg aaacgattta taacatgccg    1020
tttgaagtca cgcctgacct tgtgtacgca gcaatcgtta ccgctgattc cgtcgggcgg    1080
tattataagg aaaaatgggc atga                                           1104
```

<210> SEQ ID NO 3
<211> LENGTH: 367
<212> TYPE: PRT
<213> ORGANISM: Bacillus coagulans
<220> FEATURE:
<221> NAME/KEY: MISC_FEATURE
<222> LOCATION: (121)..(121)
<223> OTHER INFORMATION: Xaa = Asp or Asn
<220> FEATURE:
<221> NAME/KEY: MISC_FEATURE
<222> LOCATION: (245)..(245)
<223> OTHER INFORMATION: Xaa = Phe or Ser

<400> SEQUENCE: 3

```
Met Thr Lys Ile Ile Thr Ser Pro Ser Lys Phe Ile Gln Gly Pro Asp
1               5                   10                  15

Glu Leu Ser Arg Leu Ser Ala Tyr Thr Glu Arg Leu Gly Lys Lys Ala
            20                  25                  30

Phe Ile Ile Ala Asp Asp Phe Val Thr Gly Leu Val Gly Lys Thr Val
        35                  40                  45

Glu Glu Ser Tyr Ala Gly Lys Glu Thr Gly Tyr Gln Met Ala Leu Phe
    50                  55                  60

Gly Gly Glu Cys Ser Lys Pro Glu Ile Glu Arg Leu Cys Glu Met Ser
65                  70                  75                  80

Lys Ser Glu Glu Ala Asp Val Val Val Gly Ile Gly Gly Gly Lys Thr
                85                  90                  95
```

```
Leu Asp Thr Ala Lys Ala Val Gly Tyr Tyr Asn Asn Ile Pro Val Ile
            100                 105                 110

Val Ala Pro Thr Ile Ala Ser Thr Xaa Ala Pro Thr Ser Ala Leu Ser
        115                 120                 125

Val Ile Tyr Lys Glu Asn Gly Glu Phe Glu Tyr Leu Met Leu Pro
    130                 135                 140

Leu Asn Pro Thr Phe Val Ile Met Asp Thr Lys Val Ile Ala Ser Ala
145                 150                 155                 160

Pro Ala Arg Leu Leu Val Ser Gly Met Gly Asp Ala Leu Ala Thr Tyr
                165                 170                 175

Phe Glu Ala Arg Ala Thr Lys Arg Ala Asn Lys Thr Thr Met Ala Gly
            180                 185                 190

Gly Arg Val Thr Glu Ala Ala Ile Ala Leu Ala Lys Leu Cys Tyr Asp
        195                 200                 205

Thr Gln Ile Leu Glu Gly Leu Lys Ala Lys Leu Ala Ala Glu Lys His
        210                 215                 220

Leu Val Thr Glu Ala Val Glu Lys Ile Ile Glu Ala Asn Thr Tyr Leu
225                 230                 235                 240

Ser Gly Ile Gly Xaa Glu Ser Gly Gly Leu Ala Ala His Ala Ile
                245                 250                 255

His Asn Gly Leu Thr Val Leu Glu Glu Thr His His Met Tyr His Gly
            260                 265                 270

Glu Lys Val Ala Phe Gly Thr Leu Ala Gln Leu Ile Leu Glu Asp Ala
        275                 280                 285

Pro Lys Ala Glu Ile Glu Glu Val Val Ser Phe Cys Leu Ser Val Gly
    290                 295                 300

Leu Pro Val Thr Leu Gly Asp Leu Gly Val Lys Glu Leu Asn Glu Glu
305                 310                 315                 320

Lys Leu Arg Lys Val Ala Glu Leu Ser Cys Ala Glu Gly Glu Thr Ile
                325                 330                 335

Tyr Asn Met Pro Phe Glu Val Thr Pro Asp Leu Val Tyr Ala Ala Ile
            340                 345                 350

Val Thr Ala Asp Ser Val Gly Arg Tyr Tyr Lys Glu Lys Trp Ala
        355                 360                 365

<210> SEQ ID NO 4
<211> LENGTH: 367
<212> TYPE: PRT
<213> ORGANISM: Bacillus coagulans
<220> FEATURE:
<221> NAME/KEY: MISC_FEATURE
<222> LOCATION: (121)..(121)
<223> OTHER INFORMATION: Xaa = Asp, Glu or Asn
<220> FEATURE:
<221> NAME/KEY: MISC_FEATURE
<222> LOCATION: (245)..(245)
<223> OTHER INFORMATION: Xaa = Phe, Ser, Thr, Gly or Asn

<400> SEQUENCE: 4

Met Thr Lys Ile Ile Thr Ser Pro Ser Lys Phe Ile Gln Gly Pro Asp
1               5                   10                  15

Glu Leu Ser Arg Leu Ser Ala Tyr Thr Glu Arg Leu Gly Lys Lys Ala
            20                  25                  30

Phe Ile Ile Ala Asp Asp Phe Val Thr Gly Leu Val Gly Lys Thr Val
        35                  40                  45

Glu Glu Ser Tyr Ala Gly Lys Glu Thr Gly Tyr Gln Met Ala Leu Phe
    50                  55                  60
```

Gly Gly Glu Cys Ser Lys Pro Glu Ile Glu Arg Leu Cys Glu Met Ser
65                  70                  75                  80

Lys Ser Glu Glu Ala Asp Val Val Gly Ile Gly Gly Lys Thr
            85                  90                  95

Leu Asp Thr Ala Lys Ala Val Gly Tyr Tyr Asn Asn Ile Pro Val Ile
            100                 105                 110

Val Ala Pro Thr Ile Ala Ser Thr Xaa Ala Pro Thr Ser Ala Leu Ser
            115                 120                 125

Val Ile Tyr Lys Glu Asn Gly Glu Phe Glu Glu Tyr Leu Met Leu Pro
            130                 135                 140

Leu Asn Pro Thr Phe Val Ile Met Asp Thr Lys Val Ile Ala Ser Ala
145                 150                 155                 160

Pro Ala Arg Leu Leu Val Ser Gly Met Gly Asp Ala Leu Ala Thr Tyr
                165                 170                 175

Phe Glu Ala Arg Ala Thr Lys Arg Ala Asn Lys Thr Thr Met Ala Gly
            180                 185                 190

Gly Arg Val Thr Glu Ala Ala Ile Ala Leu Ala Lys Leu Cys Tyr Asp
            195                 200                 205

Thr Gln Ile Leu Glu Gly Leu Lys Ala Lys Leu Ala Ala Glu Lys His
            210                 215                 220

Leu Val Thr Glu Ala Val Glu Lys Ile Ile Glu Ala Asn Thr Tyr Leu
225                 230                 235                 240

Ser Gly Ile Gly Xaa Glu Ser Gly Gly Leu Ala Ala Ala His Ala Ile
                245                 250                 255

His Asn Gly Leu Thr Val Leu Glu Glu Thr His His Met Tyr His Gly
            260                 265                 270

Glu Lys Val Ala Phe Gly Thr Leu Ala Gln Leu Ile Leu Glu Asp Ala
            275                 280                 285

Pro Lys Ala Glu Ile Glu Glu Val Ser Phe Cys Leu Ser Val Gly
            290                 295                 300

Leu Pro Val Thr Leu Gly Asp Leu Gly Val Lys Glu Leu Asn Glu Glu
305                 310                 315                 320

Lys Leu Arg Lys Val Ala Glu Leu Ser Cys Ala Glu Gly Glu Thr Ile
            325                 330                 335

Tyr Asn Met Pro Phe Glu Val Thr Pro Asp Leu Val Tyr Ala Ala Ile
            340                 345                 350

Val Thr Ala Asp Ser Val Gly Arg Tyr Tyr Lys Glu Lys Trp Ala
            355                 360                 365

<210> SEQ ID NO 5
<211> LENGTH: 367
<212> TYPE: PRT
<213> ORGANISM: Bacillus coagulans

<400> SEQUENCE: 5

Met Thr Lys Ile Ile Thr Ser Pro Ser Lys Phe Ile Gln Gly Pro Asp
1               5                   10                  15

Glu Leu Ser Arg Leu Ser Ala Tyr Thr Glu Arg Leu Gly Lys Lys Ala
            20                  25                  30

Phe Ile Ile Ala Asp Asp Phe Val Thr Gly Leu Val Gly Lys Thr Val
            35                  40                  45

Glu Glu Ser Tyr Ala Gly Lys Glu Thr Gly Tyr Gln Met Ala Leu Phe
50                  55                  60

Gly Gly Glu Cys Ser Lys Pro Glu Ile Glu Arg Leu Cys Glu Met Ser

```
            65                  70                  75                  80
Lys Ser Glu Glu Ala Asp Val Val Gly Ile Gly Gly Lys Thr
                    85                  90                  95

Leu Asp Thr Ala Lys Ala Val Gly Tyr Tyr Asn Asn Ile Pro Val Ile
                100                 105                 110

Val Ala Pro Thr Ile Ala Ser Thr Asp Ala Pro Thr Ser Ala Leu Ser
            115                 120                 125

Val Ile Tyr Lys Glu Asn Gly Glu Phe Glu Tyr Leu Met Leu Pro
130                 135                 140

Leu Asn Pro Thr Phe Val Ile Met Asp Thr Lys Val Ile Ala Ser Ala
145                 150                 155                 160

Pro Ala Arg Leu Leu Val Ser Gly Met Gly Asp Ala Leu Ala Thr Tyr
                165                 170                 175

Phe Glu Ala Arg Ala Thr Lys Arg Ala Asn Lys Thr Thr Met Ala Gly
                180                 185                 190

Gly Arg Val Thr Glu Ala Ala Ile Ala Leu Ala Lys Leu Cys Tyr Asp
            195                 200                 205

Thr Gln Ile Leu Glu Gly Leu Lys Ala Lys Leu Ala Ala Glu Lys His
            210                 215                 220

Leu Val Thr Glu Ala Val Glu Lys Ile Ile Glu Ala Asn Thr Tyr Leu
225                 230                 235                 240

Ser Gly Ile Gly Phe Glu Ser Gly Leu Ala Ala His Ala Ile
                    245                 250                 255

His Asn Gly Leu Thr Val Leu Glu Glu Thr His His Met Tyr His Gly
            260                 265                 270

Glu Lys Val Ala Phe Gly Thr Leu Ala Gln Leu Ile Leu Glu Asp Ala
            275                 280                 285

Pro Lys Ala Glu Ile Glu Glu Val Val Ser Phe Cys Leu Ser Val Gly
            290                 295                 300

Leu Pro Val Thr Leu Gly Asp Leu Gly Val Lys Glu Leu Asn Glu Glu
305                 310                 315                 320

Lys Leu Arg Lys Val Ala Glu Leu Ser Cys Ala Glu Gly Glu Thr Ile
                325                 330                 335

Tyr Asn Met Pro Phe Glu Val Thr Pro Asp Leu Val Tyr Ala Ala Ile
                340                 345                 350

Val Thr Ala Asp Ser Val Gly Arg Tyr Tyr Lys Glu Lys Trp Ala
                355                 360                 365

<210> SEQ ID NO 6
<211> LENGTH: 367
<212> TYPE: PRT
<213> ORGANISM: Bacillus coagulans

<400> SEQUENCE: 6

Met Thr Lys Ile Ile Thr Ser Pro Ser Lys Phe Ile Gln Gly Pro Asp
1               5                   10                  15

Glu Leu Ser Arg Leu Ser Ala Tyr Thr Glu Arg Leu Gly Lys Lys Ala
                20                  25                  30

Phe Ile Ile Ala Asp Asp Phe Val Thr Gly Leu Val Gly Lys Thr Val
            35                  40                  45

Glu Glu Ser Tyr Ala Gly Lys Glu Thr Gly Tyr Gln Met Ala Leu Phe
    50                  55                  60

Gly Gly Glu Cys Ser Lys Pro Glu Ile Glu Arg Leu Cys Glu Met Ser
65                  70                  75                  80
```

```
Lys Ser Glu Glu Ala Asp Val Val Val Gly Ile Gly Gly Lys Thr
                85                  90                  95

Leu Asp Thr Ala Lys Ala Val Gly Tyr Tyr Asn Asn Ile Pro Val Ile
            100                 105                 110

Val Ala Pro Thr Ile Ala Ser Thr Asp Ala Pro Thr Ser Ala Leu Ser
            115                 120                 125

Val Ile Tyr Lys Glu Asn Gly Glu Phe Glu Glu Tyr Leu Met Leu Pro
            130                 135                 140

Leu Asn Pro Thr Phe Val Ile Met Asp Thr Lys Val Ile Ala Ser Ala
145                 150                 155                 160

Pro Ala Arg Leu Leu Val Ser Gly Met Gly Asp Ala Leu Ala Thr Tyr
                165                 170                 175

Phe Glu Ala Arg Ala Thr Lys Arg Ala Asn Lys Thr Thr Met Ala Gly
            180                 185                 190

Gly Arg Val Thr Glu Ala Ala Ile Ala Leu Ala Lys Leu Cys Tyr Asp
            195                 200                 205

Thr Gln Ile Ser Glu Gly Leu Lys Ala Lys Leu Ala Ala Glu Lys His
            210                 215                 220

Leu Val Thr Glu Ala Val Glu Lys Ile Ile Glu Ala Asn Thr Tyr Leu
225                 230                 235                 240

Ser Gly Ile Gly Phe Glu Ser Gly Gly Leu Ala Ala Ala His Ala Ile
                245                 250                 255

His Asn Gly Leu Thr Val Leu Glu Glu Thr His His Met Tyr His Gly
            260                 265                 270

Glu Lys Val Ala Phe Gly Thr Leu Ala Gln Leu Ile Leu Glu Asp Ala
            275                 280                 285

Pro Lys Ala Glu Ile Glu Glu Val Val Ser Phe Cys Leu Ser Val Gly
            290                 295                 300

Leu Pro Val Thr Leu Gly Asp Leu Gly Val Lys Glu Leu Asn Glu Glu
305                 310                 315                 320

Lys Leu Arg Lys Val Ala Glu Leu Ser Cys Ala Glu Gly Glu Thr Ile
                325                 330                 335

Tyr Asn Met Pro Phe Glu Val Thr Pro Asp Leu Val Tyr Ala Ala Ile
            340                 345                 350

Val Thr Ala Asp Ser Val Gly Arg Tyr Tyr Lys Glu Lys Trp Ala
            355                 360                 365

<210> SEQ ID NO 7
<211> LENGTH: 366
<212> TYPE: PRT
<213> ORGANISM: Symbiobacterium thermophilum

<400> SEQUENCE: 7

Met Ser Lys Val Ile Val Ala Pro Gly Lys Tyr Ile Gln Gly Pro Gly
1               5                   10                  15

Glu Leu Asp Arg Leu Ala Glu His Thr Gly Gln Leu Gly Ala His Ala
                20                  25                  30

Phe Val Ile Ala Asp Glu Phe Val Met Asn Leu Thr Gly Asp Arg Val
            35                  40                  45

Thr Ala Ser Tyr Ala Lys Ala Gly Ala Ala Val Thr Met Glu Arg Phe
            50                  55                  60

Gln Gly Glu Ile Thr Gln Ala Glu Ile Glu Arg Leu Thr Ala Arg Cys
65                  70                  75                  80

Lys Glu Ser Gln Ala Asp Val Val Val Gly Ile Gly Gly Gly Lys Thr
                85                  90                  95
```

Leu Asp Ser Ala Lys Ala Val Ala Tyr Tyr Cys Gly Asn Leu Pro Ala
            100                 105                 110

Val Val Val Pro Thr Val Ala Ser Thr Asp Ala Pro Cys Ser Ala Leu
            115                 120                 125

Ser Val Ile Tyr Lys Glu Asp Gly Ser Phe Glu Arg Tyr Leu Phe Leu
            130                 135                 140

Pro Ser Asn Pro Ala Val Val Val Asp Thr Ala Ile Ile Ala Asn
145                 150                 155                 160

Ala Pro Val Arg Leu Leu Val Ala Gly Met Gly Asp Ala Leu Ala Thr
            165                 170                 175

Tyr Phe Glu Ala Arg Ala Ala Gln Arg Ala His Lys Leu Asn Ile Val
            180                 185                 190

Gly Gly His Gly Thr Gln Ala Ala Met Ala Leu Ala Arg Leu Cys Tyr
            195                 200                 205

Asp Thr Leu Leu Gln Glu Gly Ile Lys Ala Lys Ala Ala Glu Ala
            210                 215                 220

His Val Ile Thr Glu Ala Leu Glu Arg Ile Val Glu Ala Asn Thr Tyr
225                 230                 235                 240

Leu Ser Gly Leu Gly Phe Glu Ser Cys Gly Leu Ala Ala Ala His Ala
            245                 250                 255

Ile His Asn Gly Leu Ser Ala Leu Glu Glu Thr His Gly Ala Tyr His
            260                 265                 270

Gly Glu Lys Val Ala Phe Gly Thr Leu Ala Gln Leu Val Leu Glu Asn
            275                 280                 285

Ala Pro Leu Asp Glu Ile Glu Val Ile Glu Phe Cys Leu Asn Val
            290                 295                 300

Gly Leu Pro Val Thr Leu Ala Asp Leu Gly Val His Thr Val Arg Glu
305                 310                 315                 320

Glu Gln Ile Arg Arg Val Ala Glu Leu Ser Cys Ala Glu Gly Glu Thr
            325                 330                 335

Ile Phe Asn Met Pro Phe Glu Val Thr Pro Glu Lys Val Tyr Ala Ala
            340                 345                 350

Ile Leu Thr Ala Asp Arg Leu Gly His Leu Tyr Lys Gly Gly
            355                 360                 365

<210> SEQ ID NO 8
<211> LENGTH: 360
<212> TYPE: PRT
<213> ORGANISM: Vibrio parahaemolyticus

<400> SEQUENCE: 8

Met Asp Lys Ile Ile Ile Ser Pro Ser Lys Tyr Val Gln Gly Glu Gln
1               5                   10                  15

Val Leu Thr Ser Ile Ala His Tyr Val Lys Thr Leu Gly Glu Arg Pro
            20                  25                  30

Leu Val Ile Ala Asp Glu Phe Val Thr Asn Leu Val Gly Asp Val
            35                  40                  45

Lys Gln Ser Phe Ala Asp Glu Lys Leu Pro Leu Thr Met Asn Ile Phe
    50                  55                  60

Gly Gly Glu Cys Ser Arg Val Glu Ile Glu Arg Ile Thr Asp Ile Cys
65                  70                  75                  80

Ala Thr Gln Lys His Asp Val Ile Val Gly Ile Gly Gly Gly Lys Thr
            85                  90                  95

Leu Asp Thr Ala Lys Ala Val Ala Phe Tyr Thr Lys Ile Pro Val Val

```
            100                 105                 110
Val Val Pro Thr Ile Ala Ser Thr Asp Ala Pro Thr Ser Ala Leu Ala
        115                 120                 125

Val Ile Tyr Thr Pro Glu Gly Glu Phe Ala Glu Tyr Leu Met Ile Pro
    130                 135                 140

Lys Asn Pro Asp Met Val Ile Met Asp Thr Ser Val Ile Ala Lys Ala
145                 150                 155                 160

Pro Val Arg Leu Leu Val Ser Gly Met Gly Asp Ala Leu Ser Thr Tyr
                165                 170                 175

Phe Glu Ala Arg Ala Asn Met Thr Ser Gly Lys Ala Thr Met Ala Gly
            180                 185                 190

Gly Leu Ala Thr Arg Ser Ala Gln Ala Leu Ala Lys Leu Cys Tyr Glu
        195                 200                 205

Thr Leu Leu Glu Asp Gly Leu Lys Ala Lys Ala Val Glu Asn Gly
    210                 215                 220

Val Ser Thr Lys Ala Val Glu Asn Ile Ile Glu Ala Asn Thr Tyr Leu
225                 230                 235                 240

Ser Gly Ile Gly Phe Glu Ser Ser Gly Leu Ala Gly Ala His Ala Ile
                245                 250                 255

His Asn Gly Leu Thr Lys Leu Glu Glu Cys His His Leu Tyr His Gly
            260                 265                 270

Glu Lys Val Ala Phe Gly Thr Leu Val Gln Leu Val Leu Glu Asn Ala
        275                 280                 285

Ala Met Glu Glu Ile Asn Thr Val Leu Ala Phe Cys Arg Ser Val Gly
    290                 295                 300

Leu Pro Thr Asn Leu Phe Asp Met Gly Val Lys Glu Leu Asn His Ala
305                 310                 315                 320

Lys Leu Arg Glu Val Ala Glu Ala Ser Thr Ala Glu Gly Glu Thr Ile
                325                 330                 335

His Asn Met Pro Phe Pro Val Thr Ala Glu Asn Val Tyr Ser Ala Ile
            340                 345                 350

Leu Thr Ala His Gln Leu Gly Gln
        355                 360

<210> SEQ ID NO 9
<211> LENGTH: 360
<212> TYPE: PRT
<213> ORGANISM: Vibrio alginolyticus

<400> SEQUENCE: 9

Met Asp Lys Ile Ile Ser Pro Ser Lys Tyr Val Gln Gly Glu Gln
1               5                   10                  15

Val Leu Thr Ser Ile Ala His Tyr Val Lys Thr Leu Gly Glu Arg Pro
                20                  25                  30

Leu Val Ile Ala Asp Glu Phe Val Thr Asn Leu Val Gly Asp Asp Val
            35                  40                  45

Lys Gln Ser Phe Ala Asp Glu Lys Leu Pro Leu Thr Met Asn Ile Phe
50                  55                  60

Gly Gly Glu Cys Ser Arg Val Glu Ile Glu Arg Ile Thr Asp Ile Cys
65                  70                  75                  80

Ala Thr Gln Lys His Asp Val Ile Val Gly Ile Gly Gly Gly Lys Thr
                85                  90                  95

Leu Asp Thr Ala Lys Ala Val Ala Phe Tyr Thr Lys Ile Pro Val Val
            100                 105                 110
```

```
Val Val Pro Thr Ile Ala Ser Thr Asp Ala Pro Thr Ser Ala Leu Ala
            115                 120                 125

Val Ile Tyr Thr Pro Glu Gly Glu Phe Ala Glu Tyr Leu Met Ile Pro
        130                 135                 140

Lys Asn Pro Asp Met Val Ile Met Asp Thr Ser Val Ile Ala Lys Ala
145                 150                 155                 160

Pro Val Arg Leu Leu Val Ser Gly Met Gly Asp Ala Leu Ser Thr Tyr
                165                 170                 175

Phe Glu Ala Arg Ala Asn Met Thr Ser Gly Lys Ala Thr Met Ala Gly
                180                 185                 190

Gly Leu Ala Thr Arg Ser Ala Gln Ala Leu Ala Lys Leu Cys Tyr Glu
            195                 200                 205

Thr Leu Glu Asp Gly Val Lys Ala Lys Ala Val Glu Asn Gly
            210                 215                 220

Val Ser Thr Lys Ala Val Glu Asn Ile Ile Glu Ala Asn Thr Tyr Leu
225                 230                 235                 240

Ser Gly Ile Gly Phe Glu Ser Ser Gly Leu Ala Gly Ala His Ala Ile
                245                 250                 255

His Asn Gly Leu Thr Lys Leu Glu Glu Cys His His Leu Tyr His Gly
            260                 265                 270

Glu Lys Val Ala Phe Gly Thr Leu Val Gln Leu Val Leu Glu Asn Ala
        275                 280                 285

Ala Met Glu Glu Ile Asn Thr Val Leu Ala Phe Cys Arg Ser Val Gly
        290                 295                 300

Leu Pro Thr Asn Leu Phe Asp Met Gly Val Lys Glu Leu Asn His Ala
305                 310                 315                 320

Lys Leu Arg Glu Val Ala Glu Ala Ser Thr Ala Glu Gly Glu Thr Ile
                325                 330                 335

His Asn Met Pro Phe Pro Val Thr Ala Glu Asn Val Tyr Ser Ala Ile
                340                 345                 350

Leu Thr Ala His Gln Leu Gly Gln
            355                 360

<210> SEQ ID NO 10
<211> LENGTH: 362
<212> TYPE: PRT
<213> ORGANISM: Psychromonas sp.

<400> SEQUENCE: 10

Met Asp Lys Ile Ile Ile Ser Pro Ser Lys Tyr Ile Gln Gly Glu Asn
1               5                   10                  15

Val Leu Ala Ala Ile Ser Glu Tyr Val Leu Pro Val Gly Arg Gln Ala
            20                  25                  30

Met Ala Ile Ala Asp Glu Phe Val Thr Gly Leu Val Gly Glu Thr Val
        35                  40                  45

Lys Gln Ser Phe Arg Asp Gln Asp Ser Glu Leu Thr Met Glu Ile Phe
    50                  55                  60

Asn Gly Glu Cys Ser Arg Thr Glu Ile Glu Arg Leu Leu Leu Leu Ser
65                  70                  75                  80

Glu Gln Ala Asn Ala Asp Val Ile Ile Gly Ile Gly Gly Gly Lys Thr
                85                  90                  95

Leu Asp Thr Ala Lys Ala Ile Gly Phe Tyr Arg Lys Ile Pro Val Val
            100                 105                 110

Val Val Pro Thr Ile Ala Ser Thr Asp Ala Pro Thr Ser Ala Leu Ala
            115                 120                 125
```

```
Val Ile Tyr Thr Pro Glu Gly Gln Phe Ser Glu Tyr Leu Met Ile Pro
        130                 135                 140

Thr Asn Pro Asn Met Val Ile Met Asp Ser Lys Ile Ile Ala Ala Ala
145                 150                 155                 160

Pro Val Arg Leu Leu Val Ser Gly Met Gly Asp Ala Leu Ser Thr His
                165                 170                 175

Phe Glu Ala Arg Ala Asn Ala Arg Ser Gly Lys Thr Met Ala Gly
                180                 185                 190

Gly Ala Pro Thr Lys Ala Ala Gln Ala Leu Ala Lys Leu Cys Tyr Glu
                195                 200                 205

Thr Leu Leu Ala Asp Gly Leu Gln Ala Lys Ile Ala Val Glu Asn Gly
        210                 215                 220

Leu Ser Ser Gln Ala Val Glu Asn Ile Ile Glu Ala Asn Thr Tyr Leu
225                 230                 235                 240

Ser Gly Ile Gly Phe Glu Ser Ser Gly Leu Ala Gly Ala His Ala Ile
                245                 250                 255

His Asn Gly Leu Thr Lys Leu Glu Glu Cys His His Leu Phe His Gly
                260                 265                 270

Glu Lys Val Ala Phe Gly Thr Leu Val Gln Leu Val Leu Glu Asn Ala
                275                 280                 285

Pro Met Glu Glu Ile Asn Thr Val Leu Glu Phe Cys His Ser Val Gly
290                 295                 300

Leu Pro Thr Asn Leu His Ala Met Gly Val Lys Val Leu Asp Arg Asp
305                 310                 315                 320

Lys Leu Leu Glu Val Ala Lys Ala Ser Cys Ala Glu Gly Glu Thr Ile
                325                 330                 335

His Asn Met Pro Phe Val Val Thr Pro Ile Ala Val Leu Ser Ala Ile
                340                 345                 350

Leu Val Ala His Glu Leu Gly Ser Lys Lys
                355                 360

<210> SEQ ID NO 11
<211> LENGTH: 361
<212> TYPE: PRT
<213> ORGANISM: Pseudovibrio sp.

<400> SEQUENCE: 11

Met Asp Gln Ile Ile Ile Ser Pro Ser Lys Tyr Val Gln Gly Glu Asp
1               5                   10                  15

Thr Ile Ala Lys Ile Gly Asp Tyr Ile Lys Pro Leu Gly Gln Lys Ala
                20                  25                  30

Ala Ile Leu Ala Asp Ser Phe Val Thr Gly Leu Val Gly Asp Thr Val
                35                  40                  45

Lys Lys Ser Cys Ala Asp Ala Gly Ile Glu Gln Arg Met Glu Glu Phe
        50                  55                  60

Gly Gly Glu Cys Ser Arg Ala Val Ile Asp Arg Leu Met Glu Ile Phe
65                  70                  75                  80

Lys Ala Glu Gly Ser Asp Val Val Val Gly Ile Gly Gly Gly Lys Thr
                85                  90                  95

Leu Asp Thr Ala Lys Ala Ile Gly Phe Tyr His Lys Ile Pro Val Val
                100                 105                 110

Val Val Pro Thr Ile Ala Ser Thr Asp Ala Pro Thr Ser Ala Leu Ala
                115                 120                 125

Val Ile Tyr Thr Pro Glu Gly Glu Phe Ser Glu Tyr Leu Leu Phe Pro
```

```
            130                 135                 140
Ser Asn Pro Asn Leu Val Ile Met Asp Thr Lys Ile Ala Gly Ala
145                 150                 155                 160

Pro Val Arg Leu Leu Val Ala Gly Ile Gly Asp Ala Leu Ser Thr Tyr
                165                 170                 175

Phe Glu Ala Arg Ala Asn Gly Leu Ser Gly Lys Ala Thr Met Ala Gly
                180                 185                 190

Gly Leu Pro Thr Lys Ala Ala Gln Ala Leu Ala Lys Leu Cys Tyr Glu
                195                 200                 205

Thr Leu Leu Ala Asp Gly Tyr Lys Ala Lys Val Ala Val Glu Asn Arg
            210                 215                 220

Val Ser Ser Thr Ala Val Lys Asn Ile Ile Glu Ala Asn Thr Leu Leu
225                 230                 235                 240

Ser Gly Leu Gly Phe Glu Ser Ser Gly Leu Ala Ala His Ala Ile
                245                 250                 255

His Asn Gly Leu Thr Lys Leu Glu Glu Cys His His Leu Tyr His Gly
                260                 265                 270

Glu Lys Val Ala Phe Gly Thr Leu Thr Gln Leu Leu Leu Glu Asn Ala
            275                 280                 285

Pro Met Glu Glu Ile Gln Glu Val Leu Thr Leu Cys Arg Ser Val Gly
290                 295                 300

Leu Pro Thr Asn Leu Phe Asp Met Gly Val Lys Glu Leu Asp His Ala
305                 310                 315                 320

Lys Leu Met Glu Val Ala Glu Ala Ser Cys Ala Glu Gly Glu Thr Ile
                325                 330                 335

His Asn Met Pro Phe Pro Val Thr Pro Glu Met Val Tyr Ala Ala Met
                340                 345                 350

Leu Cys Ala His Gln Ile Gly Leu Lys
                355                 360

<210> SEQ ID NO 12
<211> LENGTH: 367
<212> TYPE: PRT
<213> ORGANISM: Proteus penneri

<400> SEQUENCE: 12

Met Leu Lys Val Ile Gln Ser Pro Ala Lys Tyr Ile Gln Gly Pro Asp
1               5                   10                  15

Ala Leu Tyr His Ile Gly Lys Tyr Ala Lys Pro Phe Gly Asp Arg Ala
                20                  25                  30

Leu Ile Ile Ala Asp Lys Phe Val Met Asp Leu Val Gly Ser Thr Val
            35                  40                  45

Lys Asp Ser Met Ser Gln Tyr Glu Val Asn Gly His Phe Glu Leu Phe
50                  55                  60

Asn Gly Glu Cys Thr His Asn Glu Ile Asn Arg Leu Ser Glu Leu Val
65                  70                  75                  80

Lys Glu Gln Ala Ser Leu Val Ile Val Gly Val Gly Gly Gly Lys Thr
                85                  90                  95

Leu Asp Thr Ala Lys Ala Val Ala Tyr Lys Cys Gln Leu Pro Val Val
                100                 105                 110

Ile Ser Pro Thr Ile Ala Ser Thr Asp Ala Pro Thr Ser Ala Leu Ser
            115                 120                 125

Val Ile Tyr Thr Glu Leu Gly Ala Phe Asp Ser Tyr Leu Phe Tyr Pro
            130                 135                 140
```

```
Thr Asn Pro Asp Val Val Met Asp Thr Asn Ile Ile Ala Ser Ala
145                 150                 155                 160

Pro Ala Arg Leu Leu Val Ala Gly Met Gly Asp Ala Leu Ala Thr Tyr
            165                 170                 175

Phe Glu Ala Arg Ala Cys Ser Gln Ala Gln Lys Gln Thr Met Ala Gly
            180                 185                 190

Gly Lys Ser Thr Leu Ala Ala Leu Ala Leu Ala Glu Leu Cys Tyr Asn
            195                 200                 205

Thr Leu Leu Glu Asp Gly Tyr Lys Ala Lys Leu Ala Val Ser Arg Gly
210                 215                 220

Val Cys Thr Ala Ala Val Glu Asn Ile Ile Glu Ala Asn Thr Phe Leu
225                 230                 235                 240

Ser Gly Ile Gly Phe Glu Ser Ala Gly Leu Ala Ala His Ala Ile
            245                 250                 255

His Asn Gly Phe Thr Ala Leu Glu Glu Cys His Asn Met Tyr His Gly
            260                 265                 270

Glu Lys Val Ala Phe Gly Thr Leu Val Gln Leu Val Leu Glu Asn Ser
            275                 280                 285

Pro Leu Glu Glu Leu Glu Glu Phe Leu Asp Phe Cys Ile Leu Val Gly
            290                 295                 300

Leu Pro Val Thr Leu Glu Glu Leu Gly Ile Asn Ala Thr Gly Asp Glu
305                 310                 315                 320

Leu Asn Glu Lys Ile Met Ala Val Ala Glu Leu Ser Cys Ala Glu Gly
            325                 330                 335

Glu Thr Ile Tyr Asn Met Pro Phe Asp Ile Asp Ser Asp Lys Val Tyr
            340                 345                 350

Ala Ala Ile Leu Thr Ala Asp Gln Leu Gly Arg Glu Trp Leu Tyr
            355                 360                 365

<210> SEQ ID NO 13
<211> LENGTH: 367
<212> TYPE: PRT
<213> ORGANISM: Proteus mirabilis

<400> SEQUENCE: 13

Met Leu Lys Val Ile Gln Ser Pro Ala Lys Tyr Ile Gln Gly Pro Asp
1               5                   10                  15

Ala Leu Tyr His Ile Gly Lys Tyr Thr Lys Pro Leu Gly Glu Arg Ala
            20                  25                  30

Leu Ile Ile Ala Asp Lys Phe Val Met Asp Leu Ala Gly Ser Ile Val
            35                  40                  45

Lys Asp Ser Met Thr Gln Tyr Glu Val Asn Gly His Phe Glu Gln Phe
50                  55                  60

His Gly Glu Cys Thr His Lys Glu Ile Asp Arg Leu Val Glu Ile Ala
65                  70                  75                  80

Lys Gln Gln Ala Ala Leu Val Ile Ile Gly Val Gly Gly Gly Lys Thr
            85                  90                  95

Leu Asp Thr Ala Lys Ala Val Ala Tyr Lys Cys Gln Leu Pro Val Val
            100                 105                 110

Ile Ser Pro Thr Ile Ala Ser Thr Asp Ala Pro Thr Ser Ala Leu Ser
            115                 120                 125

Val Ile Tyr Thr Glu Leu Gly Ala Phe Asp Ser Tyr Leu Phe Tyr Pro
            130                 135                 140

Lys Asn Pro Asp Ile Val Val Met Asp Thr Asn Val Ile Ala Ser Ala
145                 150                 155                 160
```

```
Pro Pro Arg Leu Leu Val Ala Gly Met Gly Asp Ala Leu Ala Thr Tyr
            165                 170                 175

Phe Glu Ala Arg Ala Cys Ser Arg Ala Gln Lys Gln Thr Met Ala Gly
            180                 185                 190

Gly Lys Thr Thr Leu Ala Ala Leu Ala Leu Ala Glu Leu Cys Tyr His
            195                 200                 205

Thr Leu Leu Glu Asp Gly Tyr Lys Ala Lys Leu Ala Val Ser Arg Ser
    210                 215                 220

Val Cys Thr Thr Ala Val Glu Asn Ile Ile Glu Ala Asn Thr Phe Leu
225                 230                 235                 240

Ser Gly Ile Gly Phe Glu Ser Ala Gly Leu Ala Ala His Ala Ile
            245                 250                 255

His Asn Gly Phe Thr Ala Leu Glu Glu Cys His Ala Met Tyr His Gly
            260                 265                 270

Glu Lys Val Ala Phe Gly Thr Leu Val Gln Leu Val Leu Glu Asn Ser
            275                 280                 285

Pro Leu Glu Glu Ile Glu Glu Val Leu Asp Phe Cys Val Gln Val Gly
    290                 295                 300

Leu Pro Val Thr Leu Glu Glu Leu Gly Val His Ala Thr Gly Asp Glu
305                 310                 315                 320

Leu Asn Glu Lys Ile Met Ala Val Ala Glu Leu Ser Cys Ala Glu Gly
            325                 330                 335

Glu Thr Ile Tyr Asn Met Pro Phe Asp Val Asp Ser Asp Lys Val Phe
            340                 345                 350

Ala Ala Ile Met Ala Ala Asp Gln Leu Gly Arg Glu Trp Leu Tyr
            355                 360                 365

<210> SEQ ID NO 14
<211> LENGTH: 365
<212> TYPE: PRT
<213> ORGANISM: Klebsiella pneumoniae

<400> SEQUENCE: 14

Met Leu Lys Val Ile Gln Ser Pro Ala Lys Tyr Leu Gln Gly Pro Asp
1               5                   10                  15

Ala Ala Val Leu Phe Gly Gln Tyr Ala Lys Asn Leu Ala Glu Ser Phe
            20                  25                  30

Phe Val Ile Ala Asp Asp Phe Val Met Lys Leu Ala Gly Glu Lys Val
            35                  40                  45

Val Asn Gly Leu Gln Ser His Asp Ile Arg Cys His Ala Glu Arg Phe
50                  55                  60

Asn Gly Glu Cys Ser His Ala Glu Ile Asn Arg Leu Met Ala Ile Leu
65                  70                  75                  80

Gln Lys Gln Gly Cys Arg Gly Val Val Gly Ile Gly Gly Lys Thr
            85                  90                  95

Leu Asp Thr Ala Lys Ala Ile Gly Tyr Tyr Gln Lys Leu Pro Val Val
            100                 105                 110

Val Ile Pro Thr Ile Ala Ser Thr Asp Ala Pro Thr Ser Ala Leu Ser
            115                 120                 125

Val Ile Tyr Thr Glu Ala Gly Glu Phe Glu Glu Tyr Leu Ile Tyr Pro
            130                 135                 140

Lys Asn Pro Asp Met Val Val Met Asp Thr Ala Ile Ile Ala Lys Ala
145                 150                 155                 160

Pro Val Arg Leu Leu Val Ser Gly Met Gly Asp Ala Leu Ser Thr Trp
```

```
                            165                 170                 175
Phe Glu Ala Lys Ala Cys Tyr Asp Ala Arg Ala Thr Ser Met Ala Gly
                180                 185                 190

Gly Gln Ser Thr Glu Ala Ala Leu Ser Leu Ala Arg Leu Cys Tyr Asp
            195                 200                 205

Thr Leu Leu Ala Glu Gly Glu Lys Ala Arg Leu Ala Ala Gln Ala Gly
        210                 215                 220

Val Val Thr Glu Ala Leu Glu Arg Ile Ile Glu Ala Asn Thr Tyr Leu
225                 230                 235                 240

Ser Gly Ile Gly Phe Glu Ser Ser Gly Leu Ala Ala His Ala Ile
            245                 250                 255

His Asn Gly Phe Thr Ile Leu Glu Glu Cys His His Leu Tyr His Gly
                260                 265                 270

Glu Lys Val Ala Phe Gly Thr Leu Ala Gln Leu Val Leu Gln Asn Ser
            275                 280                 285

Pro Met Asp Glu Ile Glu Thr Val Leu Gly Phe Cys Gln Arg Val Gly
        290                 295                 300

Leu Pro Val Thr Leu Ala Gln Met Gly Val Lys Glu Gly Ile Asp Glu
305                 310                 315                 320

Lys Ile Ala Ala Val Ala Lys Ala Thr Cys Ala Glu Gly Glu Thr Ile
                325                 330                 335

His Asn Met Pro Phe Ala Val Thr Pro Glu Ser Val His Ala Ala Ile
            340                 345                 350

Leu Thr Ala Asp Leu Leu Gly Gln Gln Trp Leu Ala Arg
        355                 360                 365

<210> SEQ ID NO 15
<211> LENGTH: 365
<212> TYPE: PRT
<213> ORGANISM: Klebsiella varicola

<400> SEQUENCE: 15

Met Leu Lys Val Ile Gln Ser Pro Ala Lys Tyr Leu Gln Gly Pro Asp
1               5                   10                  15

Ala Ala Val Leu Phe Gly Gln Tyr Ala Lys Asn Leu Ala Glu Ser Phe
                20                  25                  30

Phe Val Ile Ala Asp Asp Phe Val Met Lys Leu Ala Gly Glu Lys Val
            35                  40                  45

Val Asn Gly Leu Gln Ser His Asp Ile Arg Cys His Ala Glu Arg Phe
        50                  55                  60

Asn Gly Glu Cys Ser His Val Glu Ile Asn Arg Leu Met Ala Ile Leu
65                  70                  75                  80

Gln Lys Gln Gly Cys Arg Gly Val Val Gly Ile Gly Gly Gly Lys Thr
                85                  90                  95

Leu Asp Thr Ala Lys Ala Ile Gly Tyr Tyr Gln Lys Leu Pro Val Val
            100                 105                 110

Val Ile Pro Thr Ile Ala Ser Thr Asp Ala Pro Thr Ser Ala Leu Ser
        115                 120                 125

Val Ile Tyr Thr Glu Ala Gly Glu Phe Glu Glu Tyr Leu Ile Tyr Pro
        130                 135                 140

Lys Asn Pro Asp Met Val Val Met Asp Thr Ala Ile Ile Ala Lys Ala
145                 150                 155                 160

Pro Val Arg Leu Leu Val Ser Gly Met Gly Asp Ala Leu Ser Thr Trp
                165                 170                 175
```

```
Phe Glu Ala Lys Ala Cys Tyr Asp Ala Arg Ala Thr Ser Met Ala Gly
                180                 185                 190

Gly Gln Ser Thr Glu Ala Ala Leu Ser Leu Ala Arg Leu Cys Tyr Asp
            195                 200                 205

Thr Leu Leu Ala Glu Gly Glu Lys Ala Arg Leu Ala Ala Gln Ala Gly
210                 215                 220

Val Val Thr Glu Ala Leu Glu Arg Ile Ile Glu Ala Asn Thr Tyr Leu
225                 230                 235                 240

Ser Gly Ile Gly Phe Glu Ser Ser Gly Leu Ala Ala His Ala Ile
                245                 250                 255

His Asn Gly Phe Thr Ile Leu Glu Glu Cys His His Leu Tyr His Gly
                260                 265                 270

Glu Lys Val Ala Phe Gly Thr Leu Ala Gln Leu Val Leu Gln Asn Ser
            275                 280                 285

Pro Met Asp Glu Ile Glu Thr Val Leu Gly Phe Cys Gln Arg Val Gly
            290                 295                 300

Leu Pro Val Thr Leu Ala Gln Met Gly Val Lys Glu Gly Ile Asp Ala
305                 310                 315                 320

Lys Ile Ala Ala Val Ala Lys Ala Thr Cys Ala Glu Gly Glu Thr Ile
                325                 330                 335

His Asn Met Pro Phe Ala Val Thr Pro Glu Ser Val His Ala Ala Ile
                340                 345                 350

Leu Thr Ala Asp Leu Leu Gly Gln Gln Trp Leu Ala Arg
            355                 360                 365

<210> SEQ ID NO 16
<211> LENGTH: 368
<212> TYPE: PRT
<213> ORGANISM: Citrobacter koseri

<400> SEQUENCE: 16

Met Thr Gly Met Leu Lys Val Ile Gln Ser Pro Ala Lys Tyr Leu Gln
1               5                   10                  15

Gly Pro Asp Ala Ser Val Leu Phe Gly Gln Tyr Ala Lys Asp Leu Ala
            20                  25                  30

Asp Ser Phe Phe Val Ile Ala Asp Asp Phe Val Met Lys Leu Ala Gly
        35                  40                  45

Glu Lys Val Leu Asn Gly Leu Asn Ser His Glu Ile Arg Cys His Ala
    50                  55                  60

Glu Arg Phe Asn Gly Glu Cys Ser His Val Glu Ile Asn Arg Leu Met
65                  70                  75                  80

Ala Ile Leu Lys Gln Lys Gly Cys Arg Gly Val Val Gly Ile Gly Gly
                85                  90                  95

Gly Lys Thr Leu Asp Thr Ala Lys Ala Ile Gly Tyr Tyr Gln Lys Leu
            100                 105                 110

Pro Val Val Ile Ile Pro Thr Ile Ala Ser Thr Asp Ala Pro Thr Ser
        115                 120                 125

Ala Leu Ser Val Ile Tyr Thr Glu Ala Gly Glu Phe Glu Glu Tyr Leu
130                 135                 140

Ile Tyr Pro Lys Asn Pro Asp Met Val Val Met Asp Thr Ala Ile Ile
145                 150                 155                 160

Ala Lys Ala Pro Val Arg Leu Leu Val Ser Gly Met Gly Asp Ala Leu
                165                 170                 175

Ser Thr Trp Phe Glu Ala Lys Ala Cys Tyr Asp Ala Arg Ala Thr Ser
            180                 185                 190
```

```
Met Ala Gly Gly Gln Ser Thr Ala Ala Leu Ser Leu Ala Arg Leu
            195                 200                 205

Cys Tyr Asp Thr Leu Leu Ala Glu Gly Glu Lys Ala Arg Leu Ala Ala
210                 215                 220

Gln Ala Gly Val Val Thr Asp Ala Leu Glu Arg Ile Val Glu Ala Asn
225                 230                 235                 240

Thr Tyr Leu Ser Gly Ile Gly Phe Glu Ser Gly Leu Ala Gly Ala
            245                 250                 255

His Ala Ile His Asn Gly Phe Thr Ile Leu Glu Glu Cys His His Leu
            260                 265                 270

Tyr His Gly Glu Lys Val Ala Phe Gly Thr Leu Ala Gln Leu Val Leu
            275                 280                 285

Gln Asn Ser Pro Met Glu Glu Ile Glu Thr Val Leu Gly Phe Cys Glu
290                 295                 300

Lys Val Gly Leu Pro Ile Thr Leu Ala Gln Met Gly Val Lys Asp Gly
305                 310                 315                 320

Ile Glu Gly Lys Ile Gln Ala Val Ala Lys Ala Thr Cys Ala Glu Gly
                325                 330                 335

Glu Thr Ile His Asn Met Pro Phe Glu Val Thr Pro Asp Ser Val Tyr
            340                 345                 350

Ala Ala Ile Leu Thr Ala Asp Leu Leu Gly Gln Gln Trp Leu Ala Arg
            355                 360                 365

<210> SEQ ID NO 17
<211> LENGTH: 364
<212> TYPE: PRT
<213> ORGANISM: Yersinia mollaretii

<400> SEQUENCE: 17

Met Leu Lys Val Ile Gln Ser Pro Ser Lys Tyr Ile Gln Gly Ala Asn
1               5                   10                  15

Ala Leu Gln Ser Ile Gly Glu Phe Ala Lys Leu Leu Ala Asn Asn Tyr
                20                  25                  30

Phe Ile Ile Ala Asp Asp Phe Val Met Lys Leu Thr Ala Asp Thr Val
            35                  40                  45

Ser Ser Ser Leu His Gly Ser Glu Leu Glu Asn His Phe Ser Arg Phe
    50                  55                  60

Asn Gly Glu Cys Ser Arg Gln Glu Ile Glu Arg Leu Thr Val Glu Leu
65                  70                  75                  80

Lys Lys His His Cys Asn Gly Val Ile Gly Ile Gly Gly Lys Thr
                85                  90                  95

Leu Asp Thr Ala Lys Ala Ile Ala His Tyr Gln His Ile Pro Val Ile
            100                 105                 110

Val Val Pro Thr Ile Ala Ser Thr Asp Ala Pro Thr Ser Ala Leu Ser
            115                 120                 125

Val Ile Tyr Thr Glu Gln Gly Glu Phe Ala Glu Tyr Leu Ile Tyr Pro
            130                 135                 140

Lys Asn Pro Asp Ile Val Leu Met Asp Ser Ala Ile Ile Ala Lys Ala
145                 150                 155                 160

Pro Val Arg Leu Leu Val Ser Gly Met Gly Asp Ala Leu Ser Thr Tyr
                165                 170                 175

Phe Glu Ala Gln Ala Cys Phe Asp Ala Lys Ala Ile Ser Met Ala Gly
            180                 185                 190

Gly Ala Ser Thr Leu Ala Ala Val Thr Leu Ala Arg Leu Cys Tyr Glu
```

```
            195                 200                 205
Thr Leu Leu Ala Glu Gly Tyr Lys Ala Lys Leu Ala Val Glu Ala Gly
210                 215                 220

Val Val Thr Glu Ala Val Glu Arg Ile Ile Glu Ala Asn Thr Tyr Leu
225                 230                 235                 240

Ser Gly Ile Gly Phe Glu Ser Ser Gly Leu Ala Ala His Ala Ile
            245                 250                 255

His Asn Gly Phe Thr Val Leu Glu Glu Cys His His Leu Tyr His Gly
            260                 265                 270

Glu Lys Val Ala Phe Gly Thr Leu Thr Gln Leu Val Leu Gln Asn Ser
            275                 280                 285

Ser Met Glu Glu Ile Glu Thr Val Leu Ser Phe Cys Gln Gln Leu Gly
            290                 295                 300

Leu Pro Ile Thr Leu Ala Glu Met Gly Val Thr Gln Asp Ile Glu Arg
305                 310                 315                 320

Lys Ile Arg Ala Val Ala Gln Ala Ser Cys Ala Glu Gly Glu Thr Ile
            325                 330                 335

His Asn Met Pro Phe Ala Val Thr Pro Asp Ser Val Tyr Ala Ala Ile
            340                 345                 350

Ile Val Ala Asp Ser Leu Gly Glu Ala Phe Leu Asn
            355                 360

<210> SEQ ID NO 18
<211> LENGTH: 366
<212> TYPE: PRT
<213> ORGANISM: Xenorhabdus bovienii

<400> SEQUENCE: 18

Met Leu Lys Val Ile Gln Ser Pro Ser Lys Tyr Ile Gln Gly Pro Gly
1               5                   10                  15

Ala Leu Ser His Ile Gly Gln Tyr Thr Lys Ile Leu Ala Asp His Val
            20                  25                  30

Phe Val Ile Ala Asp Asn Phe Val Met Ser Leu Ile Gly Asp Ala Val
        35                  40                  45

Ser Lys Ser Leu Glu Ala His Ala Val Thr Ser His Phe Glu Ile Phe
    50                  55                  60

Asn Gly Glu Cys Ser Arg Gly Glu Ile Lys Arg Leu Ser Asp Ile Ser
65                  70                  75                  80

Ala Ser His Gln Cys Gln Ala Val Ile Gly Ile Gly Gly Lys Thr
            85                  90                  95

Leu Asp Thr Ala Lys Ala Ile Ala His Ala Cys Arg Leu Pro Val Ile
            100                 105                 110

Ile Ser Pro Thr Ile Ala Ser Thr Asp Ala Pro Thr Ser Ala Leu Ser
            115                 120                 125

Val Leu Tyr Thr Glu Leu Gly Glu Phe Asp Gly Tyr Leu Leu Tyr Pro
130                 135                 140

Gln Asn Pro Asn Ile Val Leu Met Asp Thr Arg Ile Ile Ala Lys Ala
145                 150                 155                 160

Pro Val Arg Leu Leu Val Ala Gly Met Gly Asp Ala Leu Ala Thr Tyr
            165                 170                 175

Phe Glu Ala Arg Ala Asn Ser Ala Ala His Lys Pro Thr Met Ala Gly
            180                 185                 190

Gly Ala Thr Ser Asn Thr Gly Leu Ala Leu Ala Lys Leu Cys Tyr Asp
            195                 200                 205
```

-continued

Thr Leu Leu Ala Glu Gly Tyr Lys Ala Lys Leu Ala Val Glu Ala Gly
210                 215                 220

Val Ser Thr Pro Ala Val Glu Asn Ile Ile Glu Ala Asn Thr Tyr Leu
225                 230                 235                 240

Ser Gly Ile Gly Phe Glu Ser Ala Gly Leu Ala Ala His Ala Ile
            245                 250                 255

His Asn Gly Phe Thr Val Leu Glu Glu Cys His His Leu Tyr His Gly
            260                 265                 270

Glu Lys Val Ala Phe Gly Thr Leu Ala Gln Leu Met Leu Glu Asn Ser
                275                 280                 285

Pro Asn Glu Glu Leu Glu Thr Val Leu Asp Phe Cys Val Gln Val Gly
290                 295                 300

Leu Pro Val Thr Leu Glu Gln Leu Gly Leu Arg Asp Ser Glu Lys Leu
305                 310                 315                 320

His Gln Lys Ile Met Glu Val Ala Lys Ala Ser Cys Ala Glu Gly Glu
                325                 330                 335

Thr Ile His Asn Met Pro Phe Lys Val Thr Pro Glu Gln Val Tyr Ala
            340                 345                 350

Ala Ile Met Ala Ala Asp Arg Met Gly Met Asp Trp Leu Tyr
            355                 360                 365

<210> SEQ ID NO 19
<211> LENGTH: 368
<212> TYPE: PRT
<213> ORGANISM: T. thermosaccharolyticum

<400> SEQUENCE: 19

Met Thr Lys Ala Ile Ile Gly Pro Ser Lys Tyr Val Gln Gly Asn Gly
1               5                   10                  15

Glu Leu Arg Arg Ile Ser Glu His Thr Lys Ser Leu Gly Lys Asn Phe
                20                  25                  30

Leu Val Ile Ala Ser Ser Asn Gly Ile Ile Arg Thr Lys Ser Ile Ile
            35                  40                  45

Glu Glu Ser Phe Ser Asn Thr Glu Ile Ser Leu Cys Phe Glu Ser Phe
50                  55                  60

Gly Gly Glu Cys Ser Glu Glu Ile Glu Arg Leu Arg Asn Phe Val
65                  70                  75                  80

Lys Lys Thr Asn Ser Asp Val Ile Val Gly Ile Gly Gly Lys Ile
                85                  90                  95

Phe Asp Thr Val Lys Ala Val Ala Tyr Tyr Glu Asn Ile Pro Val Val
            100                 105                 110

Ile Val Pro Thr Ile Ala Ser Thr Asp Ala Pro Cys Ser Ala Leu Ser
            115                 120                 125

Val Ile Tyr Thr Ser Glu Gly Ile Phe Ser Lys Tyr Leu Leu Leu Pro
130                 135                 140

Lys Asn Pro Asp Leu Val Leu Val Asp Thr Glu Ile Ile Ala Ser Ala
145                 150                 155                 160

Pro Ala Arg Leu Leu Val Ala Gly Met Gly Asp Ala Leu Ala Thr Tyr
                165                 170                 175

Phe Glu Ala Arg Ala Cys Leu Arg Ser Asn Ala Ser Thr Met Ala Gly
            180                 185                 190

Ala Lys Ser Thr Lys Ala Ala Met Ala Leu Ala Lys Leu Cys Tyr Asp
        195                 200                 205

Thr Leu Leu Glu Asp Gly Leu Lys Ala Lys Leu Ala Val Glu Asn Lys
210                 215                 220

```
Thr Val Thr Lys Ala Val Glu Asn Ile Val Glu Ala Asn Thr Tyr Leu
225                 230                 235                 240

Ser Gly Ile Gly Phe Glu Ser Gly Gly Leu Ala Ala His Ala Ile
            245                 250                 255

His Asn Gly Phe Thr Val Ile Glu Glu Cys His Gln Leu Tyr His Gly
            260                 265                 270

Glu Lys Val Ala Phe Gly Thr Leu Val Gln Leu Val Leu Glu Asn Ser
        275                 280                 285

Pro Leu Glu Glu Ile Glu Val Val Glu Phe Cys Met Ser Val Gly
290                 295                 300

Leu Pro Val Thr Leu Glu Asp Ile Gly Ile Lys Glu Ile Asn Tyr Glu
305                 310                 315                 320

Lys Ile Lys Lys Val Ala Glu Ala Ser Cys Ala Pro Asp Glu Thr Ile
            325                 330                 335

His Asn Met Pro Phe Lys Val Val Ala Ala Asp Val Tyr Ala Ala Ile
            340                 345                 350

Leu Ser Ala Asp Ala Ile Gly Lys Met Tyr Lys Asn Lys Arg Ser Arg
        355                 360                 365
```

<210> SEQ ID NO 20
<211> LENGTH: 387
<212> TYPE: PRT
<213> ORGANISM: Thermosediminibacter oceani

<400> SEQUENCE: 20

```
Met Arg Ile Pro Val Pro Gly Val Ile Leu Ile Lys Tyr Leu Gly Gly
1               5                   10                  15

Arg Phe Thr Val Thr Arg Ala Ile Ile Gly Pro Gly Lys Tyr Val Gln
            20                  25                  30

Gly Asn Gly Val Leu Lys Asp Ile Lys Glu His Thr Met Lys Leu Gly
        35                  40                  45

Arg Ser Phe Phe Ile Ile Ala Ser Glu Asn Gly Ile Lys Arg Thr Lys
    50                  55                  60

Pro Val Ile Glu Glu Ser Phe Ala Gly Glu Lys Val Glu Leu Val Phe
65                  70                  75                  80

Glu Pro Phe Asn Gly Glu Cys Ser Glu Asn Glu Ile Glu Arg Leu Lys
                85                  90                  95

Gly Leu Ala Glu Lys Asn Asn Ser Gln Val Ile Val Gly Ile Gly Gly
            100                 105                 110

Gly Lys Val Leu Asp Thr Ala Lys Ala Ile Ala Tyr Phe Leu Lys Leu
        115                 120                 125

Pro Val Val Val Pro Thr Val Ala Ser Thr Asp Ala Pro Cys Ser
130                 135                 140

Ala Leu Ser Val Ile Tyr Thr Asp Glu Gly Val Phe Ser Lys Tyr Leu
145                 150                 155                 160

Ile Leu Pro Arg Asn Pro Asp Val Val Met Val Asp Thr Gly Phe Ile
                165                 170                 175

Val Lys Ala Pro Ala Arg Leu Leu Ala Ala Gly Met Gly Asp Ala Leu
            180                 185                 190

Ala Thr Tyr Phe Glu Ala Arg Ala Cys Phe Arg Ser Asn Ala Thr Thr
        195                 200                 205

Leu Ala Gly Gly Lys Ser Thr Lys Ala Ala Met Ala Leu Ala Glu Leu
    210                 215                 220

Cys Tyr Arg Thr Leu Leu Glu Asp Gly Leu Lys Ala Lys Leu Ala Val
```

```
            225                 230                 235                 240
Glu Asn Asn Ala Cys Thr Leu Ala Val Glu Asn Ile Val Glu Ala Asn
                245                 250                 255
Thr Tyr Leu Ser Gly Ile Gly Phe Glu Ser Gly Gly Leu Ala Ala Ala
                260                 265                 270
His Ala Ile His Asn Gly Phe Thr Val Leu Glu Glu Cys His His Met
                275                 280                 285
Tyr His Gly Glu Lys Val Ala Phe Gly Thr Ile Val Gln Leu Val Leu
                290                 295                 300
Glu Asn Ser Pro Met Glu Glu Leu Glu Val Val Gly Phe Cys Leu
305                 310                 315                 320
Asp Val Gly Leu Pro Val Thr Leu Glu Asp Leu Gly Ile Lys Glu Val
                325                 330                 335
Lys Glu Ala Asp Ile Arg Lys Val Ala Glu Ala Ser Cys Ala Glu Gly
                340                 345                 350
Glu Thr Ile His Asn Met Pro Phe Lys Val Thr Pro Glu Asp Val Tyr
                355                 360                 365
Asn Ala Ile Leu Gly Ala Asp Ala Leu Gly Arg Thr Leu Lys Asn Gln
                370                 375                 380
Tyr Ile Arg
385

<210> SEQ ID NO 21
<211> LENGTH: 363
<212> TYPE: PRT
<213> ORGANISM: Clostridium ljungdahlii

<400> SEQUENCE: 21

Met Ser Arg Ile Ile Ile Ser Thr Gly Lys Tyr Val Gln Gly Asn Gly
1               5                   10                  15
Glu Leu Lys Asn Ile Ser Asn Tyr Val Glu Asn Leu Gly Asp Ser Phe
                20                  25                  30
Phe Ile Ile Ala Ser Glu Asn Gly Ile Lys Arg Thr Arg Asp Ala Ile
            35                  40                  45
Glu Glu Ser Phe Lys Gly Lys Asp Ser Leu Leu Ala Phe Glu Ala Phe
        50                  55                  60
Asn Gly Glu Cys Ser Lys Asn Glu Ile Asp Arg Leu Cys Lys Lys Leu
65                  70                  75                  80
Lys Glu Asn Lys Asn Asn Val Val Ile Gly Ile Gly Gly Lys Ile
                85                  90                  95
Phe Asp Thr Ala Lys Ala Val Ala Tyr Tyr Ala Lys Val Pro Val Val
                100                 105                 110
Ile Val Pro Thr Ile Ala Ala Thr Asp Ala Pro Cys Ser Ala Leu Ser
                115                 120                 125
Val Ile Tyr Thr Asp Glu Gly Val Phe Ser Glu Tyr Leu Ala Leu Pro
                130                 135                 140
Lys Asn Pro Asp Leu Val Leu Val Asp Ser Ser Ile Val Ala Lys Ala
145                 150                 155                 160
Pro Val Arg Leu Leu Val Ser Gly Met Gly Asp Ala Leu Ala Thr Tyr
                165                 170                 175
Phe Glu Ala Arg Ala Cys Val Arg Ser Gly Ala Val Thr Met Ser Gly
                180                 185                 190
Gly Lys Ala Thr Lys Ala Ala Phe Ala Leu Ser Lys Leu Cys Tyr Asp
                195                 200                 205
```

Thr Leu Leu Glu Asp Gly Leu Lys Ala Lys Met Ala Val Ile Asn Lys
    210                 215                 220

Val Pro Thr Lys Ala Val Glu Asn Ile Ile Glu Ala Asn Thr Tyr Leu
225                 230                 235                 240

Ser Gly Val Gly Phe Glu Ser Ser Gly Leu Ala Ala His Ala Ile
                245                 250                 255

His Asn Gly Phe Thr Ala Leu Glu Glu Cys His Gly Leu Tyr His Gly
                260                 265                 270

Glu Lys Val Ala Phe Gly Ala Leu Val Gln Leu Val Leu Glu Asn Ser
                275                 280                 285

Pro Met Glu Glu Ile Glu Val Ile Asp Phe Cys Leu Gln Val Gly
290                 295                 300

Leu Pro Ile Thr Leu Asn Asp Leu Gly Ile Lys Lys Val Asn Asn Glu
305                 310                 315                 320

Asp Ile Met Lys Val Ala Glu Ile Ser Cys Ala Glu Asn Asp Thr Met
                325                 330                 335

His Asn Met Pro Phe Glu Val Thr Lys Glu Asp Val Tyr Ser Ala Ile
                340                 345                 350

Leu Ala Ala Asp Glu Leu Gly Lys Gln Tyr Lys
                355                 360

<210> SEQ ID NO 22
<211> LENGTH: 363
<212> TYPE: PRT
<213> ORGANISM: Clostridium botulinum

<400> SEQUENCE: 22

Met Ala Lys Ile Ile Ile Ser Pro Ser Lys Tyr Val Gln Gly Asn Gly
1               5                   10                  15

Glu Leu Lys Lys Ile Tyr Asp His Ile Gly Asn Leu Gly Lys Ser Phe
                20                  25                  30

Leu Phe Ile Val Ser Lys Ser Gly Phe Lys Arg Thr Gly Asp Val Ile
                35                  40                  45

Lys Lys Ser Phe Glu Asn Thr Asn Ser Lys Ile Thr Phe Glu Ile Phe
50                  55                  60

Asn Gly Glu Cys Ser His Asn Glu Ile Glu Arg Leu Lys Lys Val Cys
65                  70                  75                  80

Ala Glu Asn Asn Cys Asp Val Val Gly Val Gly Gly Lys Ile
                85                  90                  95

Leu Asp Thr Ala Lys Ala Val Ser Tyr Tyr Glu Lys Ser Pro Val Val
                100                 105                 110

Ile Val Pro Thr Ile Ala Ser Thr Asp Ala Pro Cys Ser Ala Leu Ser
                115                 120                 125

Val Ile Tyr Thr Glu Asp Gly Thr Phe Ser Glu Tyr Ile Leu Leu Pro
                130                 135                 140

Lys Asn Pro Asp Ile Val Leu Met Asp Thr Glu Ile Ile Ser Lys Ala
145                 150                 155                 160

Pro Ala Arg Leu Leu Val Ala Gly Met Gly Asp Ala Leu Ala Thr Phe
                165                 170                 175

Phe Glu Ala Arg Ala Cys Ala Lys Ala Asn Ala Asn Asn Met Ser Gly
                180                 185                 190

Gly Lys Ile Thr Lys Ala Leu Ala Leu Thr Leu Cys Tyr Glu
                195                 200                 205

Thr Leu Ile Glu Asp Gly Leu Lys Ala Lys Leu Ala Val Glu Lys Lys
                210                 215                 220

```
Val Cys Thr Lys Ala Val Glu Asn Ile Val Glu Ala Asn Thr Tyr Leu
225                 230                 235                 240

Ser Gly Ile Gly Phe Glu Ser Ala Gly Leu Ala Ala His Ala Ile
            245                 250                 255

His Asn Gly Phe Thr Val Leu Glu Glu Cys His His Leu Tyr His Gly
            260                 265                 270

Glu Lys Val Ala Phe Gly Thr Ile Val Gln Leu Ile Leu Glu Asn Ser
        275                 280                 285

Pro Met Glu Glu Ile Gln Val Leu Glu Phe Cys Ile Glu Leu Gly
    290                 295                 300

Leu Pro Val Thr Leu Lys Gln Leu Gly Ile Asn Glu Ile Asn Glu Glu
305                 310                 315                 320

Lys Leu Met Glu Val Ser Lys Thr Ser Cys Ala Glu Gly Glu Thr Ile
                325                 330                 335

Tyr Asn Met Pro Phe Glu Val Thr Pro Asn Asp Val Tyr Ala Ala Ile
            340                 345                 350

Leu Ala Ala Asp Ala Leu Gly Gln Ser Leu Ser
        355                 360

<210> SEQ ID NO 23
<211> LENGTH: 365
<212> TYPE: PRT
<213> ORGANISM: Ruminococcus gnavus

<400> SEQUENCE: 23

Met Ala Lys Val Leu Ile Ser Pro Gly Lys Tyr Val Gln Gly Ala Gly
1               5                   10                  15

Glu Met Lys Lys Leu Gly Glu Tyr Ala Gln Asn Tyr Gly Lys Lys Ala
            20                  25                  30

Leu Ile Leu Ile Ser Lys Gly Gly Tyr Lys Arg Ile Gly Ala Met Val
        35                  40                  45

Glu Lys Ser Phe Glu Gly Lys Glu Cys Gly Tyr Val Phe Asp Tyr Phe
    50                  55                  60

Asn Gly Glu Cys Ser Lys Lys Glu Ile Lys Arg Leu Gly Glu Ile Val
65                  70                  75                  80

Lys Lys Glu Ala Cys Asp Val Val Ile Gly Ile Gly Gly Gly Lys Ile
                85                  90                  95

Phe Asp Thr Ala Lys Ala Val Ala Tyr Tyr Glu Lys Thr Pro Val Leu
            100                 105                 110

Ile Cys Pro Thr Ile Ala Ser Thr Asp Ala Pro Cys Ser Ala Leu Ser
        115                 120                 125

Val Ile Tyr Thr Glu Glu Gly Val Phe Glu Glu Tyr Leu Phe Leu Pro
    130                 135                 140

Ser Asn Pro Asp Met Val Met Met Asp Thr Glu Ile Ile Ala Glu Ser
145                 150                 155                 160

Pro Val Arg Leu Thr Val Ala Gly Met Gly Asp Ala Leu Ala Thr Tyr
                165                 170                 175

Phe Glu Ala Arg Ala Cys Gln Arg Ser Asp Ala Ala Ser Cys Ala Gly
            180                 185                 190

Gly Lys Ile Thr Gly Ala Ala Met Ala Leu Ala Lys Leu Cys Phe Asp
        195                 200                 205

Thr Leu Met Glu Glu Gly Val Lys Ala Lys Leu Ala Leu Glu Ala Asp
    210                 215                 220

Ala Cys Thr Glu Ala Val Glu Lys Val Ile Glu Ala Asn Thr Leu Leu
```

```
225                 230                 235                 240

Ser Gly Ile Gly Phe Glu Ser Gly Leu Ala Gly Ala His Ala Ile
                245                 250                 255

His Asn Gly Leu Thr Val Leu Glu Glu Cys His His Met Tyr His Gly
                260                 265                 270

Glu Lys Val Ala Phe Gly Thr Ile Thr Gln Leu Val Leu Glu Asn Ile
                275                 280                 285

Pro Ser Glu Glu Leu Gln Gln Val Ile Asp Phe Cys Ile Glu Cys Gly
                290                 295                 300

Leu Pro Val Thr Leu Glu Gln Leu Gly Ala Gly Lys Ile Thr Glu Glu
305                 310                 315                 320

Gln Leu Met Lys Val Ala Glu Ala Ala Cys Ala Glu Thr Asp Thr Leu
                325                 330                 335

His Asn Met Pro Phe Glu Val Thr Pro Lys Lys Val Ala Asp Ala Ile
                340                 345                 350

Lys Ala Ala Asp Ala Tyr Gly His Tyr Phe Leu Gly Glu
                355                 360                 365

<210> SEQ ID NO 24
<211> LENGTH: 363
<212> TYPE: PRT
<213> ORGANISM: Geobacillus thermoglucosidasius

<400> SEQUENCE: 24

Met Ala Arg Ile Ile Asn Ser Pro Thr Lys Tyr Ile Gln Gly Arg Gly
1               5                   10                  15

Glu Leu Gln Asn Leu Gly Lys Tyr Ile Asn Ser Leu Gly Asn Ser Phe
                20                  25                  30

Leu Val Ile Ala Asp Gln Phe Val Leu Asn Phe Thr Lys Glu Thr Ile
                35                  40                  45

Glu Gln Ser Phe Ser Asp Gln Glu Ser Thr Leu Thr Phe Glu Thr Phe
    50                  55                  60

Arg Gly Glu Cys Ser Lys Gln Glu Val Asn Arg Leu Gln Thr Ile Ala
65                  70                  75                  80

Lys Glu Lys Gln Ile Asp Val Ile Val Gly Val Gly Gly Gly Lys Thr
                85                  90                  95

Leu Asp Thr Ala Lys Ala Val Ala Phe Tyr Ser Lys Leu Pro Val Val
                100                 105                 110

Ile Val Pro Thr Ile Ala Ser Thr Asp Ala Pro Cys Ser Ala Leu Ser
                115                 120                 125

Val Leu Tyr Thr Glu Glu Gly Val Phe Asp Glu Tyr Leu Ile Leu Pro
    130                 135                 140

Lys Asn Pro Asp Ile Val Leu Val Asp Thr Gln Ile Val Ala Asn Ala
145                 150                 155                 160

Pro Ala Arg Leu Leu Ala Ala Gly Ile Gly Asp Ala Leu Ala Thr Tyr
                165                 170                 175

Val Glu Ala Arg Ala Cys Tyr Glu Ala Asn Ala Thr Pro Met Ala Gly
                180                 185                 190

Gly Thr Ile Thr Lys Ala Ala Ile Ala Leu Ala Glu Leu Cys Gln Asn
                195                 200                 205

Ile Leu Phe Glu Asp Gly Ile Lys Ala Phe Leu Ala Val Glu Gln Asn
    210                 215                 220

Ile Val Thr Lys Ala Val Glu Asn Ile Val Glu Ala Asn Thr Tyr Leu
225                 230                 235                 240
```

```
Ser Gly Ile Gly Phe Glu Ser Gly Gly Leu Ala Ala His Ala Ile
            245                 250                 255

His Asn Gly Phe Thr Val Ile Asp Asp Thr His His Leu Tyr His Gly
        260                 265                 270

Glu Lys Val Ala Phe Gly Val Ile Thr Gln Leu Val Leu Glu Asn Arg
    275                 280                 285

Ser Thr Glu Glu Ile Gln Lys Tyr Ile Ala Phe Cys Thr Glu Leu Gly
290                 295                 300

Leu Pro Val Thr Leu Glu Asp Met Gly Ile Thr Glu Asp Ile Glu Pro
305                 310                 315                 320

Lys Ile Arg Lys Val Ala Glu Ala Ala Cys Gln Glu Gly Glu Thr Ile
                325                 330                 335

Tyr Asn Met Pro Phe Pro Val Thr Pro Asp Asp Val Tyr Ala Ala Ile
            340                 345                 350

Ile Ser Ala Asp Ile Leu Gly Arg Lys Tyr Lys
            355                 360

<210> SEQ ID NO 25
<211> LENGTH: 367
<212> TYPE: PRT
<213> ORGANISM: Salmonella enterica

<400> SEQUENCE: 25

Met Asp Arg Ile Ile Gln Ser Pro Gly Lys Tyr Ile Gln Gly Ala Asn
1               5                   10                  15

Val Ile Ala Arg Leu Gly Asp Tyr Leu Lys Pro Met Ala Asn Asn Trp
            20                  25                  30

Leu Val Val Gly Asp Lys Phe Val Leu Gly Phe Ala Glu Glu Thr Leu
        35                  40                  45

Arg Lys Ser Leu Thr Asp Ala Gly Leu Ser Val Glu Ile Ala Pro Phe
    50                  55                  60

Gly Gly Glu Cys Ser Gln Asn Glu Ile Asp Arg Leu Arg Ala Val Ala
65                  70                  75                  80

Glu Lys Ser Gln Cys Gly Ala Val Leu Gly Ile Gly Gly Gly Lys Thr
                85                  90                  95

Leu Asp Thr Ala Lys Ala Leu Ala His Phe Met Asn Val Pro Val Ala
            100                 105                 110

Ile Ala Pro Thr Ile Ala Ser Thr Asp Ala Pro Cys Ser Ala Leu Ser
        115                 120                 125

Val Ile Tyr Thr Asp Ala Gly Glu Phe Asp Arg Tyr Leu Leu Leu Pro
    130                 135                 140

His Asn Pro Asn Met Val Ile Val Asp Thr Gln Ile Val Ala Gly Ala
145                 150                 155                 160

Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
            180                 185                 190

Gly Lys Cys Thr Gln Ala Ala Leu Ala Leu Ala Glu Leu Cys Tyr Asn
        195                 200                 205

Thr Leu Ile Glu Glu Gly Glu Lys Ala Met Leu Ala Ala Glu Gln His
    210                 215                 220

Val Val Thr Pro Ala Leu Glu Arg Val Ile Glu Ala Asn Thr Tyr Leu
225                 230                 235                 240

Ser Gly Val Gly Phe Glu Ser Gly Gly Leu Ala Ala His Ala Ile
                245                 250                 255
```

```
His Asn Gly Leu Thr Ala Ile Pro Asp Ala His His Tyr Tyr His Gly
            260                 265                 270

Glu Lys Val Ala Phe Gly Thr Leu Thr Gln Leu Val Leu Glu Asn Ala
            275                 280                 285

Pro Val Glu Glu Ile Glu Thr Val Ala Ala Leu Cys His Ser Val Gly
290                 295                 300

Leu Pro Ile Thr Leu Ala Gln Leu Asp Ile Lys Gln Asp Ile Pro Ala
305                 310                 315                 320

Lys Met Arg Thr Val Ala Glu Ala Ser Cys Ala Gly Glu Thr Ile
            325                 330                 335

His Asn Met Pro Gly Gly Ala Thr Pro Asp Glu Val Tyr Ala Ala Leu
            340                 345                 350

Leu Val Ala Asp Gln Tyr Gly Gln Arg Phe Leu Gln Glu Trp Glu
            355                 360                 365

<210> SEQ ID NO 26
<211> LENGTH: 367
<212> TYPE: PRT
<213> ORGANISM: Escherichia coli

<400> SEQUENCE: 26

Met Asp Arg Ile Ile Gln Ser Pro Gly Lys Tyr Ile Gln Gly Ala Asp
1               5                   10                  15

Val Ile Asn Arg Leu Gly Glu Tyr Leu Lys Pro Leu Ala Glu Arg Trp
                20                  25                  30

Leu Val Val Gly Asp Lys Phe Val Leu Gly Phe Ala Gln Ser Thr Val
            35                  40                  45

Glu Lys Ser Phe Lys Asp Ala Gly Leu Val Val Glu Ile Ala Pro Phe
        50                  55                  60

Gly Gly Glu Cys Ser Gln Asn Glu Ile Asp Arg Leu Arg Gly Ile Ala
65                  70                  75                  80

Glu Thr Ala Gln Cys Gly Ala Ile Leu Gly Ile Gly Gly Gly Lys Thr
                85                  90                  95

Leu Asp Thr Ala Lys Ala Leu Ala His Phe Met Gly Val Pro Val Ala
            100                 105                 110

Ile Ala Pro Thr Ile Ala Ser Thr Asp Ala Pro Cys Ser Ala Leu Ser
        115                 120                 125

Val Ile Tyr Thr Asp Glu Gly Glu Phe Asp Arg Tyr Leu Leu Leu Pro
        130                 135                 140

Asn Asn Pro Asn Met Val Ile Val Asp Thr Lys Ile Val Ala Gly Ala
145                 150                 155                 160

Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
            180                 185                 190

Gly Lys Cys Thr Gln Ala Ala Leu Ala Leu Ala Glu Leu Cys Tyr Asn
        195                 200                 205

Thr Leu Leu Glu Glu Gly Glu Lys Ala Met Leu Ala Ala Glu Gln His
    210                 215                 220

Val Val Thr Pro Ala Leu Glu Arg Val Ile Glu Ala Asn Thr Tyr Leu
225                 230                 235                 240

Ser Gly Val Gly Phe Glu Ser Gly Gly Leu Ala Ala Ala His Ala Val
                245                 250                 255

His Asn Gly Leu Thr Ala Ile Pro Asp Ala His His Tyr Tyr His Gly
```

```
            260                 265                 270
Glu Lys Val Ala Phe Gly Thr Leu Thr Gln Leu Val Leu Glu Asn Ala
                275                 280                 285

Pro Val Glu Glu Ile Glu Thr Val Ala Ala Leu Ser His Ala Val Gly
            290                 295                 300

Leu Pro Ile Thr Leu Ala Gln Leu Asp Ile Lys Glu Asp Val Pro Ala
305                 310                 315                 320

Lys Met Arg Ile Val Ala Glu Ala Ala Cys Ala Glu Gly Glu Thr Ile
                325                 330                 335

His Asn Met Pro Gly Gly Ala Thr Pro Asp Gln Val Tyr Ala Ala Leu
                340                 345                 350

Leu Val Ala Asp Gln Tyr Gly Gln Arg Phe Leu Gln Glu Trp Glu
                355                 360                 365

<210> SEQ ID NO 27
<211> LENGTH: 367
<212> TYPE: PRT
<213> ORGANISM: Enterobacter cloacae

<400> SEQUENCE: 27

Met Asp Arg Ile Ile Gln Ser Pro Gly Lys Tyr Ile Gln Gly Ala Asp
1               5                   10                  15

Val Leu Thr Arg Leu Gly Asp Tyr Leu Lys Pro Leu Ala Thr Arg Trp
                20                  25                  30

Leu Val Val Gly Asp Lys Phe Val Leu Gly Phe Ala Glu Glu Thr Leu
            35                  40                  45

Arg Gln Ser Phe Lys Asn Ala Glu Leu His Ala Glu Ile Ala Pro Phe
        50                  55                  60

Gly Gly Glu Cys Ser Gln Asn Glu Ile Asp Arg Leu Lys Lys Leu Ala
65                  70                  75                  80

Asp Ser Ala Asp Cys Met Ala Val Leu Gly Ile Gly Gly Gly Lys Thr
                85                  90                  95

Leu Asp Thr Ala Lys Ala Leu Ala His Phe Met Asp Val Pro Val Ala
            100                 105                 110

Ile Ala Pro Thr Ile Ala Ser Thr Asp Ala Pro Cys Ser Ala Leu Ser
        115                 120                 125

Val Ile Tyr Thr Asp Ser Gly Glu Phe Glu Arg Tyr Leu Met Leu Pro
130                 135                 140

His Asn Pro Asn Met Val Ile Val Asp Thr Lys Val Val Ala Gly Ala
145                 150                 155                 160

Pro Pro Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
            180                 185                 190

Gly Lys Cys Thr Gln Ala Ala Leu Ala Leu Ala Glu Leu Cys Tyr Asn
        195                 200                 205

Thr Leu Ile Glu Glu Gly Glu Lys Ala Met Leu Ala Ala Glu Gln His
        210                 215                 220

Val Val Thr Pro Ala Leu Glu Arg Ile Ile Glu Ala Asn Thr Tyr Leu
225                 230                 235                 240

Ser Gly Val Gly Phe Glu Ser Gly Gly Leu Ala Ala Ala His Ala Ile
                245                 250                 255

His Asn Gly Met Thr Ala Val Pro Asp Ala His His Phe Tyr His Gly
            260                 265                 270
```

Glu Lys Val Ala Phe Gly Thr Leu Thr Gln Leu Val Leu Glu Asn Ala
              275                 280                 285

Pro Val Glu Glu Ile Glu Thr Val Ala Ala Leu Cys His Ser Val Gly
        290                 295                 300

Leu Pro Ile Thr Leu Ala Gln Leu Asn Ile Lys Glu Asp Ile Pro Ala
305                 310                 315                 320

Lys Met Arg Leu Ile Ala Glu Ala Ser Cys Ala Glu Gly Glu Thr Ile
                325                 330                 335

His Asn Met Pro Gly Gly Val Ser Pro Asp Gln Val Tyr Ala Ala Leu
            340                 345                 350

Leu Val Ala Asp Gln Tyr Gly Gln Arg Phe Leu Gln Glu Trp Glu
        355                 360                 365

<210> SEQ ID NO 28
<211> LENGTH: 368
<212> TYPE: PRT
<213> ORGANISM: Tolumonas auensis

<400> SEQUENCE: 28

Met Asp Lys Ile Ile Gln Ser Pro Gly Lys Tyr Val Gln Gly Ala Gly
1               5                   10                  15

Val Ile Ser Arg Val Gly Gln Tyr Ala Ala Pro Phe Ala Lys Lys Leu
            20                  25                  30

Leu Val Ile Ser Asp Ala Phe Val Leu Gly Leu Ile Glu Gly Lys Val
        35                  40                  45

Thr Ala Ser Phe Lys Glu Ser Ala Thr Asp Phe Val Ile Glu Lys Phe
    50                  55                  60

Lys Gly Glu Cys Ser Arg Asn Glu Val Asn Arg Leu Ile Thr Ile Leu
65              70                  75                  80

Gln Asn Glu Asn Cys Asp Gly Val Val Gly Val Gly Gly Gly Lys Thr
                85                  90                  95

Leu Asp Thr Ala Lys Ala Val Ala Tyr Tyr Ala Lys Val Pro Val Val
            100                 105                 110

Ile Ala Pro Thr Ile Ala Ser Thr Asp Ala Pro Cys Ser Ala Leu Ser
        115                 120                 125

Val Ile Tyr Thr Asp Thr Gly Glu Phe Glu Ser Tyr Leu Ile Leu Pro
    130                 135                 140

Cys Asn Pro Asn Val Val Leu Val Asp Thr Glu Ile Val Ala Gly Ala
145                 150                 155                 160

Pro Ala Arg Leu Leu Ala Ala Gly Ile Gly Asp Ala Met Ala Thr Tyr
                165                 170                 175

Phe Glu Ala Arg Ala Cys Tyr Gln Ser Arg Ala Thr Thr Met Ala Gly
            180                 185                 190

Gly Glu Ser Thr Glu Ala Ala Met Ser Leu Ala Arg Leu Cys Phe Asp
        195                 200                 205

Thr Leu Leu Ala Glu Gly His Lys Ala Met Leu Ala Val Gln Lys Lys
    210                 215                 220

Val Val Thr Glu Ala Val Glu Arg Ile Ile Glu Ala Asn Thr Tyr Leu
225                 230                 235                 240

Ser Gly Val Gly Phe Glu Ser Gly Gly Leu Ala Ala His Ala Val
                245                 250                 255

His Asn Gly Leu Thr Val Ile Pro Asp Ala His His Phe Tyr His Gly
            260                 265                 270

Glu Lys Val Ala Phe Gly Thr Leu Val Gln Leu Ile Leu Glu Asn Ala
        275                 280                 285

```
Pro Lys Ala Glu Leu Asp Thr Val Cys Ala Leu Cys Thr Arg Val Gly
    290                 295                 300

Leu Pro Ile Thr Leu Ala Gln Leu Asp Ile Lys Glu Gly Ile Glu Glu
305                 310                 315                 320

Lys Met Arg Ala Ala Glu Ala Ala Cys Ala Glu Gly Glu Thr Ile
                325                 330                 335

His Ser Met Pro Phe Lys Val Thr Ala Thr Lys Val Tyr Ala Ala Met
                340                 345                 350

Ile Ala Ala Asp Gln Tyr Gly Gln Asp Tyr Ile Lys Gln Asn Thr Lys
                355                 360                 365

<210> SEQ ID NO 29
<211> LENGTH: 364
<212> TYPE: PRT
<213> ORGANISM: Sebaldella termitidis

<400> SEQUENCE: 29

Met Asp Lys Ile Ile Leu Ser Pro Ser Lys Tyr Val Gln Gly Tyr Asn
1               5                   10                  15

Thr Ile Glu Arg Leu Glu Val Tyr Thr Ser Ser Leu Gly Lys Asn Ser
                20                  25                  30

Leu Ile Ile Ala Asp Asp Phe Ile Thr Lys Ile Ile Lys Glu Pro Val
            35                  40                  45

Ser Asn Ser Tyr Gln Asn Ser Ser Ser Asn Ile Leu Phe Glu Lys Phe
        50                  55                  60

Asn Gly Glu Cys Ser Lys Thr Glu Ile Asn Arg Leu Met Glu Ile Ile
65                  70                  75                  80

Gln Gln Asn Lys Ile Asp Ser Ile Val Gly Ile Gly Gly Gly Lys Thr
                85                  90                  95

Leu Asp Thr Ala Lys Ala Val Ser Tyr Tyr Ala Lys Ile Pro Val Val
                100                 105                 110

Ile Val Pro Thr Ile Ala Ser Thr Asp Ala Pro Cys Ser Ala Leu Ser
            115                 120                 125

Val Ile Tyr Thr Asp Glu Gly Val Phe Ser Glu Tyr Leu Phe Leu Ser
        130                 135                 140

Lys Asn Pro Asp Leu Val Ile Met Asp Thr Lys Ile Ile Ala Asn Ala
145                 150                 155                 160

Pro Val Arg Leu Leu Ala Ala Gly Met Gly Asp Ala Leu Ala Thr Tyr
                165                 170                 175

Phe Glu Ala Arg Ala Cys Thr Ala Ala Asn Lys Lys Thr Met Ala Gly
                180                 185                 190

Gly Thr Ala Thr Lys Ala Ser Ala Ala Leu Ala Glu Leu Cys Tyr Asn
                195                 200                 205

Thr Leu Leu Ser Asp Gly Tyr Leu Ala Lys Leu Ser Val Glu Asn Lys
        210                 215                 220

Val Val Thr Lys Ser Leu Glu Asn Ile Ile Glu Ala Asn Thr Tyr Leu
225                 230                 235                 240

Ser Gly Val Gly Phe Glu Ser Gly Gly Leu Ala Ala Ala His Ala Ile
                245                 250                 255

His Asn Gly Leu Thr Val Val Glu Glu Leu His His Leu Tyr His Gly
                260                 265                 270

Glu Lys Val Thr Phe Gly Val Leu Val Gln Leu Val Leu Glu Asn Ala
                275                 280                 285

Pro Lys Asn Glu Ile Glu Asp Val Leu Ser Phe Cys Lys Lys Ile Asn
```

```
            290                 295                 300
Leu Pro Val Cys Phe Lys Asp Met Gly Ile Glu Asn Ile Asn Lys Glu
305                 310                 315                 320

Lys Ile Tyr Glu Ala Ala Lys Leu Ala Cys Ala Glu Gly Glu Thr Ile
                325                 330                 335

Tyr Asn Met Pro Phe Glu Val Thr Val Asp Asp Val Tyr Ser Ala Ile
            340                 345                 350

Leu Thr Ala Asn Ser Leu Gly Glu Asp Phe Ser Ser
            355                 360

<210> SEQ ID NO 30
<211> LENGTH: 378
<212> TYPE: PRT
<213> ORGANISM: Paenibacillus sp. JDR-2

<400> SEQUENCE: 30

Met Arg Lys Ala Phe Ile Ser Pro Ser Lys Tyr Val Gln Gly Glu Asn
1               5                   10                  15

Glu Leu Leu Asn Leu Gly Phe Phe Val Gln Ser Tyr Gly Asp Ser Ala
                20                  25                  30

Leu Leu Ile Ala His Pro Glu Asp Val Lys Arg Val Lys Asp Lys Leu
            35                  40                  45

Asp Phe Thr Ser Asn Lys Phe Asn Ile Thr Leu Val Glu Ser Gly Phe
50                  55                  60

Arg Gly Glu Cys Ser Arg Glu Ile Ala Arg Leu Lys Glu Leu Ala
65                  70                  75                  80

Arg Glu Lys Asn Cys Ser Cys Thr Ile Gly Leu Gly Gly Lys Ala
                85                  90                  95

Ile Asp Thr Ala Lys Cys Val Ala Glu Gly Glu Ala Leu Ile Ile Val
            100                 105                 110

Pro Thr Ile Ala Ala Thr Asp Ala Pro Thr Ser His Ser Ala Val Ile
            115                 120                 125

Tyr Thr Asn Asp Gly Ala Phe Glu Asp Tyr Ala Tyr Phe Lys Ser Ser
            130                 135                 140

Pro Ser Val Val Met Ile Asp Thr Thr Val Ile Ala Asn Ala Pro Thr
145                 150                 155                 160

Arg Phe Leu Val Ser Gly Met Gly Asp Ala Leu Ser Thr Tyr Phe Glu
                165                 170                 175

Ala Arg Ala Thr Ser Arg Ser Phe Ser Lys Val Asn Ala Gly Leu Pro
            180                 185                 190

Asn Gly Val His Ala Gly Ala Ala Pro Ile Ala Arg Gly Thr Lys Ala
            195                 200                 205

Ala Leu Ala Leu Ala Lys Leu Cys Tyr Glu Thr Leu Leu Glu Asp Gly
210                 215                 220

Val Gln Ala Lys Leu Ala Ser Asp Ser Asn Lys Val Thr Thr Ala Leu
225                 230                 235                 240

Glu Asn Ile Ile Glu Thr Asn Ile Leu Leu Ser Gly Leu Gly Phe Glu
                245                 250                 255

Ser Gly Gly Leu Ala Ala Ala His Ala Ile His Asn Gly Leu Thr Val
            260                 265                 270

Leu Glu Gly Thr His His Tyr Phe His Gly Glu Lys Val Ala Phe Ser
            275                 280                 285

Thr Ile Ala Gln Leu Val Leu Glu Asn Ala Pro Lys Glu Glu Val Asn
            290                 295                 300
```

Glu Val Leu Ala Phe Cys Ala Ala Val Gly Leu Pro Val Cys Leu Ser
305                 310                 315                 320

Asp Ile Gly Val Asp Ser Ile Thr Asp Glu Glu Leu Ala Gln Val Ala
            325                 330                 335

Ala Leu Ala Cys Ile Pro Glu Glu Ser Ile His Ala Met Pro Phe Pro
            340                 345                 350

Ile Thr Glu Glu Ala Val Ala Ala Ile Ile Val Ala Asp Gln Leu
        355                 360                 365

Gly Gln Ala Phe Lys Gln Gly Arg Lys Ser
    370                 375

<210> SEQ ID NO 31
<211> LENGTH: 370
<212> TYPE: PRT
<213> ORGANISM: Geo. Stearothermophilus

<400> SEQUENCE: 31

Met Ala Ala Glu Arg Val Phe Ile Ser Pro Ala Lys Tyr Val Gln Gly
1               5                   10                  15

Lys Asn Val Ile Thr Lys Ile Ala Asn Tyr Leu Glu Gly Ile Gly Asn
            20                  25                  30

Lys Thr Val Val Ile Ala Asp Glu Ile Val Trp Lys Ile Ala Gly His
        35                  40                  45

Thr Ile Val Asn Glu Leu Lys Lys Gly Asn Ile Ala Ala Glu Glu Val
    50                  55                  60

Val Phe Ser Gly Glu Ala Ser Arg Asn Glu Val Glu Arg Ile Ala Asn
65                  70                  75                  80

Ile Ala Arg Lys Ala Glu Ala Ile Val Ile Gly Val Gly Gly Gly
                85                  90                  95

Lys Thr Leu Asp Thr Ala Lys Ala Val Ala Asp Glu Leu Asp Ala Tyr
            100                 105                 110

Ile Val Ile Val Pro Thr Ala Ala Ser Thr Asp Ala Pro Thr Ser Ala
            115                 120                 125

Leu Ser Val Ile Tyr Ser Asp Asp Gly Val Phe Glu Ser Tyr Arg Phe
    130                 135                 140

Tyr Lys Lys Asn Pro Asp Leu Val Leu Val Asp Thr Lys Ile Ile Ala
145                 150                 155                 160

Asn Ala Pro Pro Arg Leu Leu Ala Ser Gly Ile Ala Asp Ala Leu Ala
                165                 170                 175

Thr Trp Val Glu Ala Arg Ser Val Ile Lys Ser Gly Gly Lys Thr Met
            180                 185                 190

Ala Gly Gly Ile Pro Thr Ile Ala Ala Glu Ala Ile Ala Glu Lys Cys
        195                 200                 205

Glu Gln Thr Leu Phe Lys Tyr Gly Lys Leu Ala Tyr Glu Ser Val Lys
    210                 215                 220

Ala Lys Val Val Thr Pro Ala Leu Glu Ala Val Val Glu Ala Asn Thr
225                 230                 235                 240

Leu Leu Ser Gly Leu Gly Phe Glu Ser Gly Gly Leu Ala Ala Ala His
                245                 250                 255

Ala Ile His Asn Gly Phe Thr Ala Leu Glu Gly Glu Ile His His Leu
            260                 265                 270

Thr His Gly Glu Lys Val Ala Phe Gly Thr Leu Val Gln Leu Ala Leu
        275                 280                 285

Glu Glu His Ser Gln Gln Glu Ile Glu Arg Tyr Ile Glu Leu Tyr Leu
    290                 295                 300

Ser Leu Asp Leu Pro Val Thr Leu Glu Asp Ile Lys Leu Lys Asp Ala
305                 310                 315                 320

Ser Arg Glu Asp Ile Leu Lys Val Ala Lys Ala Ala Thr Ala Glu Gly
            325                 330                 335

Glu Thr Ile His Asn Ala Phe Asn Val Thr Ala Asp Asp Val Ala Asp
                340                 345                 350

Ala Ile Phe Ala Ala Asp Gln Tyr Ala Lys Ala Tyr Lys Glu Lys His
            355                 360                 365

Arg Lys
    370

<210> SEQ ID NO 32
<211> LENGTH: 367
<212> TYPE: PRT
<213> ORGANISM: Staphylococcus epidermidis

<400> SEQUENCE: 32

Met Ser Lys Phe Ile Tyr Gln Ser Pro Gly Arg Tyr Val Gln Gly Lys
1               5                   10                  15

Gly Ile Val Ser Ser Ile Ala Glu Glu Thr Glu Arg Leu Gly Ser His
            20                  25                  30

Ala Leu Ile Ile Ala Asp Glu Val Val Trp Asn Ile Thr Glu Glu Lys
        35                  40                  45

Ile Lys Glu Ser Phe Ser Ala Asn Asn Asn Val Asp Phe Glu Tyr Glu
    50                  55                  60

Val Phe Lys Gly Glu Ser Ser Glu Glu Ile Gln Arg Ile Val Lys
65                  70                  75                  80

Gln Tyr Lys Glu Lys Asn Ile Asp Val Val Ile Gly Leu Gly Gly Gly
                85                  90                  95

Lys Ala Leu Asp Thr Gly Lys Ala Val Ala Phe Glu Leu Lys Ala Ser
            100                 105                 110

Val Ile Asp Phe Ala Ser Thr Ala Ser Met Asp Ala Pro Thr Ala Ala
        115                 120                 125

Val Ser Val Ile Tyr Asn Glu Asp Gly Ser Phe Ser Gly Tyr Glu Phe
    130                 135                 140

Tyr Pro Lys Asn Pro Asp Thr Val Ile Val Asp Ser Glu Ile Val Ala
145                 150                 155                 160

Gln Ala Pro Val Arg Leu Phe Ala Ser Gly Met Ser Asp Gly Leu Ala
                165                 170                 175

Thr Leu Ile Glu Val Glu Ser Thr Leu Arg Arg Gln Gly Gln Asn Met
            180                 185                 190

Phe His Gly Lys Pro Thr Leu Ala Ser Leu Ala Ile Ala Gln Lys Cys
        195                 200                 205

Glu Glu Val Ile Phe Glu Tyr Gly Tyr Ser Ala Tyr Thr Ser Val Glu
    210                 215                 220

Lys His Ile Val Thr Pro Gln Val Asp Ala Val Ile Glu Ala Asn Thr
225                 230                 235                 240

Leu Leu Ser Gly Leu Gly Phe Glu Asn Gly Gly Leu Ala Gly Ala His
                245                 250                 255

Ala Ile His Asn Gly Phe Thr Ala Leu Glu Gly Asp Ile His His Leu
            260                 265                 270

Thr His Gly Glu Lys Val Ala Tyr Gly Ile Leu Val Gln Leu Val Leu
        275                 280                 285

Glu Asn Ala Pro Thr Glu Lys Phe Met Lys Tyr Lys Thr Phe Phe Asp

```
                290             295             300
Asn Ile Asn Met Pro Thr Thr Leu Glu Gly Leu His Ile Glu Asn Thr
305                 310                 315                 320

Ser Tyr Glu Glu Leu Val Gln Val Gly Glu Arg Ala Leu Thr Pro Asn
                325                 330                 335

Asp Thr Phe Ala Asn Leu Ser Asp Lys Ile Thr Ala Asp Glu Ile Ala
            340                 345                 350

Asp Ala Ile Leu Thr Val Asn Asp Leu Ser Lys Ser Gln Phe Asn
        355                 360                 365

<210> SEQ ID NO 33
<211> LENGTH: 29
<212> TYPE: DNA
<213> ORGANISM: Artificial Sequence
<220> FEATURE:
<223> OTHER INFORMATION: Primer9

<400> SEQUENCE: 33
ccctacgtat tggaacgggt gcagttggt                                29

<210> SEQ ID NO 34
<211> LENGTH: 29
<212> TYPE: DNA
<213> ORGANISM: Artificial Sequence
<220> FEATURE:
<223> OTHER INFORMATION: Primer10

<400> SEQUENCE: 34
cccgaattcc cgggttgctg gcaacaaga                                29

<210> SEQ ID NO 35
<211> LENGTH: 29
<212> TYPE: DNA
<213> ORGANISM: Artificial Sequence
<220> FEATURE:
<223> OTHER INFORMATION: Primer11

<400> SEQUENCE: 35
cccgaattct ttgagcgccc aatttggaa                                29

<210> SEQ ID NO 36
<211> LENGTH: 29
<212> TYPE: DNA
<213> ORGANISM: Artificial Sequence
<220> FEATURE:
<223> OTHER INFORMATION: Primer12

<400> SEQUENCE: 36
cccaggcctc cggaacgcca acgtacaca                                29

<210> SEQ ID NO 37
<211> LENGTH: 20
<212> TYPE: DNA
<213> ORGANISM: Artificial Sequence
<220> FEATURE:
<223> OTHER INFORMATION: Primer17

<400> SEQUENCE: 37
acgagccgct gacactggat                                          20

<210> SEQ ID NO 38
<211> LENGTH: 20
<212> TYPE: DNA
<213> ORGANISM: Artificial Sequence
```

```
<220> FEATURE:
<223> OTHER INFORMATION: Primer18

<400> SEQUENCE: 38
gccgtcttcg ccttcgttca                                               20

<210> SEQ ID NO 39
<211> LENGTH: 20
<212> TYPE: DNA
<213> ORGANISM: Artificial Sequence
<220> FEATURE:
<223> OTHER INFORMATION: Primer21

<400> SEQUENCE: 39
tgtcataagt cgccgaaccg                                               20

<210> SEQ ID NO 40
<211> LENGTH: 20
<212> TYPE: DNA
<213> ORGANISM: Artificial Sequence
<220> FEATURE:
<223> OTHER INFORMATION: Primer22

<400> SEQUENCE: 40
tgattgtatg ccgccacgaa                                               20

<210> SEQ ID NO 41
<211> LENGTH: 20
<212> TYPE: DNA
<213> ORGANISM: Artificial Sequence
<220> FEATURE:
<223> OTHER INFORMATION: Primer23

<400> SEQUENCE: 41
ggtgttgcag aagagcttgt                                               20

<210> SEQ ID NO 42
<211> LENGTH: 20
<212> TYPE: DNA
<213> ORGANISM: Artificial Sequence
<220> FEATURE:
<223> OTHER INFORMATION: Primer24

<400> SEQUENCE: 42
gtgccgcaat cggaataatc                                               20

<210> SEQ ID NO 43
<211> LENGTH: 20
<212> TYPE: DNA
<213> ORGANISM: Artificial Sequence
<220> FEATURE:
<223> OTHER INFORMATION: Primer29

<400> SEQUENCE: 43
agatcttaag ccgtgtggag                                               20

<210> SEQ ID NO 44
<211> LENGTH: 20
<212> TYPE: DNA
<213> ORGANISM: Artificial Sequence
<220> FEATURE:
<223> OTHER INFORMATION: Primer30

<400> SEQUENCE: 44
cgcaacaata ctgccgattc                                               20
```

<210> SEQ ID NO 45
<211> LENGTH: 20
<212> TYPE: DNA
<213> ORGANISM: Artificial Sequence
<220> FEATURE:
<223> OTHER INFORMATION: Primer33

<400> SEQUENCE: 45
ttggaggcga acaaagaaca                                                  20

<210> SEQ ID NO 46
<211> LENGTH: 20
<212> TYPE: DNA
<213> ORGANISM: Artificial Sequence
<220> FEATURE:
<223> OTHER INFORMATION: Primer34

<400> SEQUENCE: 46
cggcaatgga aaagaaatg                                                   20

<210> SEQ ID NO 47
<211> LENGTH: 20
<212> TYPE: DNA
<213> ORGANISM: Artificial Sequence
<220> FEATURE:
<223> OTHER INFORMATION: Primer GDH10-R

<400> SEQUENCE: 47
agtccgacac tcaggcagaa                                                  20

<210> SEQ ID NO 48
<211> LENGTH: 20
<212> TYPE: DNA
<213> ORGANISM: Artificial Sequence
<220> FEATURE:
<223> OTHER INFORMATION: Primer GDH11-F

<400> SEQUENCE: 48
ggcttaccgt gctcgaagaa                                                  20

<210> SEQ ID NO 49
<211> LENGTH: 20
<212> TYPE: DNA
<213> ORGANISM: Artificial Sequence
<220> FEATURE:
<223> OTHER INFORMATION: Primer D-LDH-3

<400> SEQUENCE: 49
gcgttcttct gctaacatcc                                                  20

<210> SEQ ID NO 50
<211> LENGTH: 20
<212> TYPE: DNA
<213> ORGANISM: Artificial Sequence
<220> FEATURE:
<223> OTHER INFORMATION: Primer GDH-6

<400> SEQUENCE: 50
gtgctcgctt cctatatcgt                                                  20

<210> SEQ ID NO 51
<211> LENGTH: 29
<212> TYPE: DNA
<213> ORGANISM: Artificial Sequence
<220> FEATURE:
<223> OTHER INFORMATION: Primer GDH-7

<400> SEQUENCE: 51
gggctcgaga tgacgaaaat cattacctc                               29

<210> SEQ ID NO 52
<211> LENGTH: 29
<212> TYPE: DNA
<213> ORGANISM: Artificial Sequence
<220> FEATURE:
<223> OTHER INFORMATION: Primer GDH-12

<400> SEQUENCE: 52
gggggatccg tgctcgcttc ctatatcgt                               29

<210> SEQ ID NO 53
<211> LENGTH: 1832
<212> TYPE: DNA
<213> ORGANISM: Bacillus coagulans
<220> FEATURE:
<221> NAME/KEY: misc_feature
<223> OTHER INFORMATION: Insertion sequence upstream of the gldA gene in
      Bacillus coagulans strain QZ19

<400> SEQUENCE: 53
caaaaataag tatgtgtaaa attttactcg acggggcata tgagtggaaa aaaatgggaa     60
gacgctctat catctaattg tacacttcaa gatgaacatc tagagagaga ggtcttccca    120
tggatattat atcaataatt gctggattat taaaggatac aaagagtctt atcgaatttg    180
aagaacagct taaacttctg atgcagaagg cttttacaca atgggttggg gaaatatttg    240
aagagttaga taaataatt aaacaggaga agttagagga gggctgggtg tactgccgga    300
gtgataacag aaacattcag tttctatttg gaagtgtgac cttaaacgt tcattaatgc     360 atgacaagag aggaaattcc cattatcctc tggatgaatg gttagggctg gtaccacacc    420
aacgatacag cccgttagtg gaattaaagg tggcagagtt ggcaagtgag aacacctatc    480
gggaagtagc tgatattta aagagtgga cagcagtgag tcttagtcac acaactgtag      540
ggaacatggt aaaacacgta gggaaaactc aggcggaagc cgataaggca cttgtagaag    600
agctagaaat agctgtttcc ctgcctgagg ggaagaaggt agactacctg ttttctgaag    660
cagatggtgt attcgttcgg ggactaaaaa agaaacagag tatggaagtc caccacgcca    720
ttctctatga gggatggcaa accaatggta aagggtctc cctgcgtcag cccacagtca    780
tcatgacaac ggaagccatc cagacatttt ggggatgaag tccaagcaca gctgccaaca    840
cctactccct cgaaaaaacg catgtcatta caaacagtga tggaggtgcg ggatacacag    900
ctgaacggtt tcaaacagct ttctcacagt cggaatttcc ggtgctcaac cagctggata    960
cctaccacgt tgcacaagcc atcataagga catttggggg cggaaagagc gagatcaagg   1020
agcaaattag aaaagcgatt agaacgcatg acctggacca actcacgtta tatttggata   1080
cgcacgaaag caccttgacg gataaaaagg ctctcaagaa aatcaaggaa ttccgttcgt   1140
atatcttgaa aaactgggac cgcatttttg actggagaga cagggtgaaa aacgtgccgg   1200
aaggtgcgag aggcctagga gcgatggaat cgaatcaaag gcatatctcc ttcaggatga   1260
aaaaaagggg catgcattgg agtgaacttg gcgcagaagc catggtgaaa atcaaacaag   1320
gcatactcaa tggacattg agagaagtct atctgaaaca ccgttcaaga agcgagagaa   1380
agcaacggaa cttgaaacaa ttcatcagga tgtctcaact gctcaagcag cctgtacgcc   1440
cgtcagtggg cgtaaagcac ggatcagttg ccctgcattc aagcagttca tcggcaatgg   1500

```
gacatttaag caaaatatta gagctttcgt tttaagcctg gctcagtggg gactgatcgt    1560
tgaggcgcgc gaaatttacg agactcctgc gggaaaagcg agccaggaga gaccccgcag    1620
cgaggtacga gcgaggaggc tcgccggccg accgcggaaa gcgagtgaat tcgcgcgcc     1680 tcaacatccc cgttatccat ctttatacgg aaatattaca tcttttccga aaattacacc    1740
gagcaagtaa agcacggtag ccgaaagtgt acaaaagag tgtcttggaa tacccgatat     1800
ttaaaccttg tcgagaaaaa cttgacacat ac                                  1832
```

<210> SEQ ID NO 54
<211> LENGTH: 3120
<212> TYPE: DNA
<213> ORGANISM: Bacillus coagulans
<220> FEATURE:
<221> NAME/KEY: misc_feature
<223> OTHER INFORMATION: Insertion sequence upstream of the gldA gene of
      Bacillus coagulans strain QZ19 with the gldA gene included

<400> SEQUENCE: 54

```
caaaaataag tatgtgtaaa attttactcg acgggcata tgagtggaaa aaaatgggaa      60
gacgctctat catctaattg tacacttcaa gatgaacatc tagagagaga ggtcttccca    120
tggatattat atcaataatt gctggattat taaaggatac aaagagtctt atcgaatttg    180
aagaacagct taaacttctg atgcagaagg cttttacaca atgggttggg gaaatatttg    240
aagagttaga taaaataatt aaacaggaga agttagagga gggctgggtg tactgccgga    300
gtgataacag aaacattcag tttctatttg gaagtgtgac cttaaacgt tcattaatgc      360 atgacaagag aggaaattcc cattatcctc tggatgaatg gttagggctg gtaccacacc    420
aacgatacag cccgttagtg gaattaaagg tggcagagtt ggcaagtgag aacacctatc    480
gggaagtagc tgatatttta aaagagtgga cagcagtgag tcttagtcac acaactgtag    540
ggaacatggt aaaacacgta gggaaaactc aggcggaagc cgataaggca cttgtagaag    600
agctagaaat agctgtttcc ctgcctgagg ggaagaaggt agactacctg ttttctgaag    660
cagatggtgt attcgttcgg ggactaaaaa agaaacagag tatggaagtc caccacgcca    720
ttctctatga gggatggcaa accaatggta aaagggtctc cctgcgtcag cccacagtca    780
tcatgacaac ggaagccatc cagacatttt ggggatgaag tccaagcaca gctgccaaca    840
cctactccct cgaaaaaacg catgtcatta caaacagtga tggaggtgcg ggatacacag    900
ctgaacggtt tcaaacagct ttctcacagt cggaatttcc ggtgctcaac cagctggata    960
cctaccacgt tgcacaagcc atcataagga catttggggg cggaaagagc gagatcaagg   1020
agcaaattag aaaagcgatt agaacgcatg acctggacca actcacgtta tatttggata   1080
cgcacgaaag caccttgacg gataaaaagg ctctcaagaa aatcaaggaa ttccgttcgt    1140
atatcttgaa aaactgggac cgcattttg actggagaga caggtgaaa aacgtgccgg      1200 aaggtgcgag aggcctagga gcgatggaat cgaatcaaag gcatatctcc ttcaggatga   1260
aaaaaagggg catgcattgg agtgaacttg gcgcagaagc catggtgaaa atcaaacaag   1320
gcatactcaa tgggacattg agagaagtct atctgaaaca ccgttcaaga agcgagagaa   1380
agcaacggaa cttgaaacaa ttcatcagga tgtctcaact gctcaagcag cctgtacgcc    1440
cgtcagtggg cgtaaagcac ggatcagttg ccctgcattc aagcagttca tcggcaatgg   1500
gacatttaag caaaatatta gagctttcgt tttaagcctg gctcagtggg gactgatcgt   1560
tgaggcgcgc gaaatttacg agactcctgc gggaaaagcg agccaggaga gaccccgcag   1620
cgaggtacga gcgaggaggc tcgccggccg accgcggaaa gcgagtgaat tcgcgcgcc    1680
```

-continued

```
tcaacatccc cgttatccat ctttatacgg aaatattaca tcttttccga aaattacacc   1740
gagcaagtaa agcacggtag ccgaaagtgt acaaaaagag tgtcttggaa tacccgatat   1800
ttaaaccttg tcgagaaaaa cttgacacat accaaaaata agttatgatg gaattgtgct   1860
tgttatattt ttcacaaaaa gaggaggcat ttttatgacg aaaatcatta cctctccaag   1920
caagtttata caaggccccg atgaattgtc caggctttcg gcgtatacgg aaaggcttgg   1980 caaaaagca tttattattg cggatgattt tgtcaccggc cttgtcggca aaacggttga   2040
agaaagctat gccggcaaag aaacggggta tcaaatggca ttattcggtg gcgagtgttc   2100
taaaccggaa atcgaacggc tttgtgaaat gagcaaatcc gaggaagccg atgtcgttgt   2160
cggaatcggc ggcggaaaaa cattggatac cgcaaaagca gtcgggtatt acaataacat   2220
tccggtgatt gtcgcgccga ccatcgcttc caccaatgcc ccgacaagcg ccctgtctgt   2280
tatttacaaa gagaacggcg agtttgaaga atacttgatg ctgccgctga cccgactttt   2340
tgtcattatg gatacgaaag tgattgcctc tgccctgcc cgcctgctcg tttccggcat   2400
gggagatgcg cttgcgacgt attttgaagc gcgcgccact aagcgggcaa ataaaacgac   2460
gatggcaggc gggcgtgtta cggaagcggc gatcgcgctt gcaaaacttt gttatgacac   2520
gcaaattttg gaaggtttaa aagcaaaact ggcagcggaa aacatcttg ttacggaagc   2580 agtgaaaaaa atcattgaag cgaatacgta tctgagcgga atcggttctg aaagcggcgg   2640
ccttgctgcg gcacatgcga tccataatgg gcttaccgtg ctcgaagaaa cccatcatat   2700
gtaccacggc gaaaaagtgg cattcggtac cctcgcccag ctgattttgg aagatgcgcc   2760
gaaagcggaa attgaagagg tggtctcctt ctgcctgagt gtcggacttc ccgtcacgct   2820
cggggatttg ggcgtgaaag aactgaatga ggaaaagctc cgaaaagtgg ctgaactttc   2880
ctgtgcggaa ggcgaaacga tttataacat gccgtttgaa gtcacgcctg accttgtgta   2940
cgcagcaatc gttaccgctg attccgtcgg gcggtattat aaggaaaaat gggcatgaca   3000
gtaaaaaggg gctgctcccg gttccgggga cagcccttt tgcccatttt cactgtaatc   3060
cagttgtaca gatttttct tccagttcgt cttttcggc cgctgatagc aggttttcag   3120
```

<210> SEQ ID NO 55
<211> LENGTH: 1500
<212> TYPE: DNA
<213> ORGANISM: Bacillus coagulans
<220> FEATURE:
<221> NAME/KEY: misc_feature
<223> OTHER INFORMATION: Native gldA sequence without the insertion
      sequence; position of insertion is marked by arrow

<400> SEQUENCE: 55

```
cgttcttctg ctaacatcct tcattcctcc gtctgatgat attttatcac atagttattc     60
ataatcaacc gttttcaatc aaaaaatatc attttttattc aaaacacatc atatttctgt    120
cacattttgt cgatacagct ctatttact tgttattccc cgaaaattga acgttttga      180 aaaagtatgg atgataggat gaaaaggttt tcttatctgc aaaaataagt tatgatggaa    240
ttgtgcttgt tatattttc acaaaagag gaggcatttt tatgacgaaa atcattacct      300
ctccaagcaa gtttatacaa ggccccgatg aattgtccag gctttcggcg tatacggaaa    360
ggcttggcaa aaagcatttt attattgcgg atgattttgt caccggcctt gtcggcaaaa    420
cggttgaaga aagctatgcc ggcaaagaaa cggggtatca aatggcatta ttcggtggcg    480
agtgttctaa accggaaatc gaacggcttt gtgaaatgag caaatccgag gaagccgatg    540
```

```
tcgttgtcgg aatcggcggc ggaaaaacat tggataccgc aaaagcagtc gggtattaca        600
ataacattcc ggtgattgtc gcgccgacca tcgcttccac caatgccccg acaagcgccc        660
tgtctgttat ttacaaagag aacggcgagt ttgaagaata cttgatgctg ccgctgaacc        720
cgacttttgt cattatggat acgaaagtga ttgcctctgc ccctgcccgc ctgctcgttt        780
ccggcatggg agatgcgctt gcgacgtatt ttgaagcgcg cgccactaag cgggcaaata        840
aaacgacgat ggcaggcggg cgtgttacgg aagcggcgat cgcgcttgca aaactttgtt        900
atgacacgca aattttggaa ggtttaaaag caaaactggc agcggaaaaa catcttgtta        960
cggaagcagt ggaaaaaatc attgaagcga atacgtatct gagcggaatc ggttctgaaa       1020
gcggcggcct tgctgcggca catgcgatcc ataatgggct taccgtgctc gaagaaaccc       1080
atcatatgta ccacggcgaa aaagtggcat tcggtaccct cgcccagctg attttggaag       1140
atgcgccgaa agcggaaatt gaagaggtgg tctccttctg cctgagtgtc ggacttcccg       1200
tcacgctcgg ggatttgggc gtgaaagaac tgaatgagga aaagctccga aaagtggctg       1260
aactttcctg tgcggaaggc gaaacgattt ataacatgcc gtttgaagtc acgcctgacc       1320
ttgtgtacgc agcaatcgtt accgctgatt ccgtcgggcg gtattataag gaaaaatggg       1380
catgacagta aaaaggggct gctcccggtt ccggggacag ccctttttgc ccattttcac       1440
tgtaatccag ttgtacagat ttttctttcc agttcgtctt tttcggccgc tgatagcagg       1500
```

<210> SEQ ID NO 56
<211> LENGTH: 148
<212> TYPE: DNA
<213> ORGANISM: Artificial sequence
<220> FEATURE:
<223> OTHER INFORMATION: promoter sequence

<400> SEQUENCE: 56

```
cgaaaattac accgagcaag taaagcacgg tagccgaaag tgtacaaaaa gagtgtcttg         60
gaatacccga tatttaaacc ttgtcgagaa aaacttgaca cataccaaaa ataagttatg        120
atggaattgt gcttgttata ttttcac                                             148
```